(12) United States Patent
Bhargava et al.

(10) Patent No.: US 9,920,367 B2
(45) Date of Patent: Mar. 20, 2018

(54) HIGH RESOLUTION ANALYSIS OF MAMMALIAN TRANSCRIPTOME USING GENE POOL SPECIFIC PRIMERS

(71) Applicant: The Regents of the University of California, Oakland, CA (US)

(72) Inventors: Vipul Bhargava, La Jolla, CA (US); Pang Ko, La Jolla, CA (US); Shankar Subramaniam, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1132 days.

(21) Appl. No.: 14/105,704

(22) Filed: Dec. 13, 2013

(65) Prior Publication Data
US 2014/0148347 A1    May 29, 2014

Related U.S. Application Data

(63) Continuation of application No. PCT/US2012/042413, filed on Jun. 14, 2012.

(60) Provisional application No. 61/497,221, filed on Jun. 15, 2011.

(51) Int. Cl.
    *C12Q 1/68*      (2006.01)
    *G06F 19/22*      (2011.01)

(52) U.S. Cl.
    CPC ......... *C12Q 1/6874* (2013.01); *C12Q 1/6869* (2013.01); *G06F 19/22* (2013.01)

(58) Field of Classification Search
None
See application file for complete search history.

(56) References Cited

U.S. PATENT DOCUMENTS

| | | | |
|---|---|---|---|
| 7,749,697 B2 | 7/2010 | Oleksiewicz et al. | |
| 2010/0029511 A1* | 2/2010 | Raymond | C12Q 1/686 506/26 |

OTHER PUBLICATIONS

Cao et al., 2004, "Comparing Gene Discovery from Affymetrix GeneChip Microarrays and Clontech PCR-Select cDNA Subtraction: A Case Study," BMA Genomics, vol. 5 (10 pages).
Nelson et al., 1999, "Negative Selection: A Method for Obtaining Low-Abundance cDNAs Using High-Density cDNA Clone Arrays," Genetic Analysis: Biomolecular Engineering, 15:209-215.
PCT International Search Report for PCT/US2012/042413 dated Oct. 11, 2012 (2 pages).

* cited by examiner

*Primary Examiner* — Christopher M Gross
(74) *Attorney, Agent, or Firm* — Eversheds Suthreland (US) LLP

(57) ABSTRACT

The present invention provides methods and systems for analyzing mammalian transcriptomes, particularly, for low abundant transcripts, and with the use of high throughput technologies. Heptamer primers and sequence tags generated by the iterative randomized algorithm, as well as the sequencing-library generation system for amplifying and synthesis-based sequencing low abundant transcripts using the heptamer primers are also provided. The present invention further provides the use of the invention system and method for identifying key embryological lineage specific transcripts that anticipate differentiation of specific cell types.

9 Claims, 13 Drawing Sheets

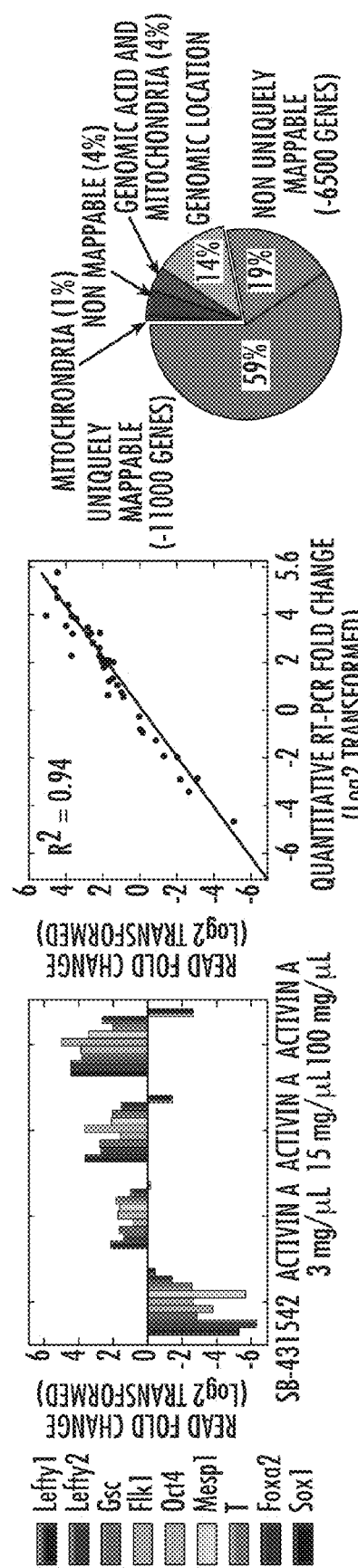

SEQUENCE LISTING

```
<160> NUMBER OF SEQ ID NOS: 197

<210> SEQ ID NO 1
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Biotin
<220> FEATURE:
<221> NAME/KEY: misc_feature
<222> LOCATION: (50)..(51)
<223> OTHER INFORMATION: Phosphorothioate linkage

<400> SEQUENCE: 1
```
aatgatacgg cgaccaccga gatctacact ctttccctac acgacgctct t          51

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Phospho

<400> SEQUENCE: 2
agagcgtcgt gtagggaaag agtgtagatc tcggtggtcg ccgtatcatt           50

<210> SEQ ID NO 3
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (53)..(54)
<223> OTHER INFORMATION: Phosphorothioate linkage

<400> SEQUENCE: 3
caagcagaag acggcatacg agatcggtct cggcattcct gctgaaccgc tctt       54

<210> SEQ ID NO 4
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Phospho

<400> SEQUENCE: 4
agagcggttc agcaggaatg ccgagaccga tctcgtatgc cgtcttctgc ttg        53

<210> SEQ ID NO 5
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatgatacgg cgaccaccga gatctacact ctttccctac acgacgctct tccgaata   58

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caagcagaag acggcatacg agatcggtct cggcattcct gctgaaccgc tcttccgata 60

<210> SEQ ID NO 7
<211> LENGTH: 7

```
<212> TYPE: DNA
<213> ORGANISM: Artificial Sequence
<220> FEATURE:
<223> OTHER INFORMATION: Description of Artificial Sequence: Synthetic
      adapter oligonucleotide

<400> SEQUENCE: 7 ccgaata                                                                    7

<210> SEQ ID NO 8
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8 cccagtg                                                                    7

<210> SEQ ID NO 9
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9 ccccaga                                                                    7

<210> SEQ ID NO 10
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10 cccccaa                                                                    7

<210> SEQ ID NO 11
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11 ctcccca                                                                    7

<210> SEQ ID NO 12
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12 cttcacg                                                                    7

<210> SEQ ID NO 13
<211> LENGTH: 7
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 13 gcaacag                                                                       7

<210> SEQ ID NO 14
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14 tgacagc                                                                       7

<210> SEQ ID NO 15
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15 tggctct                                                                       7

<210> SEQ ID NO 16
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16 tggcttc                                                                       7

<210> SEQ ID NO 17
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17 tccctcc                                                                       7

<210> SEQ ID NO 18
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18 ccttccc                                                                       7

<210> SEQ ID NO 19
<211> LENGTH: 7
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 19 cagaccc                                                                    7

<210> SEQ ID NO 20
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20 gcaaacc                                                                    7

<210> SEQ ID NO 21
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21 ccaggac                                                                    7

<210> SEQ ID NO 22
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22 cacacac                                                                    7

<210> SEQ ID NO 23
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23 tctccga                                                                    7

<210> SEQ ID NO 24
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24 cctccca                                                                    7

<210> SEQ ID NO 25
<211> LENGTH: 7
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 25 tgaccca                                                                  7

<210> SEQ ID NO 26
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26 caaagcc                                                                  7

<210> SEQ ID NO 27
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27 caacccc                                                                  7

<210> SEQ ID NO 28
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28 cccagca                                                                  7

<210> SEQ ID NO 29
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29 cccccaa                                                                  7

<210> SEQ ID NO 30
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30 ctcgtcc                                                                  7

<210> SEQ ID NO 31
<211> LENGTH: 7
<212> TYPE: DNA
<213> ORGANISM: Artificial Sequence
<220> FEATURE:
<223> OTHER INFORMATION: Description of Artificial Sequence: Synthetic
```

```
          primer

<400> SEQUENCE: 31 cttcccc                                                                    7

<210> SEQ ID NO 32
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32 gcctctc                                                                    7

<210> SEQ ID NO 33
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33 gcctctg                                                                    7

<210> SEQ ID NO 34
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34 gcgaact                                                                    7

<210> SEQ ID NO 35
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35 tcagccc                                                                    7

<210> SEQ ID NO 36
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36 tctccga                                                                    7

<210> SEQ ID NO 37
<211> LENGTH: 7
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 37 tgccatc                                                                  7

<210> SEQ ID NO 38
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38 tgccttg                                                                  7

<210> SEQ ID NO 39
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39 tgagcct                                                                  7

<210> SEQ ID NO 40
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40 tcctcgt                                                                  7

<210> SEQ ID NO 41
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41 tctgcct                                                                  7

<210> SEQ ID NO 42
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42 ctgccct                                                                  7

<210> SEQ ID NO 43
<211> LENGTH: 7
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 43 tgccact                                                                    7

<210> SEQ ID NO 44
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44 cttcacg                                                                    7

<210> SEQ ID NO 45
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45 gcaacag                                                                    7

<210> SEQ ID NO 46
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46 cctctgc                                                                    7

<210> SEQ ID NO 47
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47 gcaaacc                                                                    7

<210> SEQ ID NO 48
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48 ccccaga                                                                    7

<210> SEQ ID NO 49
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
```

```
ctcagca                                                              7
```

<210> SEQ ID NO 50
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

```
tgacagc                                                              7
```

<210> SEQ ID NO 51
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

```
cacacac                                                              7
```

<210> SEQ ID NO 52
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

```
cagcagc                                                              7
```

<210> SEQ ID NO 53
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

```
ccaccag                                                              7
```

<210> SEQ ID NO 54
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

```
cccagca                                                              7
```

<210> SEQ ID NO 55
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55 cccccaa                                                                    7

<210> SEQ ID NO 56
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56 ccttccc                                                                    7

<210> SEQ ID NO 57
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57 cttcccc                                                                    7

<210> SEQ ID NO 58
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58 gcaacag                                                                    7

<210> SEQ ID NO 59
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59 gcctcag                                                                    7

<210> SEQ ID NO 60
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60 tccctcc                                                                    7

<210> SEQ ID NO 61
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61 tgaccca                                                                    7

<210> SEQ ID NO 62
<211> LENGTH: 7
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 62 tgagcct                                                            7

<210> SEQ ID NO 63
<211> LENGTH: 7
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 63 cagcact                                                            7

<210> SEQ ID NO 64
<211> LENGTH: 7
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 64 gcgaact                                                            7

<210> SEQ ID NO 65
<211> LENGTH: 7
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 65 ctcccag                                                            7

<210> SEQ ID NO 66
<211> LENGTH: 7
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 66 gccaaag                                                            7

<210> SEQ ID NO 67
<211> LENGTH: 7
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 67 ccccaga                                                            7

<210> SEQ ID NO 68
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68 tcagcca                                                              7

<210> SEQ ID NO 69
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69 gaagcca                                                              7

<210> SEQ ID NO 70
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70 tgacagc                                                              7

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cgctgaatct gggctgagtc cc                                            22

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tgcaagtagc cgacttcgga gc                                            22

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gggggtcgag aaagcaacga gg                                            22

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
agaggaagtg tgcgacccca a                                              21

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
tgaagtgccc gaagccctcc cta                                            23

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
tctagaaacc tggacgccgc c                                              21

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
ctccgatgta tgaaggggct gct                                            23

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
ccccatgcca ggcagcttgg                                                20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
ttccccagga ctccgaggcg                                                20

<210> SEQ ID NO 80

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
aagcatagcc gcgctgaggc                                         20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
tacagctccc cgggcctgac                                         20

<210> SEQ ID NO 82
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
acctcctcat actcgtg                                            17

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
gacgtgcagc ggaaagccct                                         20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
aaccggccac ccctggaagt                                         20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
tccgaccccg tggggttgtt                                         20

<210> SEQ ID NO 86
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
acacgagact cgggcgagct                                                  20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tgggctcagc cggggctaat                                                  20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
acactgtgcc cagcgtcagc                                                  20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gagctcaacg aagcggccgt                                                  20

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gcacatgaag gagcacccgg a                                                21

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gggacacgcc actgcatgct                                                  20

<210> SEQ ID NO 92
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 92
tgacgtcatg cccgggacca                                               20

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cccccaccta tagcaccgca gg                                            22

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
agggaaccga gtacatgtcc cagt                                          24

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tgcgcagcct ccagacgatg                                               20

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ttcctcccag tgcgtgacgg a                                             21

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ccggcgcagt ctacggaacc                                               20

<210> SEQ ID NO 98
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 98
gcgaagctca ttgtggagac                                              20

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
accaaccatg cctacatcca gag                                          23

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tacgcctgcc cagcctgagt                                              20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tcagccaggc ccgagaggtc                                              20

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gagtggcgtc accagcggta ct                                           22

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gggaaatcct gcctgccggt c                                            21

<210> SEQ ID NO 104
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 104
cgcctttcct gcctggtggg                                                   20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
cgccatctac cagccgctcg                                                   20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tttgggggct acggggctga                                                   20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tgcaggcctc ctaccacccc                                                   20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
acgttggggc aagagcgtgg                                                   20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gaaggtggct ggcgaacgct                                                   20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 110
ccgcgtactc ggctgatgcc                                               20

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
accaagacct aacaaaccc                                                19

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gccgaggtgc gcgtcagtac                                               20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acgcagacgg gaacggaagc                                               20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ggtggcctct gcaagccagg                                               20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ccctgcaagt tgggcagcca                                               20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 116
gctggagcac ctgggtgagc                                              20

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
agggactttg cttctttttc cgggc                                        25

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ccggcctttc aagtgcggct                                              20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gcatcccctt gctggctcgg                                              20

<210> SEQ ID NO 120
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
taccccgata gcctgt                                                  16

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ccaagcgatc acgcaacgtg g                                            21

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 122
gcgagacgta gaccctgggg                                           20

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ggagccgccg cagggttata ttg                                       23

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tcacctccgt gcgtcctgct                                           20

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
actcgtcgtc cagtcccgct c                                         21

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
actagggacc gagggacgcg                                           20

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gagccaaagc ggagtctc                                             18

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
agaggttctg gcatcggttc a                              21

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
acaggacgga caccctggca                                20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
aagcacggcg ccatcaccaa                                20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
aatggccacg ggaacgctgg                                20

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132 aggggggcggg gagaatccaa a                             21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gctgtattcc cctccatcgt g                              21

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gcctaggttg gacatgtttg ccca                                         24

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
cctattccca ggcctctggc ca                                           22

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
acgaggctca cgcaggcagc                                              20

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
cactggccgg ctctttcgct t                                            21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
gcccttctgg cgccggttac a                                            21

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tccgttgcat tgtcccctcc ac                                           22

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gctatgagga ggctttgggc cg                                           22

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 141
aagtgtctgc agccaggggc                                          20

<210> SEQ ID NO 142
<211> LENGTH: 25
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 142
gttcagtcta agaggccagt ctggt                                    25

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 143
ttcggggaac gccctagggg                                          20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 144
actctagcag gccggacgca                                          20

<210> SEQ ID NO 145
<211> LENGTH: 16
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 145
actgataccg tgcctt                                              16

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 146
cgctagacag gagctcgcgc                                          20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
gtcgcccccg caacctttca                                               20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tctacgggct ggggtgagcc                                               20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ccggaaccga gcacggtgtc                                               20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
acagctaagc gcggcgttgt                                               20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gcactggggg acgtgatgcc                                               20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ccgagaaatt gcgcaggcgc                                               20

```
<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ggttcacgcc cgcacccag                                                19

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gccaagtcga caggccgcaa                                               20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155 gcccccctaca cccgcctcat                                              20

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
acatgcctcc agttccccgt tct                                           23

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tgcaactggt agtccgggcc a                                             21

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
tctggagcag tgcaacggca                                               20

<210> SEQ ID NO 159
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
tcctcggtgg cttccggaac a                                              21

<210> SEQ ID NO 160
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
accgacaaca aagtgcggac cc                                             22

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
cacgatctct gtgaatacgc a                                              21

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
ccctgccatt gtccacataa agc                                            23

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ggtgtccagc ccagccgaac                                                20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gatggcactg gtccgggtgc                                                20

<210> SEQ ID NO 165
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
tcaccttgtg atgcgagcgc                                              20

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ctgtgattcg gcccatggtg ctt                                          23

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
gctagcagtg ggcagtggcc                                              20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
actgtgggct ctggctggct                                              20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tgcagcccac gcccatcatg                                              20

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
tccccaggcc ttctggagtg c                                            21

<210> SEQ ID NO 171
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 171
gagacggggg aggggggtgac                                              20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gcggggccag tgagttctgg                                               20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
cacacgtggc ggtcgcaagt                                               20

<210> SEQ ID NO 174
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
catggacatc acggacc                                                  17

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ggggcagcca aggtcgtacc                                               20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
tgcggcactc ctgacgttgc                                               20

<210> SEQ ID NO 177
<211> LENGTH: 20
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 177
cctccgtgct cagtggctgc                                                  20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
cgaaggcccc gttggggatg                                                  20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
cctccactgt gcacgcgtgt                                                  20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
cccgcagcgt cagcgagcta                                                  20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ggcatgcgct ggtgtcgact                                                  20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
ggccatggca cagtgctcct                                                  20

<210> SEQ ID NO 183
<211> LENGTH: 16
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 183
gcacgatgct ctcgaa                                                       16

<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ctctgacgat gtggaaccgc gg                                                22

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
ggtcgccggg gtgaatgctg                                                   20

<210> SEQ ID NO 186
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
tggcgcaccc gctactttg ag                                                 22

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ttcgggcaag agtggcaagc c                                                 21

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
caaggttggc cgacatgggg t                                                 21

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 189
cagtttggcg cggattgccg                                              20

<210> SEQ ID NO 190
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
tgccaaggtc aacgccttc                                               19

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
tctcccagtg tacttcgtgg c                                            21

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
ggtcagccca ggggagcagt                                              20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
tttggggagc tccggaggca                                              20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
caccacggga agcaccggtc                                              20

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 195
ggagcctagg ggacagcggt t                                              21

<210> SEQ ID NO 196
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
cacggttggc cttagggttc ag                                             22

<210> SEQ ID NO 197
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tttttttttt tt                                                        12
```

HIGH RESOLUTION ANALYSIS OF MAMMALIAN TRANSCRIPTOME USING GENE POOL SPECIFIC PRIMERS

CROSS-REFERENCE TO RELATED APPLICATIONS

This application is a continuation of PCT Application No. PCT/US2012/042413 filed Jun. 14, 2012 which claims priority to U.S. Provisional Application Ser. No. 61/497,221, filed Jun. 15, 2011, the entire contents of which are incorporated by reference herewith.

STATEMENT REGARDING FEDERALLY SPONSORED RESEARCH

This invention was made with government support under grant no. HL087375 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jun. 13, 2012, is named 24978016.txt and is 45,273 bytes in size.

FIELD OF THE INVENTION

The present invention relates to materials and methods for analyzing mammalian transcriptomes, particularly with the use of high throughput technologies.

BACKGROUND OF THE INVENTION

Ultra-high throughput sequencing approaches, which has high sensitivity and a large dynamic range, has replaced standard microarray platforms for whole transcriptome analysis (Marioni et al. 2008; Asmann et al. 2009; Wang et al. 2009; Marguerat and Bahler 2010). Massive parallel sequencing of millions of transcripts allows digital estimation of gene abundance as opposed to only expression profiles obtained from microarrays, which are dependent upon the hybridization efficiency of probes to the transcripts. The fast evolution of sequencing technologies resulting in an increase of sequencing depth and the decline in cost per base sequenced has further reinforced their position as preferred platforms for mRNA expression analysis (Metzker 2010; Ozsolak and Milos 2011).

The most widely used RNA-seq protocol (Mortazavi et al. 2008) relies upon fragmentation of mRNA generating a library of uniformly distributed fragments of mRNA. This protocol requires large amounts of starting material (10-100 ng of mRNA) limiting its application in many fields such as in developmental biology, where it is impractical to get such large amounts. Furthermore, this protocol maintains the relative order of transcript expression resulting in poor representation of low abundance transcripts at current sequencing depths (Bloom et al. 2009; Fang and Cui 2011). Multireads and biases introduced by transcript length (Oshlack and Wakefield 2009) and random hexamer primer hybridization (Hansen et al. 2010) further restrict reliable quantitation of low abundance transcripts for large mammalian transcriptomes.

To address these limitations, a number of protocols have been developed. While "random priming" strategies (Li et al. 2008; Armour et al. 2009; Adli et al. 2010) amplify starting material (mRNA or cDNA) by exploiting hybridization and extension potential of hexamer/heptamer primers, they often result in low yield of good quality reads arising out of mis-hybridization of primers and primer dimerization. Also, the random priming methods do not discriminate regions of the transcriptome to amplify, specifically low abundance transcripts. This limitation is also seen in other uniform amplification strategies (Tang et al. 2009; Hoeijmakers et al. 2011). Another approach, involving targeted enrichment (Levin et al. 2009; Li et al. 2009; Zhang et al. 2009) requires longer sample preparation steps, larger amounts of RNA and high costs.

SUMMARY OF THE INVENTION

The present invention provides a sequencing-library generation system for low abundant transcripts, comprising at least three distinct phases comprising: a) phase I comprising a primer design strategy comprising a defined set of heptamer primers generated using an iterative randomized algorithm; b) phase II comprising a targeted amplification of said transcripts containing heptamer-primer binding sites using the defined set of heptamer primers; and c) phase III comprising an amplicon library comprising valid amplicons with correct orientation of distinct adapter fragments being phosphorylated at 5' end and ligated to an adapter for subsequent amplification and synthesis-based sequencing.

The present invention further provides a method of amplifying and sequencing low abundance transcripts, comprising: (a) designing and generating a set of heptamer primers using an iterative randomized algorithm; b) amplifying targeted transcripts containing heptamer-primer binding sites using the designed set of heptamer primers to form valid amplicons; c) preparing an amplicon library comprising said valid amplicon; d) selecting distinct adapter fragments with correct orientation; and e) phosphorylating at 5' end and ligating the selected adapter fragments of said transcripts for subsequent PCR amplification and synthesis-based sequencing.

In certain embodiments, the iterative randomized algorithm used for designing and generating the set of heptamer primers is presented in FIG. 5. Mammalian transcriptome possess thousands of heptamer primer-binding sites, however, only a small proportion of them are desired for the successful implementation of the strategy. In order to enrich for desired primer-binding sites, an iterative randomized algorithm was employed which identifies a defined set of heptamer primers, while exploring all possible primer-binding sites and assigning positive score to the desired primer-binding sites. Identification of the highest scoring primer set is NP hard and it remains sensitive to the first (seed) pair of primers included in the primer set. This could potentially draw the primer set to local maxima. In order to circumvent this, the algorithm generates user defined "n" primer sets with each primer set starting with different seed (primer pair). The algorithm begins with empty primer sets with two primers added to the primer set in each iteration. Next, score of the primer set is calculated based upon the user-defined scoring criterion. At the end of the iteration "n" primer sets are selected with a criterion mentioned in the flowchart (FIG. 5). The addition of the primers to the primer set is stopped if either of the following conditions are met:
  a) The primer set produces a "valid amplicon" for all desired genes.
  b) The number of primers in a primer set has reached 20.

Condition b) is required to avoid primer dimerization. If the primer set is unable to cover all desired genes then another primer set is generated for the genes not covered in the previous set.

In certain embodiments, the heptamer primer-binding sites on said transcripts comprises flanking unique regions and residing in open configuration. In certain embodiments, the designed set of heptamer primers bind directly upstream to said flanking unique regions on said transcripts. In certain embodiments, the designed set of heptamer primers comprises 44 heptamer primers listed in Table 5. These hepatamer primers are divided into three (3) groups to reduce primer-dimerization.

In certain embodiments, the valid amplicon comprises: a) a length between 50 and 300 bp; (b) both forward and reverse primer-binding sites are in open configuration; (c) at least of the primer-binding sites must have a $\Delta G \geq -2$ Kcal/mol; (d) a 32 unique region follow one of the primer binding sites; (e) a GC content does not exceed 58%; and (f) within 5 Kb of the 3' end.

The present invention further provides that the targeted amplification is optimized for heptamer hybridization while reducing mis-priming and primer dimerization, and use of the invention sequencing-library generation system and method for identifying key embryological lineage specific transcripts that anticipate differentiation of specific cell types.

The present invention thus provides a new approach and system to sequence tag generation, in which a defined set of gene pool specific heptamer primers are used to amplify target sequences on mammalian genes. The resulting amplicon library covers more than 90% of the mouse transcriptome, with more than 80% of annotated genes producing sequence tags that uniquely map to an mRNA database. The present invention contrasts to the random sequence tag generation, which results in a very low number of unique tags, and genes that are present in low abundance cannot be quantified with statistical significance. These lower abundance genes are often those involved in signal transduction or code for transcription factors and are often of more interest when investigating certain diseases.

In certain embodiments, the present invention designs, tests and refines the inventive sequence tag generation system, and further validates the uniqueness of the sequence tags and the subsequent genes mapped from them. The sequence tag generation system can be used on high or ultra high throughput sequencing platforms, such as Illumina's gene analyzer, and in multi-sample parallel applications. The present invention sequence tag generation system consists of software and novel primer sequences designed to hybridize to unique sequences identified in 74% of known genes and also designed to optimize amplification of target sequences that have low expression levels. The fragments produced are of sizes suitable for high throughput sequencing and cover more than 90% of the transcriptome.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 1: Schematic representation of sequencing library preparation using heptamer primers based amplification. FIG. 1 (a) discloses "TTTTTTTTTTTT" as SEQ ID NO: 197. FIG. 1(b) Expression profiles of genes responding to graded activation of Activin A/TGFβ signaling pathway in mouse embryoid body at day 4. The quantitative RT-PCR data was normalized with respect to untreated serum free media control. FIG. 1(c) Fidelity of amplification of cDNA library using heptamer primers. Fold changes observed in 11 genes (from part (b), Afp and Cer1) across different dosages of Activin A showed perfect agreement with quantitative RT-PCR performed on cDNA ($R^2$=0.94; n=45). FIG. 1(d) Distribution of reads on mouse genome.

FIG. 2: Reproducibility, Dynamic range and targeted amplification.

FIG. 3: Graded expression of putative target genes of Activin A/TGFβ signaling pathway in day 4 mESCs.

FIG. 4. Lineage segregation between neuro-ectoderm and PS (mesoderm and definitive endoderm) achieved by modulation of Activin A/TGFβ signaling pathway.

FIG. 6. Performance of heptamer primer amplification.

FIG. 7. PCR biases observed in the invention methodology.

DETAILED DESCRIPTION OF THE INVENTION

Figure 1A:
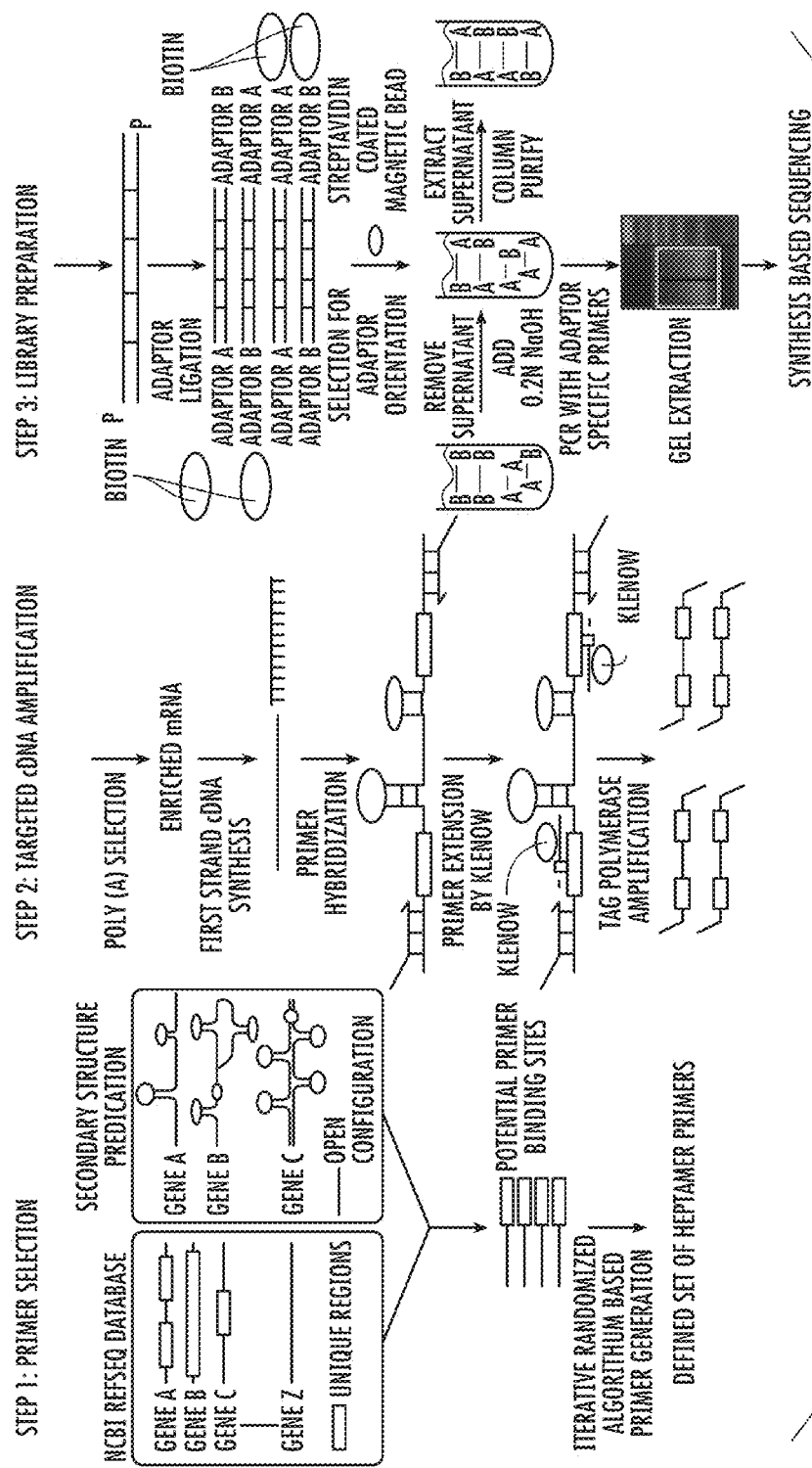
FIG. 1(a) Step 1: Primer selection was based on identifying potential primer binding sites that were less likely to form secondary structures and resided upstream to the unique regions on the mouse transcriptome. Step 2: targeted cDNA amplification. A Standard cDNA library was prepared the primers selected from step 1 were annealed to the single stranded cDNA library and were extended and amplified as indicated. Step 3: Library preparation. Illumina paired end adaptors were ligated to the ends of the amplicon library and correct orientation of adaptors were selected. The library was further amplified using Illumina's paired end adaptor primers and size selected for synthesis-based sequencing.

The present invention provides a novel strategy/approach for a sequencing-library generation system and method of use thereof for amplifying and sequencing particularly low abundance transcripts. This strategy, in which a defined set of gene pool specific heptamer primers are used to amplify target sequences on mammalian genes, was developed in response to questions with regard to, for example, whether mammalian transcriptomes possess regions with unique sequences that can serve as templates for amplification, whether there is a defined set of primers that can selectively amplify such regions, and whether a protocol could be developed that can be used to efficiently amplify such regions using a small set of primers.

The sequencing-library generation system of the present invention comprises at least three distinct phases: a) phase I comprising a primer design strategy comprising a defined set of heptamer primers generated using an iterative randomized algorithm; b) phase II comprising a targeted amplification of said transcripts containing heptamer-primer binding sites using the defined set of heptamer primers; and c) phase III comprising an amplicon library comprising valid amplicons with correct orientation of distinct adapter fragments being phosphorylated at 5' end and ligated to an adapter for subsequent amplification and synthesis-based sequencing. In certain embodiments, the iterative randomized algorithm used for designing and generating the set of heptamer primers is presented in FIG. 5. In certain embodiments, the designed set of heptamer primers generated using the iterative randomized algorithm are presented in Table 5.

The present invention further provides a method of amplifying and sequencing low abundance transcripts, comprising: (a) designing and generating a set of heptamer primers using an iterative randomized algorithm; b) amplifying targeted transcripts containing heptamer-primer binding sites using the designed set of heptamer primers to form valid amplicons; c) preparing an amplicon library comprising said valid amplicon; d) selecting distinct adapter fragments with correct orientation; and e) phosphorylating at 5' end and ligating the selected adapter fragments of said transcripts for subsequent PCR amplification and synthesis-based sequencing.

In certain embodiments, the present invention provides a novel quantitative cDNA expression profiling strategy, involving amplification of the majority of mouse transcriptome using a defined set of 44 heptamer primers listed in Table 5. The amplification protocol allows for efficient amplification of regions of interest from picograms of mRNA while minimizing mis-hybridization of primers and primer dimerization.

The inventors further implemented this strategy on embryological lineage segregation, achieved by graded activation of Activin A/TGFβ signaling in mouse embryonic stem cells (mESCs). The fold changes in transcript expression were in excellent agreement with quantitative RT-PCR and a dynamic range spanning more than five orders of magnitude in RNA concentration with a reliable estimation of low abundant transcripts. The transcriptome data identified key lineage markers, while the high sensitivity showed that novel lineage specific transcripts anticipate the differentiation of specific cell types.

The methods disclosed herein can be used to reliably analyze the mammalian transcriptome by employing ultra high throughput approaches such as the Illumina Genome Analyzer system (Illumina, Inc., San Diego, Calif.). The strategy uses gene pool specific heptamer primers to selectively amplify unique regions on mammalian genes. This ensures better representation and thus quantitation of known genes expressed at low to moderate levels with high statistical power, while utilizing much less starting material. In addition, the strategy provides a platform for analyzing multiple samples at the same time, thus reducing the operational cost.

EXAMPLES

Example 1

Quantitative Transcriptomics Using Designed Primer-Based Amplification

Quantification of low abundant transcripts from limited amounts of starting material has remained a challenge for RNA-seq at current sequencing depths. Here, the inventors describe an informatics-based strategy that uses a defined set of heptamer primers to amplify the majority of transcripts expressed at moderate to low levels while preserving their relative abundance. The strategy reproducibly yields high levels of amplification necessary for sequencing-library generation from low starting material and offers a dynamic range of over five orders of magnitude in RNA concentrations. The method shows potential for selective amplification of transcripts of interest enabling better quantitation and multiplexing for increased throughput and cost effectiveness. The applied this approach to study cell lineage segregation in embryonic stem cell cultures, which models early mammalian embryogenesis. The amplification strategy revealed novel sets of low abundance transcripts, some corresponding to the identity of cellular progeny before they arise, reflecting the specification of cell fate prior to actual germ layer segregation.

Sequencing-Library Generation Using Heptamer Primers Based Amplification

Figure 5:
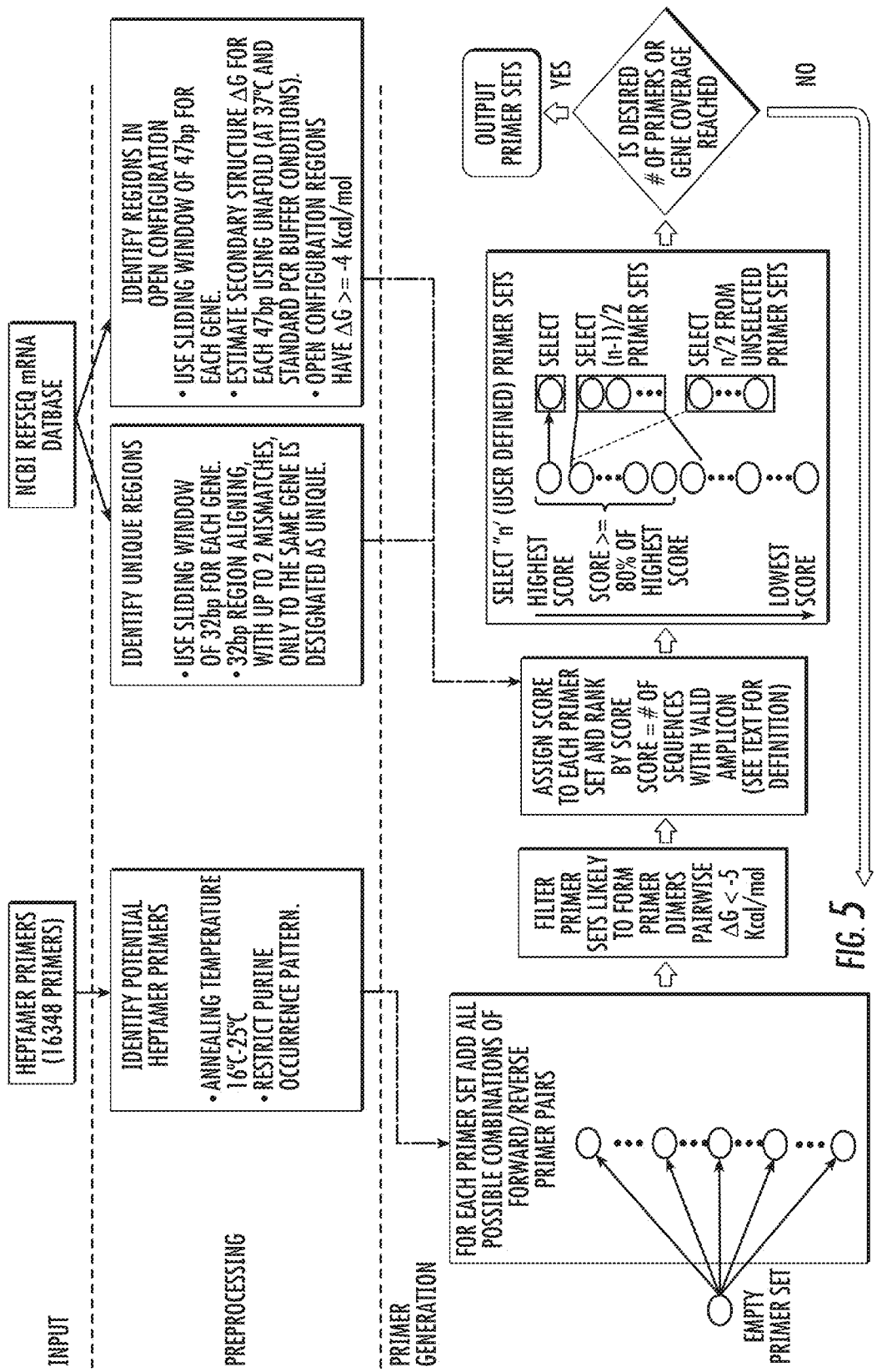
FIG. 5. Flowchart of heptamer primer generation using an iterative randomized algorithm.

A novel cDNA sequencing-library generation methodology was developed to reliably estimate relative abundance of transcripts using 10-50 picograms of mRNA. The methodology consisted of three distinct phases (FIG. 1A). In the first phase, the inventors developed a primer design strategy that identified a defined set of 44 heptamer primers amplifying >80% of the mouse transcriptome. This strategy incorporated known biases in PCR namely, secondary structure of primer-binding site in first stranded cDNA, GC content and proximity to the 3' end of the gene to identify potential primer-binding sites. Of the 16384 input sequences of heptamer primers, the inventors selected primers with annealing temperatures between 16-25° C. To minimize mis-priming, heptamer primers starting with adenines at 5' end and/or purine rich primers were filtered out. Heptamer primers were further screened for their primer-binding sites in the non-coding regions of the genome in comparison to the coding transcriptome. Vast majority of the mammalian genome is transcribed, however only a small fraction of it is translated to known proteins. Heptamer primers with higher proportions of primer-binding sites in non-coding regions were discarded to reduce representation of the non-coding regions of the mammalian genome in the sequencing library. Next, an iterative randomized algorithm was implemented to identify a small set of heptamer primers, which preferentially amplified unique regions of mouse genes (FIG. 5). The primers were split into multiple sets ensuring no two primers had mutual interaction energy (Gibb's free energy) greater than −5 kcal/mol in order to reduce primer dimerization. Of the 26566 known genes in the mouse NCBI RefSeq mRNA database, the instant heptamer primers covered 15072 (56.7%) genes uniquely.

In the second phase of the methodology, the inventors performed a targeted amplification of the mouse transcriptome using the defined set of heptamer primers. This phase consisted of two components; (i) determination of the minimum length of the primer required to achieve efficient amplification and (ii) optimization of the amplification protocol to extend and amplify partially hybridized primers. The inventors determined 14 bp ($T_m$~45° C.) as the optimal length of the primers required to efficiently amplify regions of interest in the mouse transcriptome. As such the heptamer primers were extended by addition of a universal 7 bp sequence derived from Illumina's adapter sequence at the 5' end of heptamer primers. Standard PCR protocols failed to amplify partially hybridized primers because of low annealing temperatures of the last 7 bp, resulting in significant distortions in the expression level of low abundance transcripts. This led to propose a novel protocol that uses a combination of mesophilic and thermophilic polymerases to efficiently amplify regions of interest on cDNA. The primers were first extended with Klenow (exo-) polymerase and later amplified by Taq polymerase (described in Methods).

In the last phase of the sequencing library generation, the amplicon library was 5' end phosphorylated and ligated to Illumina's adapters. Since only distinct adapter orientation fragments can be sequenced in Illumina's platform, the inventors used a biotin-streptavidin chemistry (described in Methods) to select correct orientations of adapters. The fragments were later PCR amplified using Illumina's adapter PCR primer and size selected for synthesis-based sequencing.

Evaluation of Heptamer Amplification Based Transcriptomics

The inventors implemented the methodology on an in-vitro cell culture based model of primitive streak (PS) induction in mESCs (Gadue et al. 2006; Willems and Leyns 2008). Signaling by the TGFβ-family member, Nodal through Activin receptor like kinase-4 is essential for mesoderm (Gurdon et al. 1994; Jones et al. 1995; Armes and Smith 1997) and endoderm (Tam et al. 2003; Sulzbacher et al. 2009) formation, and the dose-dependent induction of these tissues can be mimicked by treatment with Activin A. Various dosages of Activin A (3 ng/mL, AA3; 15 ng/mL, AA15; and 100 ng/mL, AA100) were therefore used to induce mesoderm and definitive endoderm while its inhibition by a small molecule inhibitor, SB-431542 (SB) (Inman et al. 2002), was used to induce neuro-ectoderm (Vallier et al. 2009b).

Small doses of Activin A substantially induced mesodermal markers (e.g., Kdr, Mesp1) while higher dosage of Activin A was required for induction of anterior tissues of the mouse embryo including definitive endoderm (e.g., Gsc, Foxa2) (FIG. 1B). Upon complete inhibition of Activin A/TGFβ signaling the inventors observed up-regulation of neuro-ectoderm markers (e.g., Sox1) (Pevny et al. 1998). The inventors also demonstrated dose dependent regulation of some of the direct target genes (e.g., Lefty1, Lefty2 and T also known as Brachyury) (Guzman-Ayala et al. 2009; Dahle et al. 2010) of the Activin A/TGFβ signaling pathway.

The differential expression of these low abundant genes showed excellent concordance with quantitative RT-PCR ($R^2$=0.94, FIG. 1C).

For a typical transcriptome measurement, ~30 million reads were obtained per lane of Illumina's flowcell (Table 1).

TABLE 1

Mapping Summary of sequencing experiment
The first 3 rows represent mapping to mouse mRNA refseq database. Reads that did not align to the mRNA RefSeq database where further mapped to mouse genome including mitochondria. Multireads refer to reads that mapped to more than one gene/genomic locations. Second row correspond to multireads that mapped exclusively to various isoforms of the same gene

|  | Lane 1 (SFM) | Lane 2 (SB) | Lane 3 (AA3) | Lane 4 (AA15_1) | Lane 6 (AA15_2) | Lane 7 (AA100) |
|---|---|---|---|---|---|---|
| Total reads | 33.4M | 35.2M | 32.8M | 29.4M | 25.1M | 30.0M |
| Unique reads (mRNA Refseq) | 58.20% | 56.80% | 59.20% | 59.10% | 59.50% | 58.20% |
| Multireads (Isoform group only, mRNA Refseq) | 13.52% | 13.37% | 13.45% | 13.20% | 13.19% | 13.05% |
| Multireads (mRNA refseq) | 5.47% | 5.63% | 5.45% | 6.20% | 5.71% | 5.45% |
| Genomic (Unique) | 12.16% | 13.33% | 10.63% | 10.76% | 11.01% | 12.16% |
| Genomic (Multireads) | 2.10% | 2.12% | 1.98% | 1.98% | 2.03% | 2.09% |
| Genomic and Mitochondria | 2.49% | 3.51% | 4.52% | 4.41% | 3.92% | 4.52% |
| Mitochondria (Unique) | 0.59% | 0.64% | 1.06% | 0.74% | 0.75% | 0.84% |
| Unmappable | 5.38% | 4.44% | 3.61% | 3.47% | 3.73% | 3.59% |
| Genes (Unique reads >=10) | 11792 | 11565 | 11508 | 11409 | 11097 | 11401 |
| Genes (Multireads >=10) | 6401 | 6293 | 6329 | 6265 | 6167 | 6215 |
| Binding Sites (Unique reads >=10) | 126844 | 125775 | 117587 | 110069 | 96060 | 109109 |

About 59% (18 million) reads uniquely mapped to more than 11000 transcripts with ≥10 reads. About 19% of the reads were non-uniquely mapped with vast majority of them mapping to isoform groups. Another 18% of the reads (71% uniquely) mapped to genomic locations (excluding the open reading frames of known transcripts) and mitochondria transcripts (FIG. 1B). Of these genomic reads, 72% mapped to intronic regions of genes while another 20% mapped within 5 Kb of the known transcripts. The presence of these reads could imply the existence of partially processed nuclear RNAs (pre-mRNA) that still have their introns intact and/or non-coding RNA. Since the inventors did not see a strong correlation between the fold changes in intronic reads with those from proximal exons, these reads may arose from non-coding RNA transcripts.

Figure 6C:
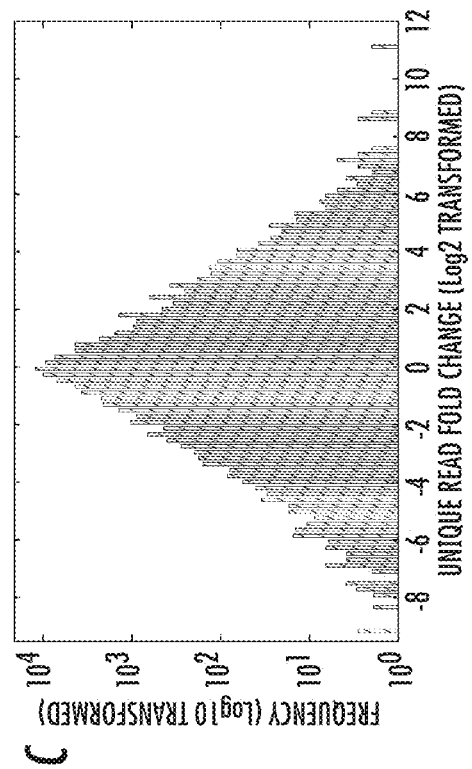
FIG. 6(c) Distribution of fold changes observed in unique reads of the genes across all the samples. The majority of the genes were not differentially regulated. The invention methodology captured fold changes in range of $2^{-8}$-$2^{10}$ demonstrating broad dynamic range.
Figure 6D:
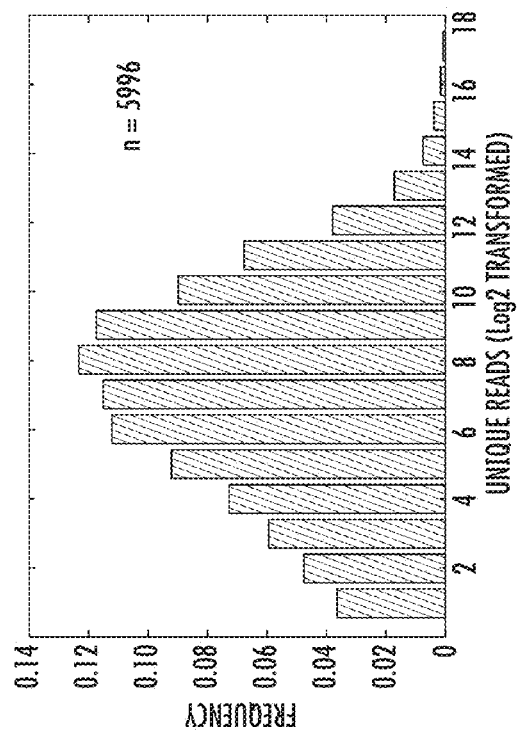
FIG. 6(d) Distribution of uniquely mapped reads for low abundant genes in Activin A (15 ng/mL) sample. Microarray data was used to compile a list of ~6000 genes expressing >20 fold less than β-actin. Majority of these genes had high number of mapped reads facilitated reliable estimation of their abundance.
Figure 6A:
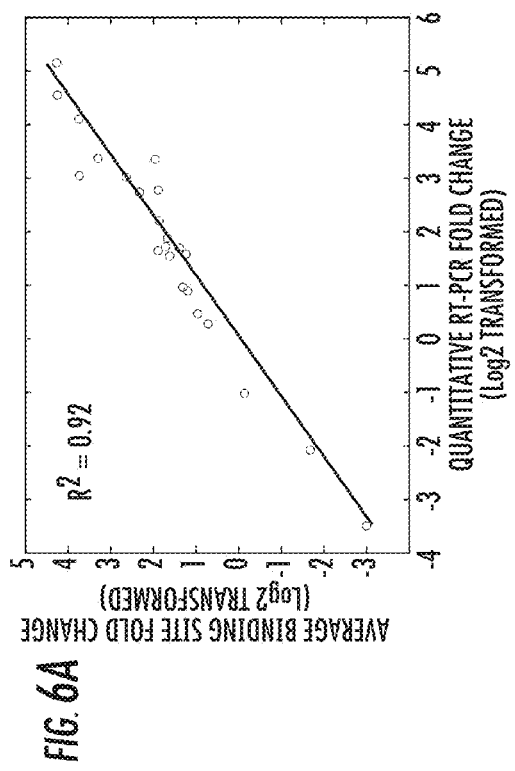
FIG. 6(a) Multiple heptamer primer-binding sites on a gene provided independent measurements of relative abundance of the gene. The average fold change obtained from multiple primer-binding sites was in concordance with quantitative RT-PCR ($R^2$=0.92, n=24).

The experimental data indicated expression of more than 100,000 different primer-binding sites representing ~18,000 known genes. This demonstrates the scale of massive multiplexing achieved by our methodology. Expression of ~10 different primer-binding sites for each gene was obtained. Notably, each site provided an independent measurement of relative abundance serving as technical replicates for the experiment (FIG. 6A).

Figure 6B:
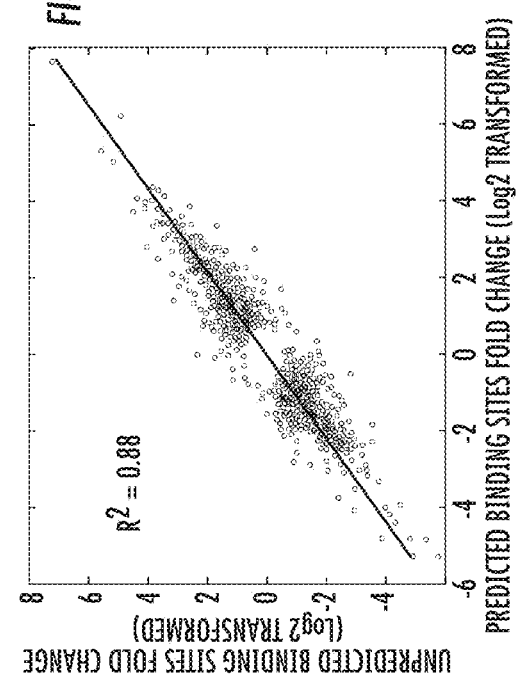
FIG. 6(b) Mis-primed PCT products maintained relative abundance of gene expression. Fold changes observed in predicted vs. mis-primed binding sites for differentially expressed gene (in SB-43542 vs. AA100) showed strong correlation ($R^2$=0.88).
Figure 7A:
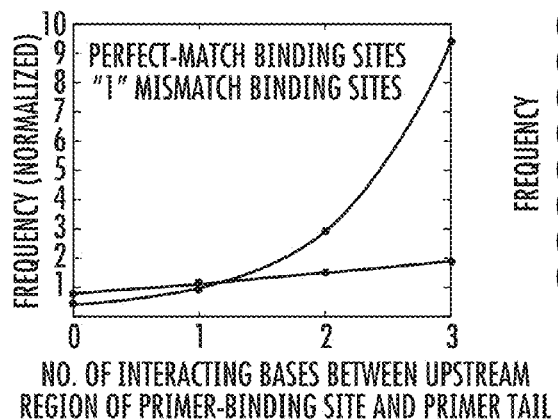
FIG. 7(a) Tail Interaction. Heptamer primer binding sites with '1' mismatch had significantly higher tail interaction as compared to perfectly matched primer-binding site.

More than 50% of the uniquely mapped reads came from perfectly matched primer-binding sites while the rest were the product of mis-priming or single nucleotide polymorphisms (SNPs) in the primer-binding site. Fold changes observed in predicted and mis-primed binding sites were highly correlated ($R^2$=0.88) suggesting that mis-primed PCR products were able to conserve the relative abundance of transcripts (FIG. 6B). Mis-primed products were mainly stabilized by a favorable interaction between the last three bases of universal tail of the heptamer primers (5'-ATA-3') and upstream regions of primer-binding sites (tail interaction, FIG. 7A). The inventors also noticed an inherent amplification bias towards shorter fragments that has been reported earlier in multiplexed PCR strategies (Zajac et al. 2009). Finally, the inventors observed no indication of primer-dimerization.

Figure 2C:
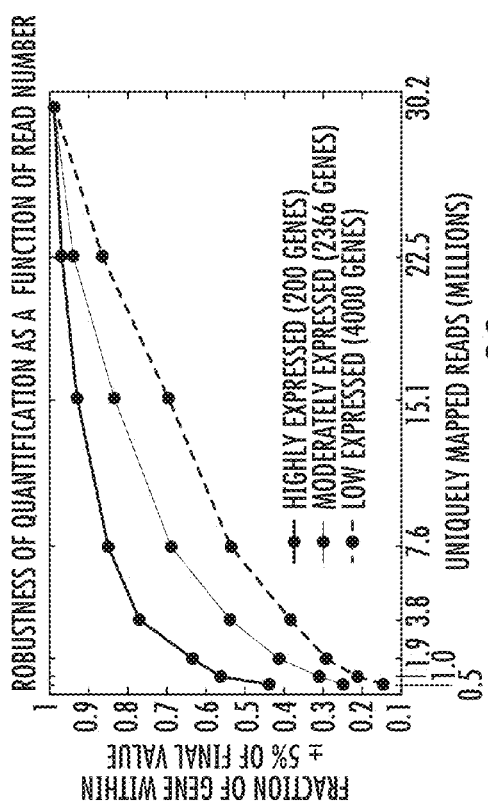
FIG. 2(c) Robustness of unique reads measurements as a function of transcript expression levels and depth of sequencing. Microarray data obtained for Activin A (15 ng/mL) dosage was used to characterize transcripts into different levels of expression. Uniquely mapped reads were successively reduced by factor of two and number of transcripts within ±5% of final value was determined. More than 50% low abundance transcripts were accurately predicted for as few as 8 million uniquely mapped reads.
Figure 2D:
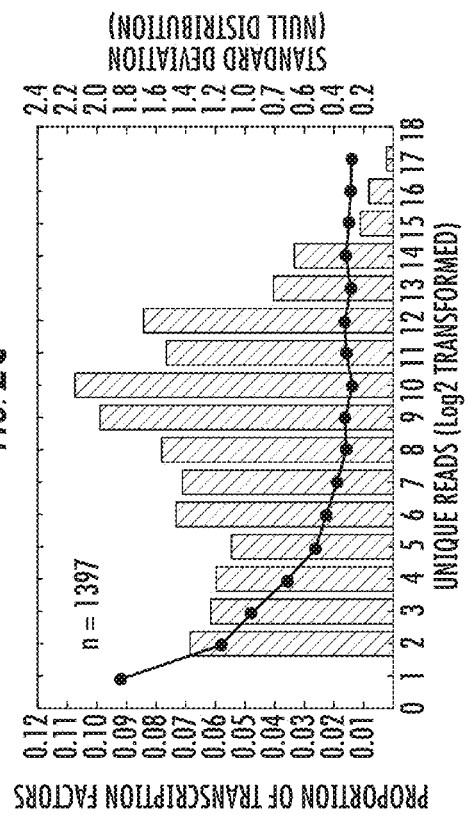
FIG. 2(d) Targeted amplification of low expressed transcription factors. Blue bars represents distribution of unique reads mapping to known mouse transcription factors (n=1397) for Activin A (15 ng/mL) dosage. The black curve represents the standard deviation in fold change observed in null distribution as a function of average reads (between technical replicates). Majority of the transcription factors had high unique reads with small standard deviation resulting in better estimation of relative abundance.
Figure 2A:
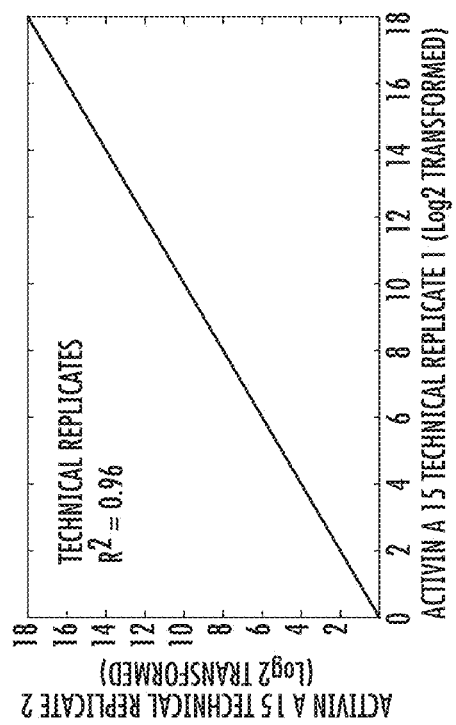
FIG. 2(a) Comparison of two Activin A 15 dosage replicates ($R^2$=0.96).
Figure 2B:
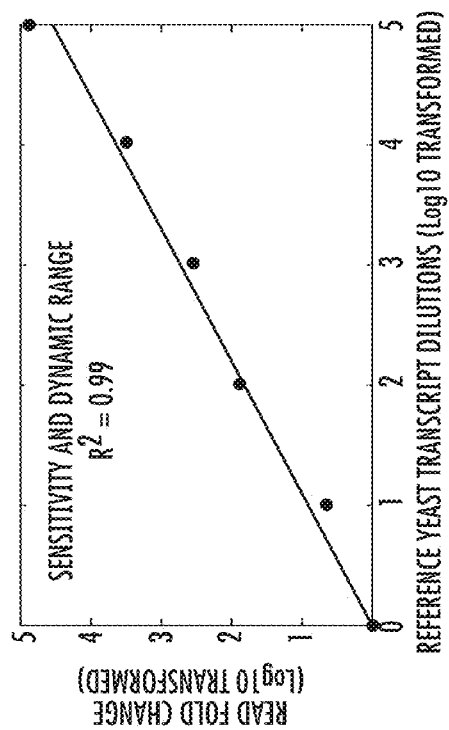
FIG. 2(b) Six in-vitro synthesized transcripts derived from yeast POT1 promoter of length 180 bp were added to untreated control cDNA at varying concentration of six orders of magnitude. The reads obtained from the transcripts revealed a fold change of upto $10^5$ ($R^2$=0.99) in comparison to the lowest abundant transcript.

Analysis of the technical replicates revealed a strong correlation in quantitative transcript expression ($R^2$=0.96, FIG. 2A). To assess the dynamic range, the inventors spiked the untreated control (serum free media, SFM) with six artificial transcripts of the yeast POT1 promoter (~180 bp). The transcripts were flanked with different heptamer binding sites spanning six orders of magnitude in RNA concentration. The second most abundant transcript was similar in expression with β-actin abundance in the biological samples. The primers were able to effectively amplify all the six transcripts and maintained their relative abundance ($R^2$=0.99, FIG. 2B). The distribution of fold changes (FIG. 6C) observed in all possible pairwise comparisons of the samples was broad ($2^{-8}$-$2^{10}$) suggesting a much higher dynamic range in comparison to microarray platforms (few hundred folds) (Wang et al. 2009).

To determine the robustness in measurements of transcript expression, the inventors determined the number of transcripts within ±5% of the final expression as a function of uniquely mapped reads (FIG. 2C). The inventors classified transcripts into different expression categories (high, moderate and low) based on their expression observed in the gene expression profiling using standard microarray platform. More than 50% of the low abundant transcripts were accurately quantified with 7 million uniquely mapped reads (reduction by a factor of 4).

Figure 7B:
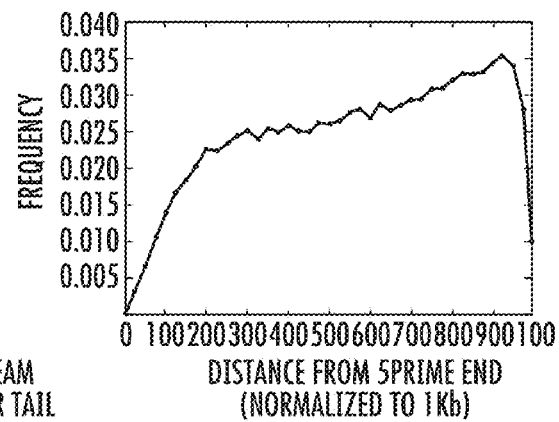
FIG. 7(b) PCR bias caused by propensity of heptamer primer-binding sites to form stable secondary structure (Gibbs free energy, ΔG). The distribution is shifted towards high ΔG implying that primer-binding sites forming stable secondary structure shielded primers from annealing to their target sequences.

The inventors observed that the protocol preferentially amplified primer-binding sites flanked by sequences that interacted with the primer tails (FIG. 7A) and/or contained unstable local secondary structure (FIG. 7B). These PCR biases were utilized to re-order the transcript detection level ranking within a sample resulting in high unique reads for low abundance transcripts and consequently better estimation of their relative abundance. To validate this approach, the inventors considered the expression profiles of low abundance mRNAs encoding transcription factors. The frequency distribution of unique reads was broad with the majority being detected with low noise (FIG. 2D).

Graded Activation of the Activin a/TGFβ Signaling Pathway in mESCs

Figures 3A, 3C:
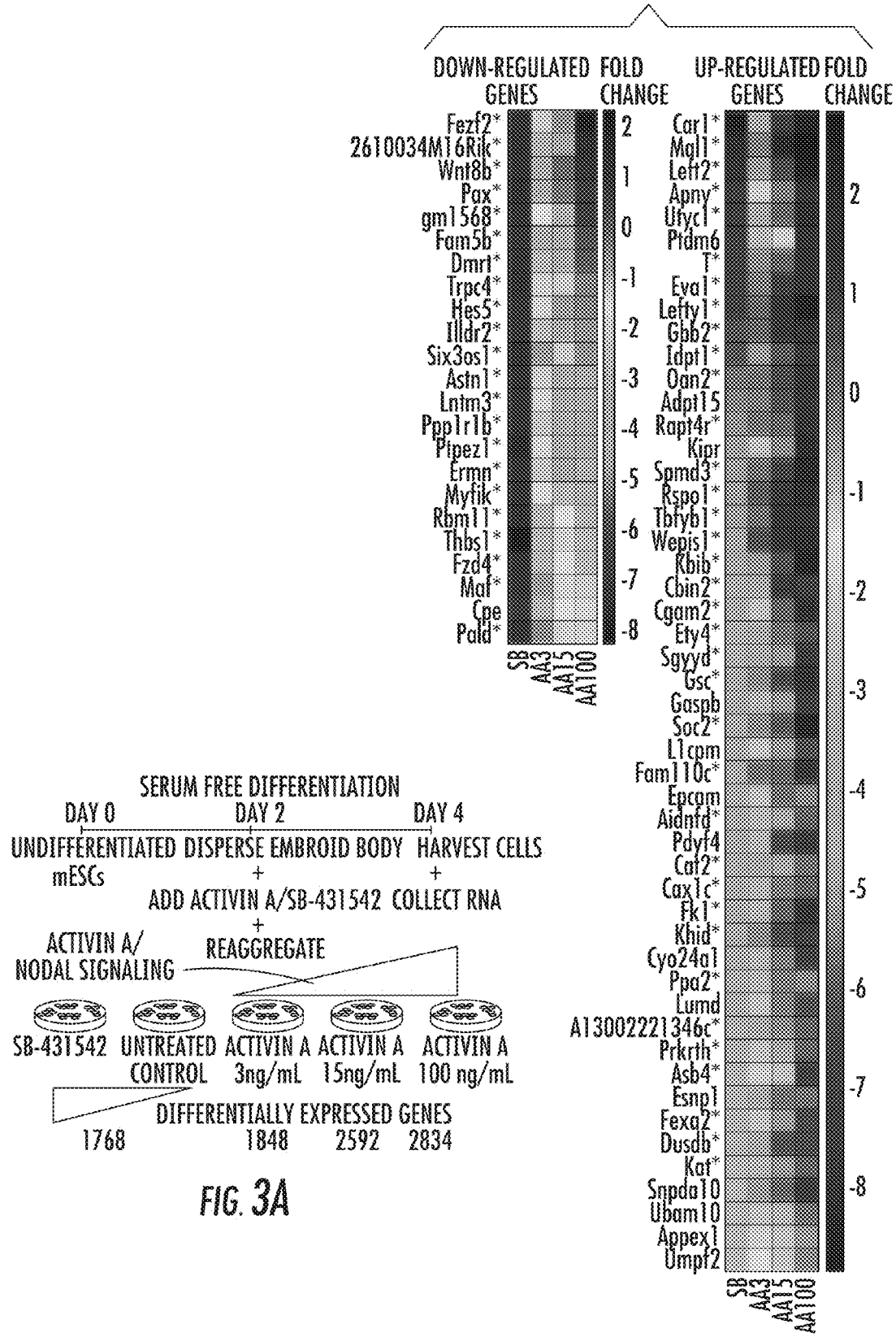
FIG. 3(a) Schematic representation of the experimental setup. Mouse ESCs were differentiated in serum free conditions and different dosages of Activin A and SB-431542 were introduced to create a graded activation of Activin A/TGFβ signaling pathway. Cells were harvested at day 4 for sequencing-library generation. Differential gene expression analysis identified ~15-20% of expressed transcripts as differentially regulated in each sample in comparison with untreated control (supplementary methods).
FIG. 3(c) Putative TGFβ target genes in differentiating mESCs at day 4. The heatmap corresponds to fold changes observed for genes in comparison to untreated control. Putative target genes were classified as genes that followed opposite trends of regulation upon treatment with Activin A and SB. 50 genes were successively up-regulated while 23 genes followed graded down-regulation with increasing dosages of Activin A. Majority of the TGFβ target genes (marked with *) had FoxH1 transcription factor binding sites separated by 30-200 bp (also called ASE) in 10 Kb upstream and downstream of the transcription start site. Known TGFβ target genes are highlighted in bold.
Figure 3B:
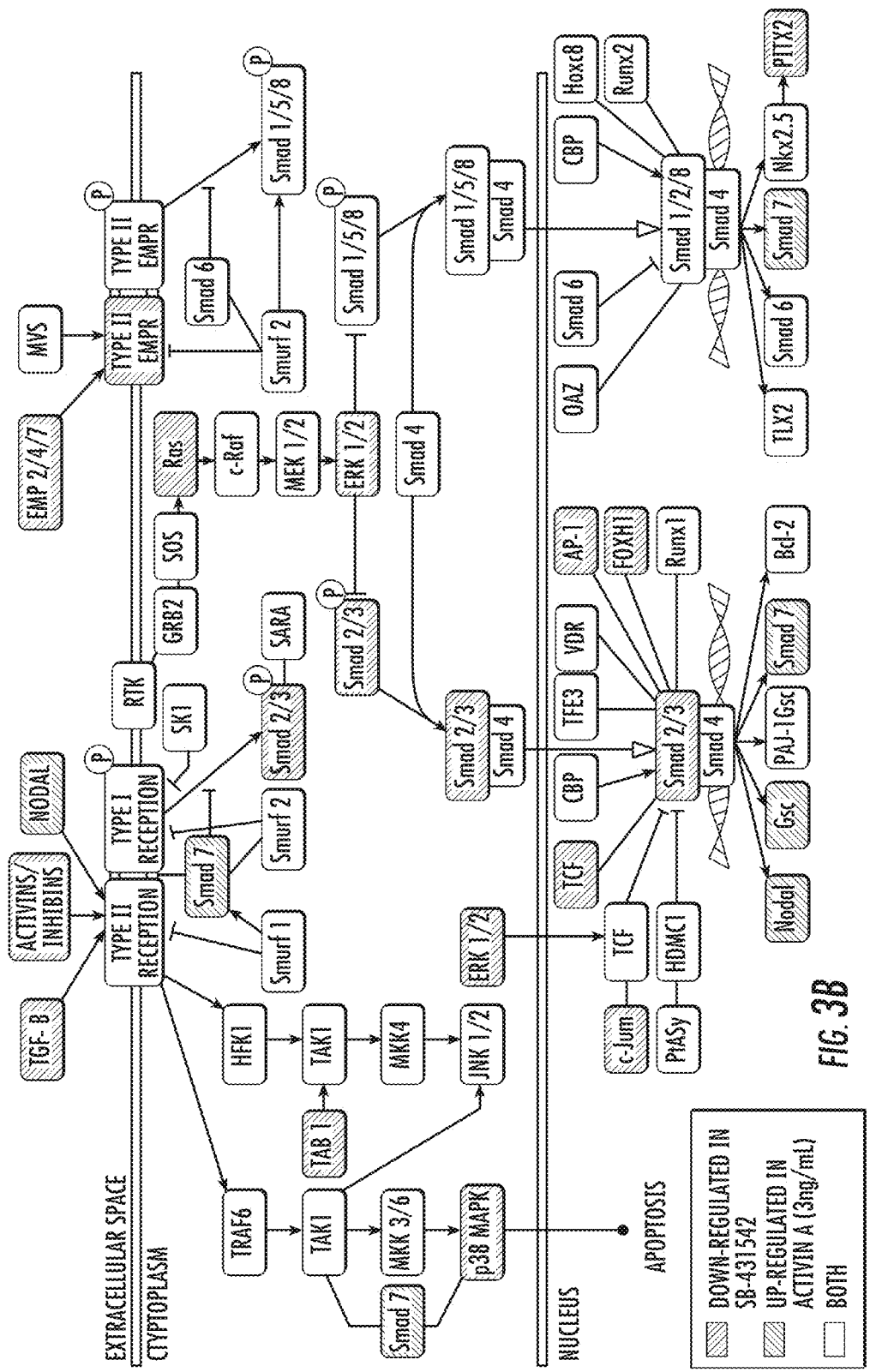
FIG. 3(b) Regulation of Activin A/TGFβ signaling pathway in response to SB-431542 and Activin A.

Mouse ESCs were differentiated in serum free conditions in presence of varying dosages of Activin A and SB for two days and the mRNA was profiled at day 4 (equivalent to 6.5-7.5 dpc) using the instant methodology (FIG. 3A, see methods). Differential gene expression analysis revealed a stepwise increase in the number of transcripts differentially regulated as differentiating mESCs responded to the gradient of Activin A. The most transcriptional diversity was observed between SB and AA100 samples corresponding to two extreme states of pathway activation. By mapping those transcripts to known Activin A/TGFβ pathway components using Ingenuity pathway analysis (Ingenuity® Systems), substantial down-regulation of many of these genes was observed in response to pathway inhibition via SB (FIG. 3B) whereas Activin A up-regulated these genes by activation of the TGFβ pathway.

Graded activation of Activin A/TGFβ signaling pathway allowed to identify putative TGFβ regulated genes during early differentiation of mESCs (FIG. 3C). Potential TGFβ target genes were based on (i) opposing modulation in SB and AA3 conditions (in comparison to untreated control) and (ii) subsequent up-regulation with higher dosages of Activin A. The inventors identified many of the expected TGFβ target genes, including Cer1 (Katoh 2006), Lefty1 (Guzman-Ayala et al. 2009), Lefty2 (Guzman-Ayala et al. 2009), Foxa2 (Zhang et al. 2011) and T (Dahle et al. 2010) (FIG. 3C, bold). Not all expected genes were found because they either did not meet the stringent criteria (Nodal (Dahle et al. 2010), Nanog (Vallier et al. 2009a)) or they were not expressed in this cellular context.

More importantly, the inventors have identified transcripts that respond similarly to the graded Activin A/TGFβ pathway modulation, but have not been linked previously to the pathway. Promoter analysis of these transcripts revealed the presence of multiple FoxH1 binding sites (Labbe et al. 1998; Shiratori et al. 2001; Norris et al. 2002) (Asymmetric Elements, ASE) within 10 Kb upstream and downstream of transcription start site supporting our hypothesis that the Activin A/TGFβ signaling pathway regulates the expression of these transcripts.

Lineage Segregation is Achieved by Regulation of Activin A/TGFβ Signaling

Figure 8:
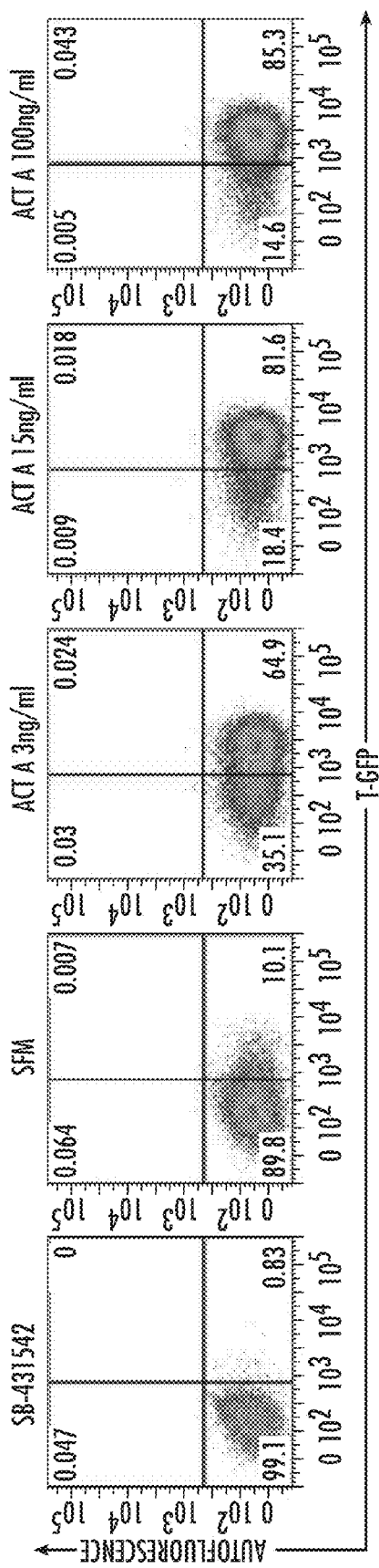
FIG. 8. Flow cytometry on T-GFP mESCs at day 4 of differentiation upon treatment with SB and Activin A. Graded activation of Activin A/TGFβ signaling pathway led to increased expression of mesoderm marker, T.

The preliminary experiments with T-GFP mESCs (GFP driven by Brachyury/T promoter) showed negligible induction of GFP cells at day 4 of differentiation upon treatment with SB (described in the Methods). The untreated control condition (SFM) naturally drives mESCs to neuro-ectoderm lineage with only 5-10% GFP+ cells. However, in presence of mesoderm inducing factors such as Activin A (3 ng/mL), >60% of the cells were GFP demonstrating efficient induction of mesoderm (FIG. 8). Neuro-ectoderm associated transcripts were classified as transcripts significantly up-regulated in SB and SFM in comparison to AA15 (Table 2A) and comprised of known neuro-ectoderm markers (Sox1, Sox2 and Pax6, FIG. 4A). The inventors then performed GO term (biological process annotation) enrichment and KEGG pathway enrichment to validate the classification. Biological processes associated with neuron differentiation and morphogenesis (Table 3) were enriched in the transcript list while the Wnt and Activin A/TGFβ pathway were significantly represented (Table 4).

Figure 4A:
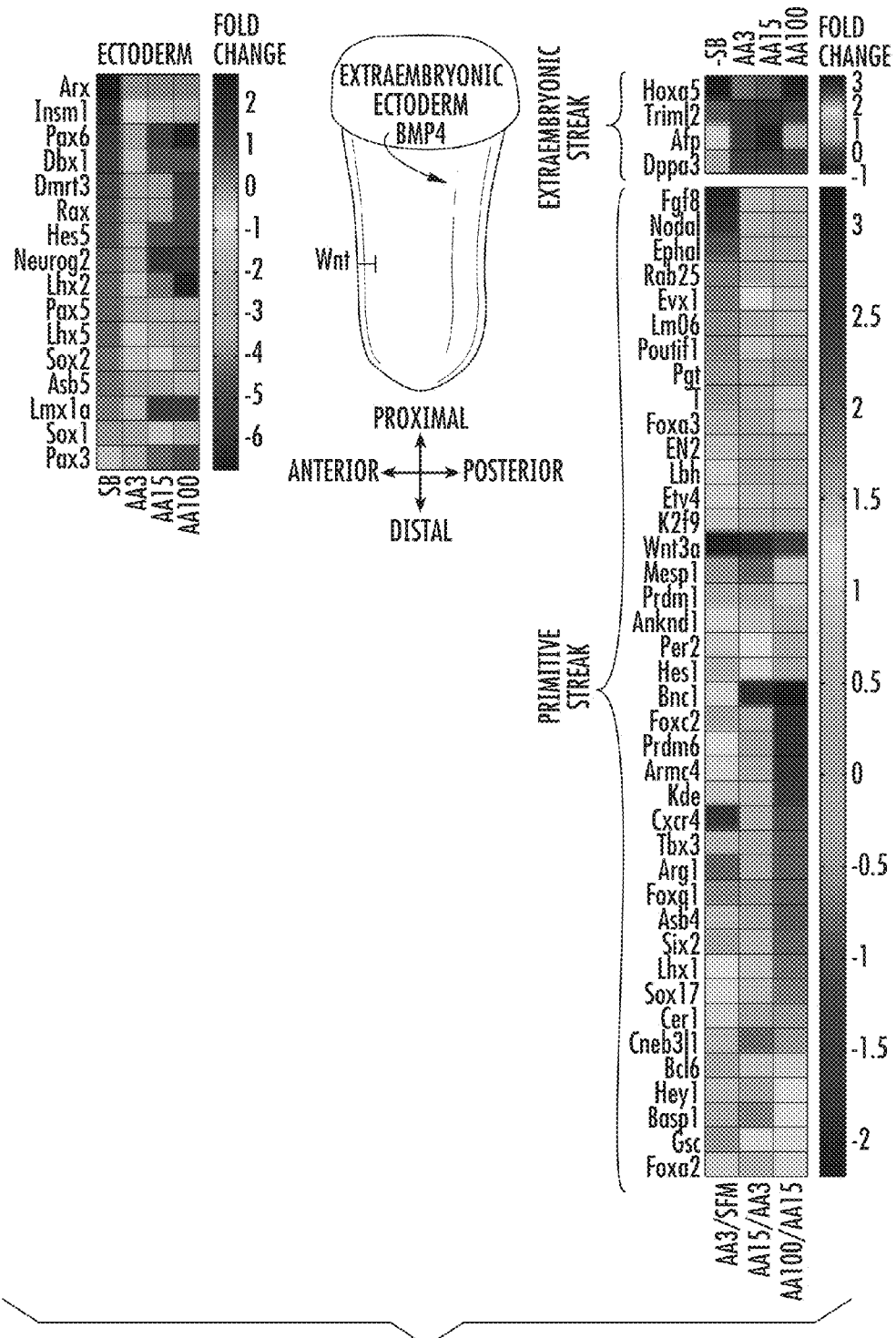
FIG. 4(a) Schematic of mouse embryo at embryonic day 6.5-7.5 with gradient of Nodal expression (yellow) with the maximum expression observed in the anterior tissue. Inhibition of TGFβ signaling pathway commit cells to neuro-ectoderm lineage (blue). A heatmap of the neuro-ectoderm associated genes is depicted (left of the embryo) with their fold changes in different samples in comparison to untreated control. The heatmap on the right of the embryo depicts successive fold changes of the PS markers with varying dosages of the Activin A. The genes with highest fold change in AA100 in comparison with AA15 are enriched for definitive endoderm and other anterior tissue markers. Other PS genes are expected to have diffused expression pattern all throughout the streak. Genes with known expression in Theiler Stage 9-11 of mouse embryo are highlighted in bold (MGI database).
Figure 4B:
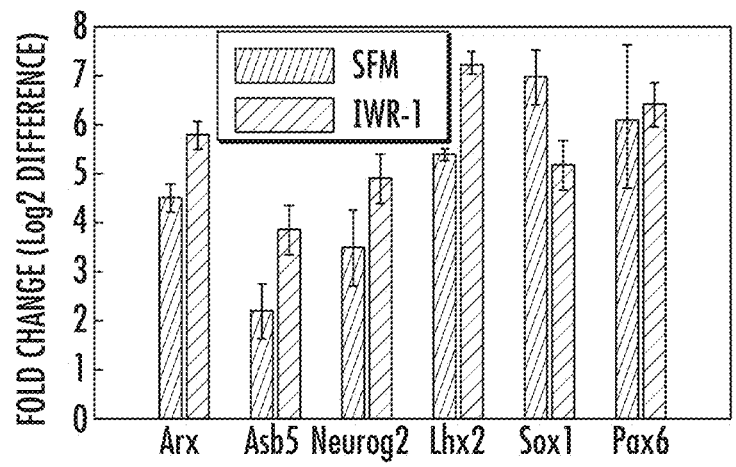
FIG. 4(b) Small molecule inhibition of Wnt signaling pathway (IWR-1) induced neuro-ectoderm lineage. The fold changes are normalized to Activin A 3 ng/mL dosage.
Figure 9A:
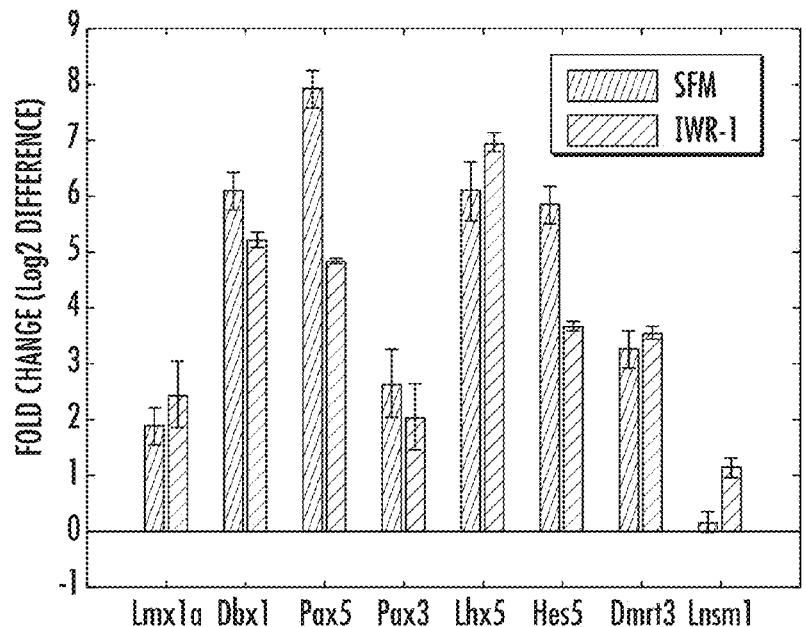
FIG. 9 (a) Validation of neuro-ectoderm specific genes by using small molecule inhibitor of Wnt Signaling pathway, IWR-1 to efficiently induce neuro-ectoderm in an in-vitro differentiation model. The quantitative RT-PCR fold changes were normalized to Activin A (3 ng/mL) dosage. Error bars represent standard deviation in biological replicates (n=3). Asterisks indicates p>0.05 (Student's t-test) compared with controls.
FIG. 9(b) Expression profiles of Primitive Streak markers in response to BMP4 signaling. Quantitative RT-PCR fold changes for two BMP4 dosages (3.5 and 12 ng/mL) were normalized with respect to Activin A alone induction. Error bars represent standard deviation in biological replicates (n=3). Asterisks indicate p>0.05 (Student's t-test) compared with controls.

To correlate some of the novel neuro-ectodermal transcripts with embryology, the inventors searched the MGI gene expression database for the expression patterns of the identified transcripts throughout all stages of mouse embryonic development. Expressions of the vast majority of the neuro-ectoderm associated transcripts were not reported in embryonic day 6.5-7.5 embryos, the stages that correspond to the studied mESC derived samples. A number of these genes, however, were expressed in neuro-ectoderm derivatives at later stages of development. To validate the early expression of these transcripts in the neuro-ectoderm lineage, the inventors used Wnt pathway inhibition (IWR-1) (Chen et al. 2009) as an alternative to induce neuro-ectoderm and confirmed the up-regulation of a number of these neuro-ectoderm associated transcripts in samples enriched for neurogenic progenitors (FIG. 4B and FIG. 9A).

On the other hand, genes significantly up-regulated in AA15 in comparison to SB and SFM were designated as PS associated transcripts (Table 2B). The list included a number of known mesoderm and endoderm markers (T, Mesp1, Foxa2 and Sox17). GO enrichment analysis revealed biological processes associated with gastrulation, tissue morphogenesis and tube development (Tables 3 and 4).

Figure 4C:
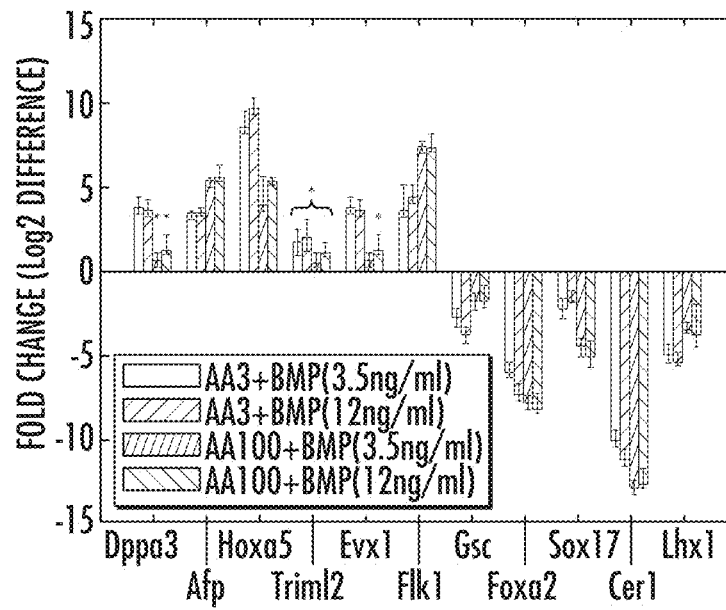
FIG. 4(c) BMP4 enhanced expression of posterior and extraembryonic mesoderm markers at the expense of anterior markers. Quantitative RT-PCR fold changes for two BMP4 dosages are normalized with respect to Activin A alone induction. Error bars represent standard deviation in biological replicates (n=3). Asterisks indicates p>0.05 (Student's t test) compared with controls.
Figure 9B:
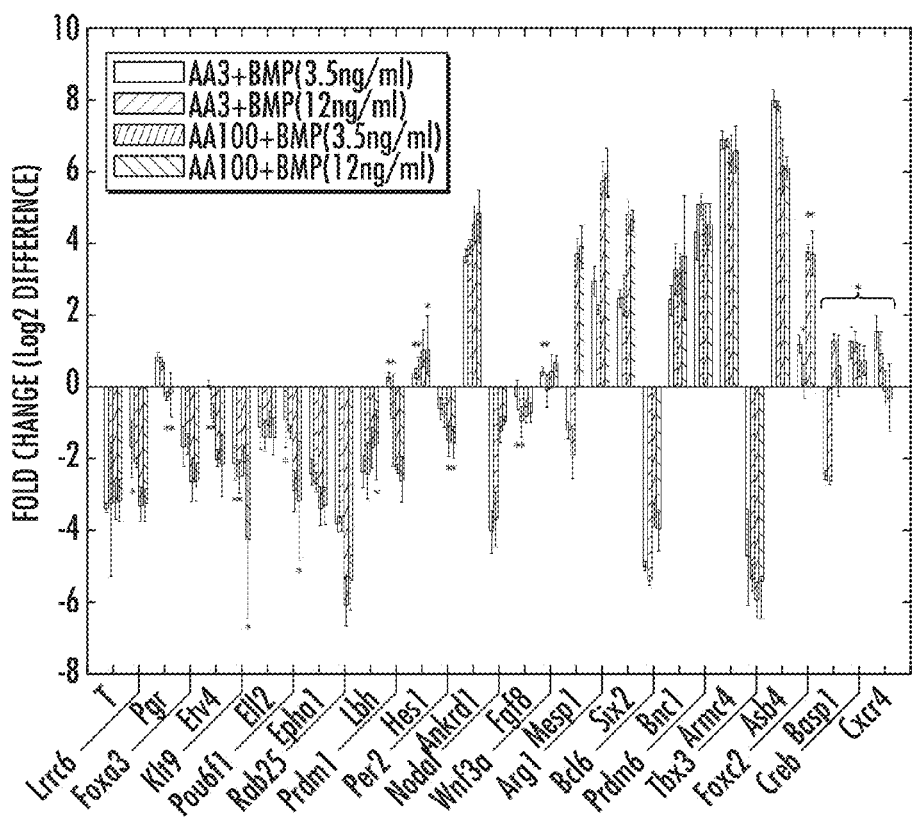

Graded Activin A/TGFβ signaling has been shown to induce different mesoderm and endoderm tissues, correlating with anteroposterior position of progenitors within the PS, with the highest levels of signaling corresponding to anteriormost located progenitors (Hoodless et al. 2001; Yamamoto et al. 2001; Rossant and Tam 2009). Therefore, transcripts demonstrating maximum fold change between AA100 and AA15 in comparison to other two fold changes (AA3/SFM and AA15/AA3) can mark anterior PS derivatives. A number of definitive endoderm markers were in accordance with this classification. Conversely, the majority of the transcripts with maximum fold changes in AA3/SFM and AA15/AA3 have diffused expression throughout the PS (FIG. 4A). A number of transcripts were shown to have diffused expression via in-situ hybridization (Faust et al. 1995). To further validate this classification, mesoderm were posteriorized by treating with BMP4 (Kishigami and Mishina 2005; Nostro et al. 2008; Kattman et al. 2011) in combination with Activin A. Transcripts known to be expressed in extraembryonic mesoderm and the extreme posterior of the PS were enriched upon treatment with BMP4 while the expression of anterior transcripts were significantly down-regulated (FIG. 4C). PS transcripts with diffused expression also exhibited down-regulation in BMP4 treated samples suggesting a dominant posteriorization effect of BMP4 signaling (FIG. 9B).

DISCUSSION

Sequencing library generation from low amount of starting material has remained a challenge for most of the existing RNA-seq protocols. Random priming strategies amplify from low amount of RNA, however, reliable quantitation of low abundant transcripts is not regularly obtained. In the initial experiments with random priming strategy (Li et al. 2008), primer-dimerization and mismatches in the primer-binding sites resulted in majority of the reads mapping to multiple mRNA species. Only 18% of the reads mapped uniquely to the transcriptome and low abundant transcripts were significantly under-represented because of poor dynamic range. The instant designed-primer method addressed these issues and provides the first means to increase sensitivity of RNA-seq so that the expression of low abundance transcripts can be reliably measured. Since low abundance transcripts often encode key regulatory proteins and are modulated in response to developmental, physiological and/or pathological stimuli, this technology greatly increases the applicability of RNA-seq for monitoring normal and disease related processes.

Figure 10A:
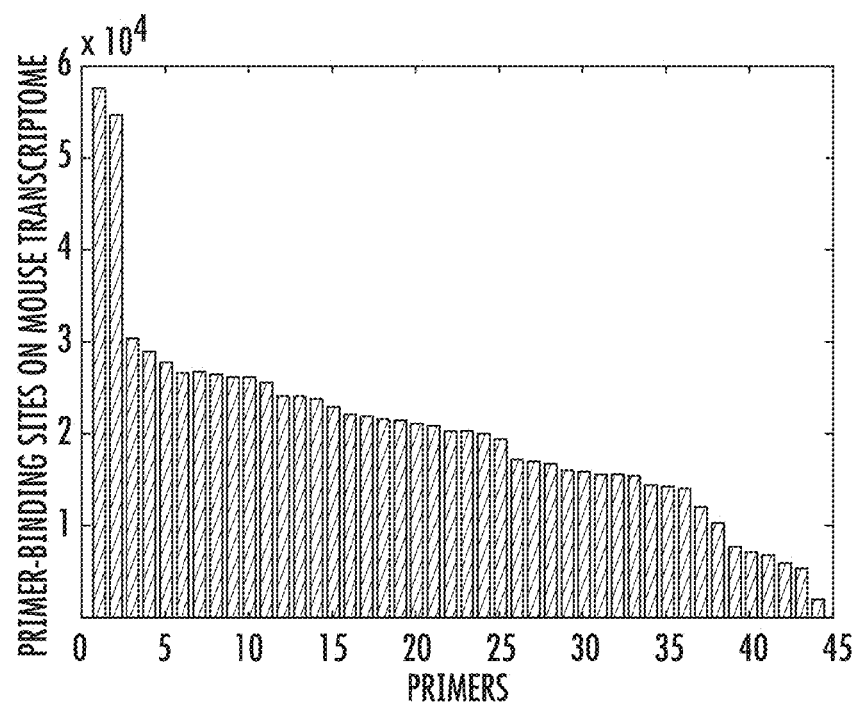
FIG. 10(a) Distribution of heptamer primer-binding sites on mouse transcriptome.

Primer designing was a critical component of the instant methodology. The ubiquitous presence of heptamer primer-binding sites on the mouse transcriptome was utilized to amplify more than 80% of known transcripts (FIG. 10A) from a small set of 44 heptamer primers. The inventors optimized PCR conditions for heptamer hybridization to achieve successful amplification of more than 50,000 different fragments representing ~18,000 genes in the mouse Refseq mRNA database. A number of considerations were made while determining the base composition of primers to reduce mis-priming and primer dimerization. As a result, majority of the reads (55%) came from perfect binding of the primers while another 38% had one mismatch in primer-binding site. This enabled to use the entire read length for alignment to the mouse transcriptome.

Theoretical assessment revealed the existence of ~61% of unique 32-mer sequences (with two mismatches) in mouse transcriptome. The inventors designed primers to bind directly upstream to the unique regions on the transcripts. As a result, ~64% of the expressed transcripts were uniquely covered. A vast majority of the multireads mapped exclusively to isoforms. However, 20% of expressed isoforms had uniquely mapped reads enabling their quantification. This strategy of targeted amplification of known transcripts inherently limits the capability to evaluate uncharacterized transcripts and RNA structure and is thus best suited for quantification of characterized transcripts.

The transcriptome data demonstrated excellent reproducibility and sensitivity. The inventors were able to reliably estimate up to $2^{16}$ fold change in transcript expression from picograms of mRNA. Furthermore, fold changes observed in low abundant transcripts were in perfect agreement with quantitative RT-PCR. The inventors exploited PCR biases, arising out of tail interaction and secondary structure formed by single stranded cDNA, constructively, to perform targeted amplification of low abundance transcripts. As a result, the relative expression pattern of the transcripts within a sample was distorted leading to a broad distribution of unique reads for low abundance transcripts (FIG. 6D). Consequently, the inventors were able to reliably estimate expression of majority of these transcripts.

A lineage segregation model achieved by graded activation of the Activin A/TGFβ signaling pathway was implemented in mESCs to study whether a genome-wide transcriptome analysis can provide segregation to a particular lineage. Previously, several studies have identified key players regulating the activation of this pathway that served as markers for this study. The sequencing data obtained was highly quantitative and competent to measure differential gene expression even for the low abundant transcripts. The quantitation coincided with the expected pattern based on the previous studies for all key lineage markers, thus validating the approach. Using graded activation of the Activin A/TGFβ pathway the inventors identified novel target genes in day 4 mouse embryoid bodies. The inventors also showed that modulating two other key regulators of early cell fate, Wnt and BMP4, would alter the expression of these transcripts by quantitative RT-PCR, supporting their involvement in germ layer segregation. Unexpectedly, the transcriptome data revealed early expression of a number of lineage specific transcripts whose expression has not been studied at such early stages of lineage diversification, suggesting that lineage specification at the genetic level occurs earlier than previously anticipated.

Typical RNA-seq protocols do not discriminate against high abundant transcripts. Consequently, most of the sequencing effort is spent on a small number of highly abundant transcripts (~75% of mapped reads represented only 7% of known transcriptome) (Labaj et al. 2011). The instant strategy shows potential for preferential amplification of regions of interest on the mammalian transcriptome. A detailed model on sequence properties of the heptamer primer-binding sites and its hybridization potential would facilitate researchers to design primers to selectively amplify a small set of genes targeting pathways (e.g., differentiation related pathways) or a phenotype (e.g., pluripotency of ESCs) and eliminate highly expressed transcripts such as ribosomal genes. Given that only few genes are being targeted, multiple samples could be analyzed in the same experiment, thus bringing cost effectiveness and acquiring more replicates for a more reliable statistical analysis. Apart from differential gene expression analysis, the instant strategy can also be utilized to sequence regions associated with disease related mutations thus providing a basis for diagnosis.

Materials and Methods
Primer Design

Heptamer primer-binding sites are ubiquitously present in mouse transcriptome enabling a selection of small set of primers to cover more than 80% of the mouse transcriptome. Moreover, while hexamer primers have low range of annealing temperatures, heptamer primers exhibit optimal hybridization efficiency towards transcripts allowing for efficient amplification.

Suffix array data structure was implemented to identify 32-mer unique regions in mouse transcriptome. All suffixes in the suffix array were divided into disjoint segments using 32-mer sequences. For each segment, all related segments with up to 2 mismatches were identified. If the segment and all of its related segments contained suffixes coming from only one transcript, then the segment was designated as unique. Next, local secondary structure of the known genes as stable secondary structures were expected to shield heptamer primers from hybridizing to the primer-binding site. For each gene in Mouse NCBI RefSeq mRNA database, a window of 47 bp was run along the gene length and its propensity to form stable secondary structure was determined using UNAfold software (Markham and Zuker 2008). Gibbs free energy of interaction ($\Delta G$) was calculated at 37° C. for standard PCR buffer conditions (2 mM $MgCl_2$ and 50 mM NaCl). Regions with $\Delta G \geq -4$ kcal/mol were considered to be available for heptamer primer hybridization (open configuration).

All heptamer primer-binding sites were identified, including (i) flanking unique regions on mouse transcriptome and (ii) residing in open configuration. An iterative randomized algorithm (FIG. 5) was then implemented to identify a defined set of heptamer primers forming valid amplicons for >80% of mouse transcriptome. a valid amplicon was defined as follows:
 1. It has a length between 50 and 300 bp.
 2. Both, forward and reverse primer-binding sites are in open configuration.
 3. At least one of the primer-binding sites must have a $\Delta G \geq -2$ Kcal/mol.
 4. A 32 bp unique region should follow one of the primer binding sites.
 5. The GC content of the amplicon should not exceed 58%.
 6. The amplicon must be within 5 Kb of the 3' end.

Using this approach, 44 unique primers were identified, which were split into 3 sets to reduce primer-dimerization (Table 5). This configuration covered ~80% of transcripts with 57% of transcripts covered uniquely. More than 170000 valid amplicons were predicted from 201242 primer-binding sites.

Targeted cDNA Amplification with Heptamer Primers
cDNA Preparation

Figure 7C:
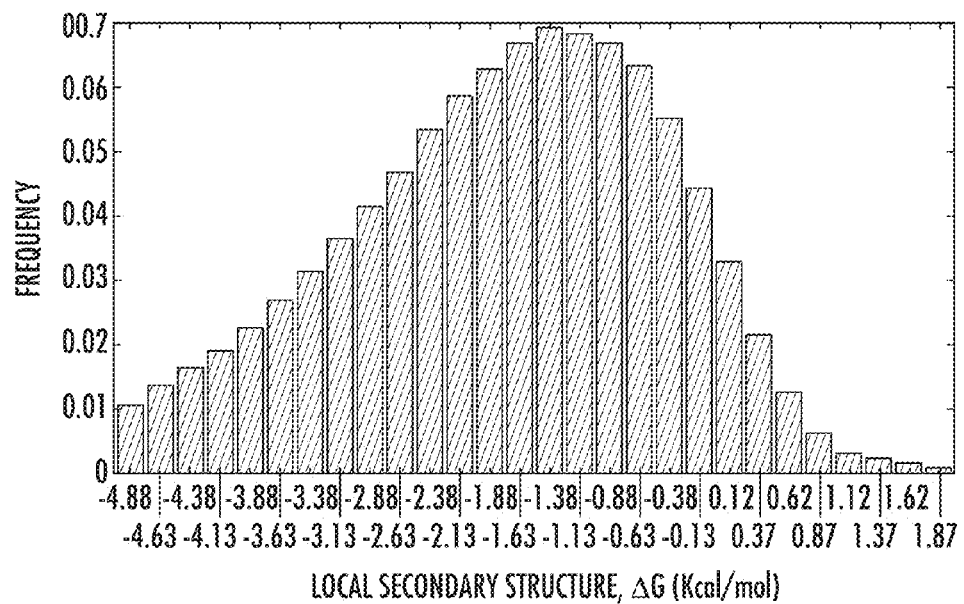
FIG. 7(c) PCR bias caused by reverse transcriptase. Majority of the primer-binding sites came from 3' end of the genes mainly because of the inability of the reverse transcriptase to produce full-length first strand cDNA.

Total RNA was extracted from harvested cells using Trizol (Invitrogen). About 1 ug of total RNA was later subjected to Oligo(dT) selection using Oligotex mRNA mini kit (Qiagen) according to the manufacturer's protocol. First strand cDNA was synthesized with oligo dT (20-mer) primers using QuantiTect reverse transcription kit (Qiagen) according to manufacturer's protocol. QuantiTect reverse transcriptase shows potential to produce full-length cDNA (as long as 10 Kb). However, our transcriptome showed bias towards 3' end of the genes (FIG. 7C). Treatment with gDNA wipeout buffer degraded residual genomic DNA contamination. The reaction was column purified using the MinElute reaction cleanup kit (Qiagen) and eluted in 30 ul of elution buffer (EB).

Primer Hybridization and Extension

Heptamer primer hybridization and extension was achieved by using Klenow (exo-) polymerase, a mesophilic polymerase with strand displacement capability. Exo-nuclease deficient version of Klenow polymerase was used to avoid degradation of heptamer primers. First, 1 µl of cDNA (estimated 10-50 pg) was incubated with 1 µl of heptamer primer mix (200 µM stock for each primer), 1 µl of Taq polymerase buffer (10×) supplemented with 2.5 mM $MgCl_2$, 4% DMSO and 0.2 mM dNTP (10 mM stock) at 95° C. for 5 mins. The total reaction volume was kept at 9 µl. Mishybridization was minimized by ramping down the temperature of reaction mix to 37° C. at the rate of −0.2° C./sec. Later 1 unit of Klenow polymerase (exo-) was added to the reaction mix and incubated for 30 mins at 37° C. The enzyme was later heat inactivated at 85° C. for 15 mins. Klenow polymerase retained most of its activity in Taq polymerase buffer and its extension rate was not affected at 2.5 mM $MgCl_2$ concentration, as reported earlier (Zhao and Guan 2010).

Taq Polymerase Amplification

Taq polymerase possesses optimal affinity for DNA ($K_m$~2 nM) allowing efficient amplification of the PCR products while avoiding primer dimerization. Moreover, Taq polymerase allowed the addition of tail dATP at the 3' end of most of the amplicons thus eliminating this step from sequencing-library generation. A reaction master mix was prepared containing: 2 µl of Taq reaction buffer (10×), 1.25 mM of $MgCl_2$, Buffer Q (Qiagen), 2 µl of primer mix (2 µM stock), 0.2 mM of dNTPs (10 mM stock) and 2 units of Taq polymerase. DNase free water was later added to top up the reaction mix to 20 µl. Similar master mix was prepared for other primer sets. The reaction mix was added to the klenow reaction (30 µl of total volume) and a 14-cycle amplification was performed consisting of denaturation (95° C. for 30 s), annealing (46° C. for 30 s) and elongation (72° C. for 40 s).

Library Preparation
End Repair

The majority of PCR products formed by Taq polymerase have a dATP overhang at 3' end. The PCR products were purified using the Agencourt AMPure XP system (Beckman Coulter) according to manufacturer's protocol and eluted in 44 µl of elution buffer. Next, the 5' ends of the PCR products were phosphorylated using T4 Polynucleotide Kinase enzyme (NEB) in the presence of T4 DNA Ligase buffer containing ATP. The products were again purified using Agencourt AMPure XP system and eluted in 20 µl of elution buffer.

Ligation

Custom adaptor oligos were ordered in 100 µM concentration (Valuegene Inc.) with following modifications:

a) Adaptor_A_F (SEQ ID NO: 1)
5'-BiotinAATGATACGGCGACCACCGAGATCTACACTCTTTCCCTACACGACGCTCT-S-T-3'
(-S- represents Phosphorothioate Modification; 5' end of the oligo is biotinylated)

-continued b) Adaptor_A_R (SEQ ID NO: 2)
5'-Phospho-AGAGCGTCGTGTAGGGAAAGAGTGTAGATCTCGGTGGTCGCCGTATCATT-3'
(5' end of the oligo is phosphorylated)

c) Adaptor_B_F (SEQ ID NO: 3)
5'-CAAGCAGAAGACGGCATACGAGATCGGTCTCGGCATTCCTGCTGAACCGCTCT-S-T-3' d) Adaptor_B_R (SEQ ID NO: 4)
5'-PhosphoAGAGCGGTTCAGCAGGAATGCCGAGACCGATCTCGTATGCCGTCTTCTGCTTG-3'

Adaptor oligos referring to adaptor A (a, b) and adaptor B (c, d) were mixed in equimolar concentrations and diluted to 2 µM final concentration. Both adaptors were later denatured at 95° C. for 5 mins and then brought back to room temperature gradually at −0.2° C./s. This allowed hybridization of the two oligos of the adaptor with 'T' overhang. The adaptor mix was further diluted 1:10 to yield a stock concentration of 200 nM. The Ligation reaction was set up with 6 µl of PCR product, 1 µl each of adaptor A and B, 1 µl of T4 DNA Ligase buffer and 1 µl of T4 DNA Ligase. The reaction was performed at room temperature for 1 hr or at 16° C. overnight.

Selection of Adaptor Orientation

Ligation reaction resulted in fragments with either two identical (A-A and B-B) or two distinct (A-B and B-A) adapter orientations. However, only distinct adapter orientation fragments can be sequenced in Illumina's platform. The desired ligation products were enriched by utilizing the biotin (adaptor A)—streptavidin chemistry. Streptavidin coated magnetic beads (Dynabeads MyOne Streptavidin C1, Invitrogen) were used to pull down A-A, A-B and B-A ligation products using manufacturer's protocol. The supernatant, containing B-B, was discarded. Later, 0.2 N NaOH was added to the beads. Incubation for 10 mins at room temperature denatured two strands of the ligation product. Only A'-B strand appeared in the supernatant while both strands of the A-A remained associated with the beads. The supernatant with distinct orientation was extracted and column purified using MinElute PCR cleanup kit (Qiagen). The pH of the supernatant was adjusted to allow maximal binding to the column. The single stranded DNA was later eluted in 36 µl of EB.

Final PCR and Size Selection

The single stranded DNA obtained from previous step was amplified using adaptor specific primers. Following primers were ordered in 100 uM concentration:

a) Final_FP:

(SEQ ID NO: 5)
5'-AATGATACGGCGACCACCGAGATCTACACTCTTTCCCTACACGACGCTCTTCCGAATA-3' b) Final_RP:

(SEQ ID NO: 6)
5'-CAAGCAGAAGACGGCATACGAGATCGGTCTCGGCATTCCTGCTGAACCGCTCTTCCGATA-3'

A 50 µl PCR reaction was set up with 18 µl of single stranded template, 5 µl of primers (2 µM stock), 4% DMSO, 5 µl Pfu Turbo reaction buffer (10×), 0.2 mM dNTP (10 mM stock), 2.5 units of Pfu Turbo Polymerase. The amplification consisted of 14-15 cycles of denaturation (95° C.—30 s), annealing (62° C.—30 s) and extension (72° C.—40 s).

The amplified product was run in 2% agarose gel or 10% non-denaturing SDS-PAGE gel at 80-100 volts for 1.5 hrs. Using 50 bp ladder (NEB) a band corresponding to size range of 150-500 bp was cut out. The DNA was retrieved from the gel using QIAquick gel extraction kit (Qiagen) and submitted for synthesis-based sequencing.

Oligonucleotides

All of the heptamer primers were flanked by universal adapter sequence (5'-CCGAATA-heptamer-3' (SEQ ID NO:7)) and synthesized by Valuegene Inc. These primers were desalted and suspended in RNase/DNase free water to 100 µM concentration. Later the primers were pooled together at equimolar concentration of 2 µM.

Mouse Embryonic Stem Cell Culture and Differentiation

Mouse R1 or T-GFP embryonic stem cells were cultured on mouse embryonic fibroblast (MEF) on gelatin-coated dishes in high glucose DMEM (Hyclone, Logan, Utah) supplemented with 10% fetal calf serum (FCS) (Hyclone, Logan, Utah), 0.1 mM b-mercaptoethanol (GIBCO), 1% non-essential amino acids (GIBCO), 2 mM L-glutamine (Sigma, St. Louis, Mo.), sodium pyruvate (Sigma), antibiotics (Sigma), and 1,000 U/ml of LIF (Sigma) and passaged with 0.25% Trypsin (GIBCO).

For embryoid body (EB) differentiation, MEF were stripped from the cultures by 15 minutes incubations on gelatin-coated dishes. mESCs were collected and washed in PBS to remove traces of serum. mESCs were differentiated in serum free media containing N2 and B27 supplements as described elsewhere (Gadue et al. 2006; Willems and Leyns 2008). mESCs were aggregated at 50,000 cells/ml in non-coated polystyrene plates. After 2 days, EBs were dissociated by trypsin treatment and re-aggregated in fresh media in presence of different growth factors and small molecules. Activin A and BMP4 were obtained from R&D Systems while SB-431542 was obtained from Sigma. IWR-1 was synthesized in house as described previously (Chen et al. 2009). EBs were harvested at day 4 for RNA extraction and processing.

Data Analysis

Mapping Reads

The libraries were sequenced on Illumina's GIIx Analyzer platform. Single end 36 sequencing cycles were performed on version 5.0 of flowcell (FC-104-5001|TruSeq SBS Kit v5-GA (36-cycle)). The raw reads were truncated as 32-mer with the first and last 2 base pairs of the reads removed. The 32-mer reads were aligned to the RefSeq mRNA database allowing up to 2 mismatches. Bowtie (Langmead 2010) was used to align the reads. Reads that did not align with mouse RefSeq mRNA database were later aligned to mouse genome.

Differential Gene Expression Analysis

Figure 10B:
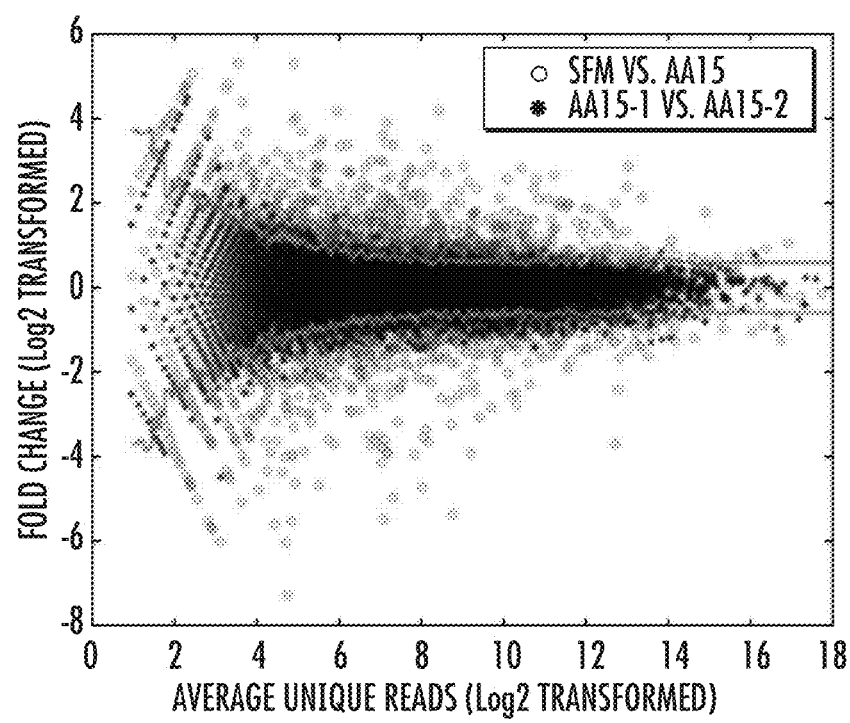
FIG. 10(b) Identification of differentially expressed genes. Baselines distribution was determined from MA plot of technical replicates. Experimental MA plot of untreated controls v. Activin A (15 ng/mL) was overlaid on top of baseline distribution. The blue curve represents p-value threshold of 0.05 and experimental ratios above/below the curve were designated as differentially regulated.

For each gene unique reads coming from predicted and non-predicted binding sites were combined in all samples. The reads for control and treatment, including technical replicates, were normalized using lowess normalization. Baseline distribution (null distribution) were determined by plotting M and A quantities for technical replicates, which are defined as:

$$M_{i,j} = \text{Log}_2\left(\frac{\text{Reads, }i}{\text{Reads, }j}\right)$$

$$A_{i,j} = 0.5 \times \text{Log2}(\text{Reads},_i \times \text{Reads},_j)$$

where 'i' and 'j' represents any two samples. M corresponds to log ratio in unique reads for a transcript between samples 'i' and 'j' while A corresponds to average reads for the gene in the two samples. No differentially expressed transcripts were expected between technical replicates. The noise in the null distribution reflected the variability arising out of sample preparation and sequencing platform. To quantify noise, we pooled ~100 genes in null distribution with similar reads and calculated standard deviation in fold change. We assumed that the noise in gene expression is a function of average gene expression and all genes with similar gene expression follow same noise. Also, the distribution of fold change was assumed to follow Gaussian distribution. Next, a threshold for differentially expressed genes was determined as 1.96 times of the standard deviation corresponding to less than 5% chance of gene being called differentially expressed by random chance. The experimental MA plot, which was defined as treatment/control, was overlaid on technical replicate MA plot and any gene representing fold change above/below the threshold was designated as differentially expressed (FIG. 10B).

Reverse Transcription and Quantitative RT-PCR (qPCR)

Total RNA was extracted from cells using Trizol (Invitrogen) according to the manufacturer's instructions. About 1 µg of total RNA was treated for DNA removal and converted into first strand cDNA using Quantitect Reverse Transcription kit (Qiagen). SYBR Green qPCR was run on a LightCycler 480 (Roche) using the LightCycler 480 SYBR Green Master Kit (Roche). All primers were designed with a $T_m$ of 60° C. Data was analyzed using the $\Delta\Delta C_t$ method, using β-actin as normalization control, which was determined as a valid reference in mouse ESC differentiation. The primer sequences are listed in Table 6, attached herein at the end of the specification.

Flow Cytometry

Day 4 embryoid bodies from T-GFP mESC were dissociated with trypsin to single cell suspensions and analyzed on a FACSCanto (BD Biosciences). Prior to analysis, cells were stained with propidium iodide to label dead cells. Data analysis was performed using FlowJo (Treestar Inc.) where measured events were gated for PI negative populations (exclusion of dead cells) and forward/side scatter (exclusion of debris and aggregates) before generating dot plots.

TABLE 2A

Neuroectoderm associated Genes

| REFSEQ | NAME | REFSEQ | NAME | REFSEQ | NAME |
|---|---|---|---|---|---|
| NM_010104 | EDNL | NM_010132 | EMX2 | NM_144955 | NKX6-1 |
| NM_172399 | A930038C07RIK | NM_009022 | ALDHLA2 | NM_153196 | RBKS |
| NM_175499 | SLITRK6 | NM_001003672 | PCDHAC2 | NM_001114385 | CHRDLL |
| NM_133643 | EDARADD | NM_001081134 | KCNGL | NM_009152 | SEMA3A |
| NM_009718 | NEUROG2 | NM_007666 | CDH6 | NM_016984 | TRPC4 |
| NM_007492 | ARX | NM_008900 | POU3F3 | NM_023279 | TUBB3 |
| NM_013627 | PAX6 | NM_007699 | CHRM4 | NM_001164785 | ADAMTS20 |
| NM_011720 | WNT8B | NM_172778 | MAOB | NM_028687 | 4930403N07RIK |
| NM_028462 | FEZFL | NR_027826 | 2610017L09RIK | NM_028116 | PYGOL |
| NM_011377 | SIM2 | NM_008746 | NTRK3 | NM_177368 | TMTC2 |
| NM_025681 | LIXL | NR_027891 | 2900092D14RIK | NM_011994 | ABCD2 |
| NM_027001 | 2610034M16RIK | NM_016889 | INSML | NM_008553 | ASCLL |
| NM_033652 | LMXLA | NM_001033351 | GRIN3A | NM_020278 | LGIL |
| NR_033490 | 2610100L16RIK | NM_031884 | ABCG5 | NM_011381 | SIX3 |
| NM_021279 | WNTL | NM_008782 | PAX5 | NM_177838 | FAML63A |
| NM_080433 | FEZF2 | NM_029569 | ASB5 | NM_021432 | NAPLL5 |
| NM_010419 | HES5 | NM_177034 | APBAL | NM_008237 | HES3 |
| NM_010151 | NR2FL | NM_008781 | PAX3 | NR_033259 | GML5070 |
| NM_145741 | GDFLO | NM_001081072 | SLC27A6 | NM_008590 | MEST |
| NM_001005232 | DBXL | NM_016708 | NPY5R | NM_178638 | TMEML08 |
| NM_001008423 | GML568 | NM_001142965 | 6430704M03RIK | NM_007586 | CALB2 |
| NM_029972 | ERMN | NM_011215 | PTPRN2 | NM_010572 | IRS4 |
| NM_001164528 | ILDR2 | NM_139300 | MYLK | NM_009199 | SLCLAL |
| NM_173367 | CYPT3 | NM_181753 | OPN5 | NM_021896 | GUCYLA3 |
| NM_175432 | TMEML32C | NM_207222 | LMO3 | NM_001025577 | MAF |
| NM_144828 | PPPLRLB | NM_028719 | CPNE4 | NM_008022 | FOXD4 |
| NM_001029878 | LONRF2 | NM_011993 | DPYSL4 | NM_001109758 | BCAN |
| NM_001001881 | 2510009E07RIK | NM_008973 | PTN | NM_022814 | SVEP1 |
| NM_026324 | KIRREL3 | NM_008499 | LHX5 | NM_007625 | CBX4 |
| NM_001081306 | PTPRZL | NM_025696 | SORCS3 | NM_026408 | SNCAIP |
| NM_029792 | B3GATL | NM_022723 | SCUBEL | NM_173446 | FAML55A |
| NM_145459 | ZFP503 | NM_020610 | NRIP3 | NM_009700 | AQP4 |
| NM_010750 | MAB21LL | NM_007963 | MECOM | NM_172296 | DMRTA2 |
| NM_178678 | LRRTM3 | NM_018797 | PLXNCL | NM_021381 | PROKRL |
| NM_009697 | NR2F2 | NM_001142731 | KCTDL | NM_010141 | EPHA7 |
| NM_010231 | FMOL | NM_010100 | EDAR | NM_175407 | SOBP |

TABLE 2A-continued

Neuroectoderm associated Genes

| REFSEQ | NAME | REFSEQ | NAME | REFSEQ | NAME |
|---|---|---|---|---|---|
| NM_152229 | NR2EL | NM_024291 | KY | NM_198302 | RBMLL |
| NM_009344 | PHLDAL | NM_001101507 | CLEC2L | NM_021377 | SORCSL |
| NR_028578 | GML0584 | NM_011580 | THBSL | NM_175564 | TMEML69 |
| NM_001001979 | MEGF10 | NM_011448 | SOX9 | NM_007759 | CRABP2 |
| NM_010710 | LHX2 | NR_026942 | E330013P04RIK | NM_025557 | PCP4LL |
| NM_198702 | LPHN3 | NM_183171 | FEZL | NM_001033446 | GM949 |
| NM_177360 | DMRT3 | NR_028377 | A930004D18RIK | NR_015552 | 53304 34G04RIK |
| NM_207583 | FAM5B | NR_015560 | 2610028E06RIK | NM_172610 | MPPEDL |
| NM_007901 | SLPRL | NM_177769 | ELMODL | NM_133237 | APCDD1 |
| NM_011023 | OTXL | NM_011817 | GADD45G | NM_175459 | GLIS3 |
| NM_013833 | RAX | NR_015386 | SIX3OSL | NM_031396 | CNNM1 |
| NM_029426 | BRSK2 | NM_011800 | CDH20 | NM_001001985 | NAT8L |
| NM_172612 | RNDL | NR_028262 | RMST | NM_009317 | TAL2 |
| NM_007495 | ASTNL | NM_020052 | SCUBE2 | NM_139146 | SATB2 |
| NM_001033324 | ZBTBL6 | NM_145463 | SHISA2 | NR_002863 | EMX2OS |
| NM_175506 | ADAMTSL9 | NM_010194 | FES | NM_054095 | NECAB2 |
|  |  |  |  | NM_001015039 | ZFYVE28 |
|  |  |  |  | NM_016743 | NELL2 |
|  |  |  |  | NM_145983 | KCNA5 |
| NM_001040086 | Sytl2 | NM_011129 | 3932 | NM_001081377 | Pcdh9 |
| NM_021458 | Fzd3 | NM_001171002 | Degs2 | NM_001033329 | Arhgef9 |
| NM_013454 | Abcal | NM_011839 | Mab21l2 | NM_053206 | Magee2 |
| NM_001164493 | Klhl29 | NR_029382 | Mirhgl | NM_178608 | Reepl |
| NM_013496 | Crabpl | NM_013669 | Snap91 | NM_175485 | Prtg |
| NM_008055 | Fzd4 | NM_011746 | Mkrn3 | NM_010150 | Nr2f6 |
| NM_031202 | Tyrp1 | NM_172752 | Sorbs2 | NM_001081012 | 4930473A06Rik |
| NM_008494 | Lfng | NR_015556 | 2610035D17Rik | NM_175259 | Shisa4 |
| NM_007831 | Dcc | NM_009428 | Trpc5 | NM_017392 | Celsr2 |
| NM_010748 | Lyst | NM_010816 | Morel | NM_053117 | Pard6g |
| NM_010420 | Hesxl | NM_177082 | Sp8 | NM_201600 | Myo5b |
| NM_175667 | Ankrd5 | NM_175366 | Mex3b | NM_010474 | Hs3stl |
| NM_009829 | Ccnd2 | NM_030708 | Zfhx4 | NM_010207 | Fgfr2 |
| NM_008741 | Nsg2 | NM_001085378 | Myh7b | NM_008926 | Prkg2 |
| NM_001115075 | H2-M5 | NM_009621 | Adamtsl | NM_177577 | Dcdc2a |
| NM_181585 | Pik3r3 | NM_019423 | Elovl2 | NM_013588 | Lrrc23 |
| NM_007743 | Colla2 | NM_010167 | Eya4 | NM_177618 | Wscdl |
| NM_178738 | Prss35 | NM_021427 | Faml81b | NM_001013386 | RasllOb |
| NM_011037 | Pax2 | NM_197990 | 1700025G04RiK | NM_013533 | Gprl62 |
| NM_027518 | Gprl37c | NM_007461 | Apba2 | NM_001130188 | Sgce |
| NR_015464 | A330069E16Rik | NM_001081333 | Plekhg4 | NM_008872 | Plat |
| NM_001122889 | Epha7 | NM_021530 | Slc4a8 | NM_172890 | Slc6all |
| NM_029679 | Fam65b | NM_001081160 | Mdgal | NM_016803 | Chst3 |
| NM_177740 | Rgma | NM_015803 | Atp8a2 | NM_001024707 | Lrp3 |
| NM_175276 | Fhod3 | NM_177715 | Kctdl2 | NM_008086 | Gasl |
| NM_001048167 | Mtap6 | NM_001170540 | Btf3 | NM_030179 | Clip4 |
| NM_028053 | Tmem38b | NM_145142 | ChstlO | NM_013788 | Pegl2 |
| NM_001081390 | Palld | NM_008516 | Lrrnl | NM_080466 | Kcnn3 |
| NM_033268 | Actn2 | NM_145525 | Osbpl6 | NM_011443 | Sox2 |
| NM_053085 | Tcf23 | NM_172913 | Tox3 | NM_029747 | 2410137M14Rik |
| NM_001004173 | Sgpp2 | NM_010291 | Glrb | NM_021361 | Noval |
| NM_028889 | Efhdl | NM_053199 | Cadm3 | NM_009306 | Sytl |
| NM_011019 | Osmr | NM_178591 | Nrgl | NM_001163175 | Begain |
| NM_001160262 | Fam78b | NM_182809 | Ntrk3 | NM_008624 | Mras |
| NM_028664 | Ankrd45 | NM_175514 | Faml71b | NR_015531 | 2700023E23Rik |
| NM_010942 | Nsgl | NM_009237 | Sox3 | NM_144786 | Ggt7 |
| NM_011158 | Prkar2b | NM_001099299 | Ajapl | NM_008447 | Kif5a |
| NM_008132 | Glrpl | NM_153118 | Fnbpll | NM_054068 | Vsxl |
| NM_175454 | C630004H02Rik | NM_029441 | Cdyl2 | NM_013834 | Sfrpl |
| NM_153166 | Cpne5 | NM_080448 | Srgap3 | NM_201411 | Flrtl |
| NM_146025 | Samdl4 | NM_178406 | Gprl53 | NM_021716 | Fign |
| NM_008130 | Gli3 | NM_198111 | Akap6 | NM_178750 | Ssl8ll |
| NM_145448 | 9030617O03Rik | NM_183172 | Ric8b | NM_001167879 | Fam59b |
| NM_183147 | Sprn | NM_172911 | D8Ertd82e | NM_018804 | Sytll |
| NM_009234 | Soxll | NM_001039934 | Mtap2 | NM_030706 | Trim2 |
| NM_177354 | Vashl | NM_001080548 | Usp6nl | NM_010111 | Efnb2 |
| NM_030209 | Crispld2 | NM_023566 | Muc2 | NM_011943 | Map2k6 |
| NM_009506 | Vegfc | NM_001135001 | Ppp2r5c | NM_175649 | Tnfrsf26 |
| NR_015606 | 9530009M10Rik | NM_010251 | Gabra4 | NM_013737 | Pla2g7 |
| NM_021488 | Ghrl | NM_001163566 | Crb2 | NM_028576 | 1700106N22Rik |
| NM_013494 | Cpe | NM_023608 | Gdpd2 | NM_009926 | Colll a2 |
| NM_028778 | Nuak2 | NM_011889 | 3932 | NM_013603 | Mt3 |
| NM_011546 | Zebl | NM_008083 | Gap43 | NM_001164504 | Rnfl65 |
| NM_130448 | Pcdh18 | NM_172706 | 9330182L06Rik | NM_011350 | Sema4f |
| NM_026886 | Srrm4 | NM_201355 | Natl4 | NM_145492 | Zfp521 |
|  |  | NM_007564 | Zfp36ll | NM_001162943 | Dchsl |
| NM_001163284 | Zbtb5 | NM_207281 | 4832428D23Rik | NM_013626 | Pam |

TABLE 2A-continued

Neuroectoderm associated Genes

| REFSEQ | NAME | REFSEQ | NAME | REFSEQ | NAME |
|---|---|---|---|---|---|
| NM_016762 | Matn2 | NM_009369 | Tgfbi | NM_175312 | B630005N14Rik |
| NM_175507 | Tmem20 | NM_007552 | Bmil | NM_026279 | Bend5 |
| NM_001081324 | Neto2 | NR_015469 | 2810442I21Rik | NM_001164663 | 9830001H06Rik |
| NM_009129 | Scg2 | NM_019439 | Gabbrl | NM_013586 | Loxl3 |
| NM_183029 | Igf2bp2 | NM_021424 | Pvrll | NM_175171 | Mast4 |
| NM_026582 | Wls | NM_173745 | Dusp18 | NM_010882 | Ndn |
| NM_021543 | Pcdh8 | NM_001085549 | Gml2824 | NM_008629 | Msil |
| NM_178280 | Sall3 | NM_175473 | Frasl | NM_138682 | Lrrc4 |
| NM_020007 | Mbnll | NM_010133 | Enl | NM_173011 | Idh2 |
| NM_172867 | Zfp462 | NM_010574 | Irx2 | NM_153808 | Smc5 |
| NM_175484 | Coro2b | NM_139218 | Dppa3 | NM_026047 | Rnf219 |
| NM_021885 | Tub | NM_009336 | Vps72 | NM_144915 | Daglb |
| NM_172813 | Enoxl | NM_178675 | Slc35fl | NM_001025192 | Cxadr |
| NM_029920 | Mtus2 | NM_001081421 | Galntll | NM_175122 | Rab39b |
| NM_023328 | Agtpbpl | NM_024477 | Ttc28 | NM_033602 | Peli2 |
| NM_010904 | Nefh | NM_172862 | Frem2 | NM_010820 | Mpdz |
| NM_172525 | Arhgap29 | NM_016846 | Rgll | NM_008059 | G0s2 |
| NM_013661 | Sema5b | NM_013755 | Gyg | NM_001013577 | 1110054O05Rik |
| NM_018807 | Plagl2 | NM_177727 | Lsml4b | NM_175089 | Nekl |
| NM_011599 | Tlel | NM_001081668 | Nup62cl | NM_175245 | 2410129H14Rik |
| NM_026139 | Armcx2 | NM_175256 | Hegl | NM_001007573 | Maneal |
| NM_028208 | Ptarl | NM_139143 | Slc39a6 | NM_145587 | Sbkl |
| NM_133197 | Mcf2 | NM_001081403 | Klhll4 | NM_207203 | BC068157 |
| NM_177814 | Erc2 | NM_008595 | Mfng | NM_172845 | Adamts4 |
| NM_009233 | Soxl | NM_025943 | Dzipl | NM_001081252 | Uggt2 |
| NM_010496 | Id2 | NM_023844 | Jam2 | NM_201607 | Pde4c |
| NM_015772 | Sall2 | NM_011670 | Uchll | NR_033430 | Gm2694 |
| NM_177674 | 2010015L04Rik | NM_020026 | B3galntl | NM_144817 | Camklg |
| NM_001083628 | Grebll | NM_145129 | Chrna3 | NM_025661 | Ormdl3 |
| NM_010518 | Igfbp5 | NM_027457 | 5730437N04Rik | NM_028546 | 1700066M21Rik |
| NM_054053 | Gpr98 | NM_010308 | Gnaol | NM_133764 | Atp6v0e2 |
| NM_173769 | Zfp641 | NM_007488 | Arnt2 | NR_015595 | 2410137F16Rik |
| NM_183138 | Tet3 | NM_008634 | Mtaplb | NM_016902 | Nphpl |
| NM_175199 | Hspal2a | NM_027015 | Rps27 | NM_172412 | Gpc2 |
| NM_008321 | Id3 | NM_008862 | Pkia | NM_011204 | Ptpnl3 |
| NM_029614 | Prss23 | NM_172467 | Zc3havll | NM_001081348 | Hecwl |
| NR_015524 | 4932415G12Rik | NM_146122 | Denndla | NM_001081346 | Rtkn2 |
| NM_001163288 | Susdl | NM_011795 | Clqll | NM_001081267 | Rsfl |
| NM_007911 | Efnb3 | NM_021362 | Pappa | NM_030694 | Ifitm2 |
| NM_010279 | Gfral | NM_025954 | Pgp | NM_010544 | Ihh |
| NR_002889 | Gm5801 | NM_172205 | Sbsn | NM_007396 | Acvr2a |
| NM_015753 | Zeb2 | NM_080845 | Ftcd | NM_144867 | Slmol |
| NM_001039179 | Bicd2 | NM_178782 | Bcorll | NM_001004062 | Crtcl |
| NM_023716 | Tubb2b | NM_181548 | Eras | NM_145144 | Aifll |
| NM_198620 | Rundc3b | NM_007836 | Gadd45a | NM_010137 | Epasl |
| NM_007881 | Atnl | NM_008976 | Ptpnl4 | NM_027870 | Armcx3 |
| NM_197945 | Prosapipl | NM_001163637 | Jakmip2 | NM_013691 | Thbs3 |
| NM_026167 | Klhll3 | NM_146142 | Tdrd7 | NM_009556 | Zfp42 |
| NM_178655 | Ank2 | NM_173016 | Vatll | NM_172261 | Ppplr9b |
| NM_028317 | 2810030E01Rik | NM_026056 | Cap2 | NM_001029982 | Sec23ip |
| NM_177167 | Ppmle | NM_001163766 | Wdr90 | NM_001004153 | AU018091 |
| NM_011600 | Tle4 | NM_010768 | Matk | NM_146001 | Hipl |
| NM_019626 | Cblnl | NM_153537 | Phldbl | NM_010917 | Nidi |
| NM_028982 | 8430419L09Rik | NM_029930 | Famll5a | NM_017467 | Zfp316 |
| NM_021563 | Erbb2ip | NM_175234 | 6230409E13Rik | NM_172151 | Zdhhc8 |
| NR_028571 | Snoral7 | NM_001081088 | Lrp2 | NM_001159645 | Araf |
| NM_178877 | Nhedc2 | NM_009409 | Top2b | NM_001166581 | BC005561 |
| NM_011035 | Pakl | NM_001163145 | 1810041L15Rik | NM_008180 | Gss |
| NM_028493 | Rhobtb3 | NM_001159889 | Ociadl | NM_011890 | Sgcb |
| NM_177364 | Sh3pxd2b | NM_010795 | Mgat3 | NM_001025246 | Trp53ill |
| NM_013886 | Hdgfrp3 | NM_013835 | Trove2 | NM_178626 | Cdc42se2 |
| NM_172471 | Itih5 | NM_001122893 | Fyn | NM_008480 | Lamal |
| NM_011228 | Rab33a | NM_016750 | H2afz | NM_011297 | Rps24 |
| NM_172771 | Dmxl2 | NM_026534 | Ubxn2b | NM_146208 | Neil3 |
| NM_007537 | Bcl2l2 | NM_001081428 | Faml84a | NM_008891 | Pnn |
| NM_009988 | Cxadr | NM_001081114 | Clip3 | NM_009791 | Aspm |
| NM_015798 | Fbxol5 | NM_025445 | Arfgap3 | NM_001039546 | Myo6 |
| NM_175193 | Golim4 | NM_031392 | Wdr6 | NM_007386 | Acol |
| NM_181815 | 4930534B04Rik | NM_007789 | Ncan | NM_057172 | Fubpl |
| NM_021886 | Cenph | NM_009530 | Atrx | NM_001081395 | Amotll |
| NM_025693 | Tmem41a | NM_029861 | Cnripl | NM_025623 | Nipsnap3b |
| NM_001081446 | Iqck | NM_027248 | Zfp219 | NM_178896 | Dcunld4 |
| NM_011162 | Mapk8ipl | NM_031162 | Cd247 | NM_172538 | Vezt |
| NM_009685 | Apbbl | NM_007862 | Dlgl | NM_145574 | Ccdcl36 |
| NM_033474 | Arvcf | NM_019570 | Revl | NM_001081251 | Pbrml |
| NM_025329 | Tctexld2 | NM_001081417 | Chd7 | NM_028711 | Slc25a27 |

TABLE 2A-continued

Neuroectoderm associated Genes

| REFSEQ | NAME | REFSEQ | NAME | REFSEQ | NAME |
|---|---|---|---|---|---|
| NR_024619 | 2610001705Rik | NM_199316 | 4922501C03Rik | NM_033618 | Suptl6h |
| NM_009182 | St8sia3 | NM_009628 | Adnp | NM_008796 | Pctp |
| NM_172449 | Bzrapl | NM_007399 | AdamlO | NM_001113384 | Gnaol |
| NM_001033272 | Spatal3 | NM_009214 | Sms | NM_177475 | Zfp280b |
| NM_145930 | AW549877 | NM_144873 | Uhrf2 | NM_023053 | Twsgl |
| NM_181395 | Pxdn | NM_175174 | Klhl5 | NM_001029983 | Manlbl |
| NM_029752 | Bri3bp | NM_009178 | St3gal4 | NM_021346 | Zfp318 |
| NM_010626 | Kif7 | NM_025592 | Rpl35 | | |
| NM_011514 | Suv39hl | NM_011161 | Mapkll | | |
| NM_030210 | Aacs | NM_027898 | Gramdla | | |
| NM_138755 | Phf21a | NM_030714 | Dtx3 | | |
| NM_029742 | KlhdclO | NM_001099637 | Cepl70 | | |
| | | NM_001002272 | Tro | | |

TABLE 2B

Primitive Streak associated Genes

| REFSEQ_ID | NAME | REFSEQ_ID | NAME | REFSEQ_ID | NAME |
|---|---|---|---|---|---|
| NM_007553 | Bmp2 | NM_010724 | Psmb8 | NM_001033217 | Pricklel |
| NM_177059 | Fstl4 | NM_028980 | Ppp4r4 | NM_054041 | Antxrl |
| NM_133836 | 1115 ra | NM_026481 | Tppp3 | NM_023697 | Rdhl4 |
| NM_001033415 | Shisa3 | NM_028783 | Robo4 | NM_016719 | Grbl4 |
| NM_007702 | Cidea | NM_177755 | Klhl38 | NM_008795 | Cdkl8 |
| NM_009393 | Tnncl | NM_013851 | Abca8b | NM_018777 | Cldn6 |
| NM_177260 | Tmeml54 | NM_144547 | Amhr2 | NM_007966 | Evxl |
| NM_009521 | Wnt3 | NM_010260 | Gbp2 | NM_001145162 | Ube2qll |
| NM_001025581 | Kcnc2 | NM_008046 | Fst | NM_030711 | Erapl |
| NM_022995 | Pmepal | NM_053262 | Hsdl7bll | NM_013633 | Pou5fl |
| NM_010934 | Npylr | NM_010094 | Leftyl | NM_009660 | Aloxl5 |
| NM_001166363 | Fgf8 | NM_001024703 | Mctp2 | NM_028478 | Rassf6 |
| NM_001024614 | 1700007GllRik | NM_023580 | Ephal | NM_133664 | Ladl |
| NM_023456 | Npy | NM_008343 | Igfbp3 | NM_019457 | Lrrc6 |
| NM_172777 | Gbp9 | NM_013675 | Spnbl | NM_177303 | Lrrn4 |
| NM_010259 | Gbpl | NM_024440 | Derl3 | NM_011527 | Tall |
| NM_001048207 | Gypc | NM_028841 | Tspanl7 | NM_001081202 | Lltdl |
| NM_018734 | Gbp3 | NM_008331 | Ifitl | NM_001081295 | 4631416L12Rik |
| NM_001013816 | Gm5622 | NM_008353 | Ill2rbl | NM_008519 | Ltb4rl |
| NM_015736 | Galnt3 | NM_198632 | Trim67 | NM_010127 | Pou6fl |
| NM_013611 | Nodal | NM_010203 | Fgf5 | NM_172781 | Klhl4 |
| NM_007464 | Birc3 | NM_001039578 | Evi5l | NM_010473 | Hrc |
| NM_013751 | Hrasls | NM_001104614 | Vmn2r3 | NM_173388 | Slc43a2 |
| NM_213727 | Faml23c | NM_009099 | Trim30 | NM_138606 | Pim2 |
| NM_010290 | Gjd2 | NM_130456 | Nphs2 | NM_177741 | Ppplr3b |
| NM_058212 | Dpf3 | NM_053248 | Slc5a5 | NM_008829 | Pgr |
| NM_019967 | Dbcl | NM_133994 | Gstt3 | NM_010351 | Gsc |
| NM_011169 | Prlr | NM_009373 | Tgm2 | NM_001101488 | Gsgll |
| NM_009290 | Wnt8a | NM_025831 | 1300014106Rik | NM_013749 | Tnfrsfl2a |
| NM_010208 | Fgr | NM_080639 | Timp4 | NM_031402 | Crispldl |
| NM_010608 | Kcnk3 | NM_001081120 | Fam89a | NM_025868 | Tmx2 |
| NM_011348 | Sema3e | NM_008426 | Kcnj3 | NM_180958 | Ccdc79 |
| NM_009322 | Tbrl | NM_011854 | Oasl2 | NM_146011 | Arhgap9 |
| NM_023386 | Rtp4 | NM_011674 | Ugt8a | NM_022987 | Zic5 |
| NM_177694 | Ano5 | NM_053109 | Clec2d | NM_028013 | Endodl |
| NM_018827 | Crlfl | NM_001162957 | Rsph4a | NM_021509 | Moxdl |
| NM_027990 | Lypd6b | NM_001115154 | Samd3 | NM_026928 | 1810014F10Rik |
| NM_175532 | NlrplO | NM_029182 | Rasd2 | NM_146062 | Pphlnl |
| NM_028584 | Marveld3 | NM_016798 | Pdlim3 | NM_009309 | T |
| NM_001045518 | Fam83b | NM_027828 | FamllOc | NM_018754 | Sfn |
| NM_008909 | Ppl | NM_177759 | Ccdc60 | NM_011057 | Pdgfb |
| NM_009135 | Scn7a | NM_026954 | Tuscl | NM_001001806 | Zfp36l2 |
| NM_028351 | Rspo3 | NM_007976 | F5 | NM_008727 | Nprl |
| NM_015783 | Isgl5 | NM_010156 | Samd9l | NM_019440 | Irgm2 |
| NM_021715 | Chst7 | NM_177898 | Nek5 | NM_029341 | Capsl |
| NM_008958 | Ptch2 | NM_009864 | Cdhl | NM_007974 | F2rll |
| NM_008518 | Ltb | NM_001017427 | Rasef | NM_019510 | Trpc3 |
| NM_178920 | Mal2 | NM_130878 | Cdhrl | NM_177638 | Crb3 |
| NM_028096 | 2010300C02Rik | NM_001160386 | Dnahc7b | NM_025992 | Herc5 |
| NM_019467 | Aifl | NM_011773 | Slc30a3 | NM_029537 | Tmem98 |
| NM_001002927 | Penk | NM_026821 | D4Bwg0951e | NM_010346 | Grb7 |
| NM_001081285 | Mup6 | NM_023850 | Chstl | NM_013777 | Akrlcl2 |
| NM_028864 | Zc3havl | NM_026672 | Gstm7 | NM_172621 | Clic5 |

TABLE 2B-continued

Primitive Streak associated Genes

| REFSEQ_ID | NAME | REFSEQ_ID | NAME | REFSEQ_ID | NAME |
|---|---|---|---|---|---|
| NM_011851 | Nt5e | NM_010139 | Epha2 | NM_153805 | Pkn3 |
| NM_015744 | Enpp2 | NM_009374 | Tgm3 | NM_009897 | Ckmt1 |
| NM_194263 | Tbx20 | NM_001163136 | Macc1 | NM_028870 | Cltb |
| NM_133969 | Cyp4v3 | NM_016899 | Rab25 | NM_010023 | Dci |
| NM_022315 | Smoc2 | NM_001033339 | Mmp25 | NM_017400 | Sh3gl3 |
| NM_001136079 | Ptger4 | NM_007989 | Foxh1 | NM_011518 | Sykb |
| NM_133990 | Il13ra1 | NM_033564 | Mpv17l | NM_013471 | Anxa4 |
| NM_172285 | Plcg2 | NM_175329 | Chchd10 | NM_173394 | Ticam2 |
| NM_001168571 | Ctps2 | NM_001039530 | Parp14 | NM_011526 | Tagln |
| NM_145836 | 6430527G18Rik | NM_172398 | Akr1b10 | NM_145608 | BC021891 |
| NM_013912 | Apln | NM_145523 | Gca | NM_001033311 | Vsig10 |
| NM_153533 | Tcn1 | NM_010664 | Krt18 | NM_028132 | Pgm2 |
| NM_010726 | Phyh | NM_010910 | Nefl | NM_009121 | Sat1 |
| NM_173372 | Grm6 | NM_029999 | Lbh | NM_153534 | Adcy2 |
| NM_021534 | Pxmp4 | NM_198093 | Elmo1 | NM_011113 | Plaur |
| NM_146013 | Sec14l4 | NM_153807 | Acsf2 | NM_172893 | Parp12 |
| NM_008620 | Gbp4 | NM_009873 | Cdk6 | NM_172124 | B3gat2 |
| NM_018764 | Pcdh7 | NM_020043 | Igdcc4 | NM_030253 | Parp9 |
| NM_133674 | Arhgef5 | NM_028030 | Rbpms2 | NM_001076791 | 9630025I21Rik |
| NM_019949 | Ube2l6 | NM_183027 | Apls3 | NM_029803 | Ifi27l2a |
| NM_178674 | Fbxl21 | NM_008430 | Kcnk1 | NM_009354 | Tert |
| NM_001007463 | Spag8 | NM_026637 | Ggct | NM_011597 | Tjp2 |
| NM_010930 | Nov | NM_023141 | Tor3a | NM_007962 | Mpzl2 |
| NM_019701 | Clcnkb | NM_025912 | 2010011I20Rik | NM_176971 | Rab9b |
| NM_022019 | Dusp10 | NM_010902 | Nfe2l2 | NM_177129 | Cntn2 |
| NM_010400 | H60a | NM_009413 | Tpd52l1 | NM_022415 | Ptges |
| NM_009982 | Ctsc | NM_007883 | Dsg2 | NM_177900 | Hapln4 |
| NM_007440 | Alox12 | NM_022886 | Sec1 | NM_019739 | Foxo1 |
| NM_025865 | 2310030G06Rik | NM_027872 | Slc46a3 | NM_207176 | Tes |
| NM_029881 | Tmem200a | NM_008815 | Etv4 | NM_178907 | Mapkapk3 |
| NM_011176 | St14 | NM_144794 | Tmem63a | NM_178737 | AW551984 |
| NM_029770 | Unc5b | NM_010516 | Cyr61 | NM_023059 | Sigirr |
| NM_008260 | Foxa3 | NM_019487 | Hebp2 | NM_025730 | Lrrk2 |
| NM_009197 | Slc16a2 | NM_008029 | Flt4 | NM_011018 | Sqstm1 |
| NM_175175 | Plekhf2 | NM_198003 | 1300003B13Rik | NM_145952 | Tbc1d2 |
| NM_029384 | 2210411K11Rik | NM_001039485 | Fam38b | NM_026880 | Pink1 |
| NM_080419 | Igsf5 | NM_008937 | Prox1 | NM_145148 | Frmd4b |
| NM_027402 | Fndc5 | NM_021893 | Cd274 | NM_172441 | Shroom2 |
| NM_011562 | Tdgf1 | NM_145562 | Parm1 | NM_013556 | Hprt |
| NM_001002897 | Atg9b | NM_008939 | Prss12 | NM_001081047 | Cnksr1 |
| NM_009509 | Vill | NM_130859 | Card10 | NM_011756 | Zfp36 |
| NM_001162954 | Gm8267 | NM_029619 | Msrb2 | NM_013505 | Dsc2 |
| NM_133485 | Ppp1r14c | NM_001042660 | Smad7 | NM_007381 | Acad1 |
| NM_031199 | Tgfa | NM_173752 | 1110067D22Rik | NM_175523 | Ppm1k |
| NM_026496 | Grhl2 | NM_194055 | Esrp1 | NM_172785 | Zc3h12d |
| NM_007847 | Defa-rs2 | NM_008580 | Map3k5 | NM_022032 | Perp |
| NM_008173 | Nr3c1 | NR_026853 | A930012L18Rik | NM_011412 | Slit3 |
| NM_009112 | S100a10 | NM_013469 | Anxa11 | NM_001013371 | Dtx3l |
| NM_001166067 | Slc4a5 | NM_052994 | Spock2 | NM_172980 | Slc28a2 |
| NM_001166662 | Ccdc85a | NM_009801 | Car2 | NM_030556 | Slc19a3 |
| NM_001111119 | Ccnb1ip1 | NM_001081175 | Itpkb | NM_025339 | Tmem42 |
| NM_021453 | Pga5 | NM_133715 | Arhgap27 | NM_026183 | Slc47a1 |
| NM_138953 | El12 | NM_175313 | A130022J15Rik | NM_145933 | St6gal1 |
| NM_001081253 | Fbxo43 | NM_018738 | Igtp | NM_001011874 | Xkr4 |
| NM_009569 | Zfpm1 | NM_001038602 | Marveld2 | NM_145547 | Zfp189 |
| NM_181542 | Slfn10 | NM_011405 | Slc7a7 | NM_001003948 | Pid1 |
| NM_178749 | Stk32a | NM_016658 | Gait | NM_028375 | Cxxlc |
| NM_013795 | Atp5l | NM_001081097 | Grik3 | NM_008538 | Marcks |
| NM_153551 | Dennd1c | NM_013738 | Plek2 | NM_177073 | Relt |
| NM_026268 | Dusp6 | NM_145391 | Tapbpl | NM_176952 | 6430573F11Rik |
| NM_008879 | Lcp1 | NM_027406 | Aldh1l1 | NM_001177391 | Gm6788 |
| NM_144549 | Trib1 | NM_001109661 | Bach2 | NM_008990 | Pvrl2 |
| NM_027871 | Arhgef3 | NM_009287 | Stim1 | NM_008608 | Mmp14 |
| NM_007898 | Ebp | NM_001134741 | Tdrd5 | NM_010593 | Jup |
| NM_178405 | Atp1a2 | NM_177595 | Mkx | NM_009283 | Stat1 |
| NM_001005863 | Mtus1 | NM_029688 | Srxn1 | NM_177078 | Adrbk2 |
| NM_027799 | Ankrd40 | NM_010347 | Aes | NM_145934 | Stap2 |
| NR_015517 | 5930412G12Rik | NM_182927 | Spred3 | NM_007611 | Casp7 |
| NM_133687 | Cxxc5 | NM_029508 | Pcgf5 | NM_175270 | Ankrd56 |
| NM_001024139 | Adamtsl5 | NM_026213 | Ttc33 | NM_008185 | Gstt1 |
| NM_001042715 | Ccdc135 | NM_016736 | Nub1 | NM_016797 | Stx7 |
| NM_001081193 | Lemd3 | NM_016907 | Spint1 | NM_153287 | Csrnp1 |
| NM_009426 | Trh | NM_023270 | Rnf128 | NM_001081162 | Slc4a11 |
| NM_028788 | 1300002K09Rik | NM_016863 | Fkbp1b | NM_007737 | Col5a2 |
| NM_144853 | Cyyr1 | NM_182841 | Tmem150c | NM_018744 | Sema6a |
| NM_030677 | Gpx2 | NM_008150 | Gpc4 | NM_008175 | Grn |

TABLE 2B-continued

Primitive Streak associated Genes

| REFSEQ_ID | NAME | REFSEQ_ID | NAME | REFSEQ_ID | NAME |
|---|---|---|---|---|---|
| NM_207208 | Clca6 | NM_146061 | Prr5 | NM_025346 | Rmnd5b |
| NM_011989 | Slc27a4 | NM_010749 | M6pr | NM_018789 | Foxo4 |
| NM_172294 | Sulf1 | NM_010657 | Hivep3 | NM_176837 | Arhgap18 |
| NM_134000 | Traf3ip2 | NM_021431 | Nudt11 | NM_173395 | Fam132b |
| NM_001081416 | Fndc1 | NM_019425 | Gnpnat1 | NM_172383 | Tmem125 |
| NM_134437 | Il17rd | NM_175212 | Tmem65 | NM_028057 | Cyb5r1 |
| NM_001081322 | Myo5c | NM_173071 | Bai2 | NM_016740 | Sl00a11 |
| NM_023184 | Klf15 | NM_145973 | El13 | NM_009673 | Anxa5 |
| NM_013580 | Ldhc | NM_008209 | Mrl | NM_011803 | Klf6 |
| NM_008216 | Has2 | NM_021605 | Nek7 | NM_001025566 | Chka |
| NM_001145978 | Parp4 | NM_172924 | C230081A13Rik | NM_001013616 | Trim6 |
| NM_172588 | Serinc5 | NM_027769 | Cpne3 | NM_010008 | Cyp2j6 |
| NM_013813 | Epb4.113 | NM_019733 | Rbpms | NR_015475 | 1700086O06Rik |
| NM_001080814 | Fat3 | NM_013642 | Dusp1 | NM_133816 | Sh3bp4 |
| NM_001109747 | 2610036L11Rik | NM_001081337 | Sipa1l2 | NM_021557 | Rdh11 |
| NM_013843 | Zfp53 | NM_153783 | Paox | NM_178598 | Tagln2 |
| NR_033535 | Gm10845 | NM_011760 | Zfp54 | NM_009331 | Tcf7 |
| NM_013563 | Il2rg | NM_153123 | Atf7ip2 | NM_199022 | Shc4 |
| NM_013876 | Rnf11 | NM_027906 | 1300010F03Rik | NM_007421 | Adssl1 |
| NM_146151 | Tesk2 | NM_012030 | Slc9a3r1 | NM_011207 | Ptpn3 |
| NM_023663 | Ripk4 | NM_152220 | Stx3 | NM_172409 | Fmnl2 |
| NM_007805 | Cyb561 | NM_013727 | Azi2 | NM_016978 | Oat |
| NM_027154 | Tmbim1 | NM_008908 | Ppic | NM_001080926 | Lrp8 |
| NM_028320 | Adipor1 | NM_010591 | Jun | NM_133217 | Bco2 |
| NM_028064 | Slc39a4 | NM_009107 | Rxrg | NM_146040 | Cdca7l |
| NM_008817 | Peg3 | NM_183088 | Scand3 | NM_010578 | Itgb1 |
| NM_009642 | Agtrap | NM_007512 | Atpif1 | NM_145617 | Herc1 |
| NM_013781 | Sh2d3c | NM_027468 | Cpm | NM_011609 | Tnfrsf1a |
| NM_013759 | Sepx1 | NM_133705 | Pycr2 | NM_022410 | Myh9 |
| NM_023805 | Slc38a3 | NR_015551 | 1700012B15Rik | NM_011988 | Slc27a3 |
| NM_013587 | Lrpap1 | NM_013565 | Itga3 | NM_009565 | Zbtb7b |
| NM_001162909 | Ncrna00085 | NM_016861 | Pdlim1 | NM_011197 | Ptgfrn |
| NM_001002008 | BC049807 | NM_007494 | Ass1 | NM_026053 | Gemin6 |
| NM_010305 | Gnai1 | NM_001033298 | Plk1s1 | NM_009573 | Zic1 |
| NM_001038593 | Glrx2 | NM_009728 | Atp10a | NM_010568 | Insr |
| NM_001081308 | Taok3 | NM_026599 | Cgn1l | NM_181848 | Optn |
| NM_016811 | Dgka | NM_032000 | Trps1 | NM_027257 | Obfc2b |
| NM_025538 | Alkbh7 | NM_008992 | Abcd4 | NM_175114 | Trak1 |
| NM_029947 | Prdm8 | NM_023794 | Etv5 | NM_025968 | Ptgr1 |
| NM_010638 | Klf9 | NM_027544 | Ggnbp1 | NM_019657 | Hsd17b12 |
| NM_011206 | Ptpn18 | NM_010330 | Emb | NM_013628 | Pcsk1 |
| NM_013514 | Epb4.9 | NM_008924 | Prkar2a | NM_022327 | Ralb |
| NM_009579 | Slc30a1 | NM_001045514 | Akna | NM_013803 | Casr |
| NM_175168 | Ptk7 | NM_008522 | Ltf | NM_010060 | Dnahc11 |
| NM_007523 | Bak1 | NM_007417 | Adra2a | NM_028133 | Egln3 |
| NM_134042 | Aldh6a1 | NM_010863 | Myo1b | NM_010395 | H2-T10 |
| NM_198029 | Fermt1 | NM_016685 | Comp | NM_007801 | Ctsh |
| NM_016851 | Irf6 | NM_027320 | Ifi35 | NM_010827 | Msc |
| NM_027450 | Glipr2 | NM_027442 | Ddo | NM_010493 | Icam1 |
| NM_144796 | Susd4 | NM_009520 | Wnt2b | NM_011299 | Rps6ka2 |
| NM_173396 | Tgif2 | NM_007548 | Prdm1 | NM_013585 | Psmb9 |
| NM_009510 | Ezr | NM_172633 | Cbln2 | NM_199018 | Stard8 |
| NM_145554 | Ldlrap1 | NM_008664 | Myom2 | NM_007486 | Arhgdib |
| NM_020028 | Lpar2 | NM_027222 | 2010001M09Rik | NM_013495 | Cpt1a |
| NM_008342 | Igfbp2 | NM_026840 | Pdgfrl | NM_011267 | Rgs16 |
| NM_178060 | Thra | NM_021476 | Cysltr1 | NM_001033380 | Itpripl2 |
| NM_009180 | St6galnac2 | NM_007731 | Col3a1 | NM_008554 | Ascl2 |
| NM_010269 | Gdap2 | NM_010136 | Eomes | NM_028908 | 4933403G14Rik |
| NM_016866 | Stk39 | NM_011530 | Tap2 | NM_010605 | Kcnj5 |
| NM_007793 | Cstb | NM_027152 | Cd164l2 | NM_147778 | Commd3 |
| NM_172496 | Cobl | NM_172530 | She | NM_009900 | Clcn2 |
| NM_009046 | Relb | NM_178394 | Jakmip1 | NM_001163085 | Map3k15 |
| NM_009713 | Arsa | NM_028016 | Nanog | NM_183149 | Zfp598 |
| NM_130450 | Elovl6 | NM_008077 | Gad1 | NM_028071 | Cotl1 |
| NM_025285 | Stmn2 | NM_013468 | Ankrd1 | NM_001045516 | Proca1 |
| NM_007607 | Car4 | NM_019517 | Bace2 | NM_133955 | Rhou |
| NM_019521 | Gas6 | NM_022435 | Sp5 | NM_001114332 | Slc16a10 |
| NM_153804 | Plekhg3 | NM_126166 | Tlr3 | NM_011578 | Tgfbr3 |
| NM_023472 | Ankra2 | NM_177102 | Tmem91 | NM_009171 | Shmt1 |
| NM_207655 | Egfr | NM_001008232 | Asap3 | NM_024257 | Hdhd3 |
| NM_009164 | Sh3bp1 | NM_080637 | Nme5 | NM_172994 | Ppp1r2c |
| NM_133838 | Ehd4 | NM_133194 | Scml2 | NM_001033328 | BC023829 |
| NM_011479 | Sptlc2 | NM_008681 | Ndrg1 | NM_026526 | N6amt2 |
| NM_134076 | Abhd4 | NM_008532 | Epcam | NM_029485 | Spata24 |
| NM_172647 | F11r | NM_008116 | Ggt1 | NM_001005784 | Inadl |
| NM_028451 | Larp1 | NM_011066 | Per2 | NM_016979 | Prkx |

TABLE 2B-continued

Primitive Streak associated Genes

| REFSEQ_ID | NAME | REFSEQ_ID | NAME | REFSEQ_ID | NAME |
|---|---|---|---|---|---|
| NM_009769 | Klf5 | NM_010016 | Cd55 | NM_001013379 | D10627 |
| NM_172476 | Tmc7 | NM_027185 | Def6 | NM_015755 | Hunk |
| NM_027935 | Tmem50a | NM_008471 | Krtl9 | NM_172696 | Inadl |
| NM_009320 | Slc6a6 | NM_146162 | Tmemll9 | NM_031257 | Plekha2 |
| NM_133976 | Imp3 | NM_018861 | Slc1a4 | NM_009575 | Zic3 |
| NM_133768 | Asl | NM_010391 | H2-Q10 | NM_023057 | B230120H23Rik |
| NM_178682 | 4933426MllRik | NM_009624 | Adcy9 | NM_001037916 | Ccdc17 |
| NM_019634 | Tspan7 | NM_009101 | Rras | NM_172479 | Slc38a5 |
| NM_033521 | Laptm4b | NM_175938 | Btn2a2 | NM_001081069 | Rgsll |
| NM_027728 | Enkur | NM_011498 | Bhlhe40 | NM_022305 | B4galtl |
| NM_177233 | Faml9a4 | NM_013584 | Lifr | NM_011920 | Abcg2 |
| NM_008326 | Irgml | NM_145953 | Cth | NM_011487 | Stat4 |
| NM_146050 | Oitl | NM_008235 | Hes1 | NM_007872 | Dnmt3a |
| NM_021394 | Zbpl | NM_198962 | Hcrtr2 | NM_007760 | Crat |
| NM_001081062 | Ccno | NM_207634 | Rps24 | NM_033320 | Glee |
| NM_001112739 | Kcncl | NR_028425 | LOC100303645 | NM_178111 | Trp53inp2 |
| NM_001033247 | Wdr52 | NM_011150 | Lgals3bp | NM_008539 | Smadl |
| NM_001145959 | Ndrg2 | NM_177857 | Dennd2c | NM_146251 | Pnpla7 |
| NM_013729 | Mixll | NM_198095 | Bst2 | NM_010585 | Itprl |
| NM_008315 | Htr7 | NM_001122758 | Pcdh7 | NM_028838 | Lrrc2 |
| NM_011454 | Serpinb6b | NM_009893 | Chrd | NM_001037713 | Xafl |
| NM_008588 | Mespl | NM_007763 | Cripl | NM_001101433 | Zcchc24 |
| NM_015748 | Slitl | NM_016887 | Cldn7 | NM_010108 | Efna3 |
| NM_009329 | Zfp354a | NM_021416 | Faml84b | NM_145922 | Kcnc4 |
| NM_008756 | Ocln | NM_028472 | Bmper | NM_010233 | Fnl |
| NM_016917 | Slc40al | NM_001081104 | Chrna9 | NM_008092 | Gata4 |
| NM_175687 | A230050P20Rik | NM_029509 | Gbp8 | NM_175214 | Kif27 |
| NM_175096 | Stbdl | NM_009911 | Cxcr4 | NM_008381 | Inhbb |
| NM_181820 | Tmc4 | NM_153393 | Col23al | NM_001034858 | Armc2 |
| NM_026866 | Displ | NM_026612 | Ndufb2 | NM_007903 | Edn3 |
| NM_001033385 | D630037F22Rik | NM_007482 | Argl | NM_021560 | Bhlhe22 |
| NM_023596 | Slc29a3 | NM_008239 | Foxql | NM_001024230 | Gm5431 |
| NM_028235 | Ttc30b | NM_023048 | Asb4 | NM_013529 | Gfpt2 |
| NM_013640 | Psmb10 | NM_133731 | Prss22 | NM_027219 | Cdc42epl |
| NM_172665 | Pdkl | NM_001146073 | Hexdc | NM_010394 | H2-Q7 |
| NM_013770 | Slc25al0 | NM_007685 | Cfcl | NM_023842 | Dsp |
| NM_011663 | Zrsrl | NM_011380 | Six2 | NM_001099296 | Grrpl |
| NM_007426 | Angpt2 | NM_001033345 | Gm216 | NM_001081215 | Ddx60 |
| NM_054087 | Slc9a2 | NM_001081275 | 1700009P17Rik | NM_020033 | Ankrd2 |
| NM_009201 | Slc1a5 | NM_138650 | Dgkg | NM_008245 | Hhex |
| NM_026509 | Mure | NM_153319 | Amot | NM_025404 | Arl4d |
| NM_027464 | 5730469M10Rik | NM_008723 | Npm3 | NM_007914 | Ehf |
| NM_009458 | Ube2b | NM_183390 | Klhl6 | NM_175386 | Lhfp |
| NM_009196 | Slc16al | NM_177788 | Exoc3l | NM_010258 | Gata6 |
| NM_013511 | Epb4.1l2 | NM_008498 | Lhxl | NM_008882 | Plxna2 |
| NM_010176 | Fah | NM_177099 | Lefty2 | NM_133974 | Cdcpl |
| NM_001001892 | H2-K1 | NM_008002 | Fgfl0 | NM_008115 | Gfra2 |
| NM_133917 | Mlxip | NM_011441 | Soxl7 | NM_018805 | Hs3st3bl |
| NM_001045530 | Ccnjl | NM_009694 | Apobec2 | NM_011913 | Bestl |
| NM_027722 | Nudt4 | NM_008486 | Anpep | NM_008592 | Foxcl |
| NM_177077 | Exoc6b | NM_033073 | Krt7 | NM_030067 | Gprl15 |
| NM_007754 | Cpd | NM_008174 | Grm8 | NM_172486 | Zfp677 |
| NM_028995 | Nipal3 | NM_008213 | Handl | NM_009633 | Adra2b |
| NM_145070 | Hiplr | NM_024445 | Tsnaxipl | NM_011784 | Aplnr |
| NM_001164642 | Trappc9 | NM_008259 | Foxal | NM_010090 | Dusp2 |
| NM_008589 | Mesp2 | NM_181397 | Rftnl | NM_019781 | Pexl4 |
| NM_026146 | Eps8ll | NM_007866 | Dll3 | NM_010228 | Fltl |
| NM_153527 | Dnajbl3 | NM_010630 | Kifc2 | NM_009744 | Bcl6 |
| NM_172535 | Iqub | NM_001171003 | Mgam | NM_021323 | Usp29 |
| NM_029604 | 1700027A23Rik | NM_015802 | Dlcl | NM_009330 | Hnflb |
| NM_001024932 | Pilrb2 | NM_008737 | Nrpl | NM_001081263 | Slc44a5 |
| NM_007562 | Bncl | NM_172731 | Fgd5 | NM_009170 | Shh |
| NM_153510 | Pilra | NM_011898 | Spry4 | NM_177914 | Dgkk |
| NM_013519 | Foxc2 | NM_009887 | Cerl | NM_008478 | Llcam |
| NR_033261 | Gml4492 | NM_010517 | Igfbp4 | NM_025980 | Nrarp |
| NM_177863 | Freml | NM_013598 | Kitl | NM_009390 | Till |
| NM_001033281 | Prdm6 | NM_172524 | Nipal4 | NM_001039562 | Ankrd37 |
| NM_010350 | Grin2c | NM_009603 | Chrne | NM_015775 | Tmprss2 |
| NM_009151 | Selplg | NM_198637 | 1700016K19Rik | NM_133365 | Dnahc5 |
| NM_001081393 | Armc4 | NM_028772 | Dmgdh | NM_007603 | Capn6 |
| NM_008266 | Hoxbl | NM_011957 | Creb3ll | NM_178804 | Slit2 |
| NM_011880 | Rgs7 | NM_018867 | Cpxm2 | NM_027742 | Lrrfip2 |
| NM_001033347 | D430041D05Rik | NM_016972 | Slc7a8 | NM_009895 | Cish |
| NM_001007472 | Noto | NM_009258 | Spink3 | NM_001097621 | Kif26a |
| NM_008979 | Ptpn22 | NM_029314 | 1700013F07Rik | NM_001081453 | Nin |
| NM_010612 | Kdr | NM_025744 | 4933404M02Rik | NM_007504 | Atp2al |

TABLE 2B-continued

Primitive Streak associated Genes

| REFSEQ_ID | NAME | REFSEQ_ID | NAME | REFSEQ_ID | NAME |
|---|---|---|---|---|---|
| NM_001081178 | Gprll6 | NM_001167777 | Asxl3 | NM_007811 | Cyp26al |
| NM_145684 | Aloxl2e | NM_010097 | Sparcll | NM_010740 | Cd93 |
| NM_001172117 | Hck | NM_010195 | Lgr5 | NM_010423 | Heyl |
| NM_053190 | Slpr5 | NM_023275 | Rhoj | NM_178748 | Egflam |
| NM_001037928 | Gmll992 | NM_080288 | Elmol | NM_024264 | Cyp27al |
| NM_001113181 | Gria4 | NM_153789 | Mylip | NM_028730 | Pex26 |
| NM_027395 | Baspl | NM_027052 | Slc38a4 | NM_145526 | P2rx3 |
| NR_027920 | Msxlas | NM_001081419 | Dip2a | NM_016768 | Pbx3 |
| NM_001039676 | Slc39a2 | NM_001001321 | Slc35d2 | NM_008506 | Mycll |
| NM_010441 | Hmga2 | NM_001081059 | Ccdc90a | NM_010162 | Extl |
| NM_001085521 | Tmem90b | NM_009657 | Aldoc | NM_008445 | Kif3c |
| NM_001001309 | Itga8 | NM_009238 | Sox4 | NM_021493 | Arhgap23 |
| NM_009616 | Adaml9 | NM_028918 | Ttc25 | NM_008576 | Abccl |
| NM_010019 | Dapk2 | NM_009855 | Cd80 | NM_016677 | Hpcall |
| NM_145429 | Arrb2 | NM_025620 | Repl5 | NM_001013811 | Faml69b |
| NM_008885 | Pmp22 | NM_011427 | Snail | NM_019654 | Socs5 |
| NM_207237 | Manlcl | NM_031170 | Krt8 | NM_008365 | IllSrl |
| NM_001033326 | Dhrsx | NM_013863 | Bag3 | NR_015521 | 1700030C10Rik |
| NM_175240 | Faml87b | NM_134117 | Pkdcc | NM_007438 | Aldoa |
| NM_001039231 | C230055K05Rik | NM_153574 | Faml3a | NM_139292 | Reep6 |
| NM_027238 | Ttc39b | NM_177782 | Prexl | NM_053179 | Nans |
| NM_010700 | Ldlr | NM_008905 | Ppfibp2 | NM_172841 | Slco5al |
| NM_008217 | Has3 | NM_177152 | Lrig3 | NM_001033135 | Rnfl49 |
| NM_011902 | Tekt2 | NM_011701 | Vim | NM_029219 | Rnfl9b |
| NM_173754 | Usp43 | NM_145823 | Pitpncl | NM_019651 | Ptpn9 |
| NM_172693 | Galntl2 | NM_011104 | Prkce | NM_025602 | Ccdc59 |
| NM_008969 | Ptgsl | NM_172589 | Lhfpl2 | NM_001005420 | Gm347 |
| NM_010446 | Foxa2 | NM_013907 | Fbxw4 | NM_025815 | Cpne8 |
| NM_011577 | Tgfbl | NM_175314 | Adamts9 | NM_030021 | D730039F16Rik |
| NM_025551 | Ndufal2 | NM_009656 | Aldh2 | NM_010498 | Ids |
| NM_008697 | Nin | NM_016669 | Crym | NM_007475 | RplpO |
| NM_145528 | D2Ertd391e | NM_021532 | Dactl | NM_008667 | Nabl |
| NR_030688 | Gm6402 | NM_023732 | Abcb6 | NM_026728 | Echdc2 |
| NM_080553 | Itpr3 | NM_008983 | Ptprk | NM_009546 | Trim25 |
| NM_001038621 | Rabgapll | NM_015774 | Eroll | NM_008621 | Mppl |
| NM_177216 | Cyb5r2 | NM_134127 | Cyp4fl5 | NM_019552 | AbcblO |
| NM_008856 | Prkch | NM_009097 | Rps6kal | NM_026341 | Nudtl3 |
| NM_020561 | Smpdl3a | NM_007885 | Slc26a2 | | |
| NM_007912 | Egfr | NM_029556 | Clybl | | |
| NM_011459 | Serpinb8 | NM_008131 | Glul | | |
| NM_013462 | Adrb3 | NM_028724 | Rin2 | | |
| NM_177448 | Mogat2 | NM_025331 | Gngll | | |
| NM_177815 | Rftl | NM_001081265 | Heatr2 | | |
| NM_011373 | St6galnac4 | NR_027059 | 2810008D09Rik | | |
| NM_011254 | Rbpl | NM_053014 | Agpat3 | | |
| NM_009655 | Alcam | NM_008421 | Kcncl | | |
| NM_011894 | Sh3bp5 | NM_025797 | Cyb5 | | |
| NM_009154 | Sema5a | NM_013923 | Rnfl9a | | |
| NM_182993 | Slcl7a7 | NM_172564 | Tns4 | | |
| NM_011056 | Pde4d | NM_134156 | Actnl | | |
| NM_001033333 | Gm239 | NM_007908 | Eef2k | | |
| NM_053207 | Eglnl | NM_133758 | Usp47 | | |
| NM_177343 | Camkld | NM_008750 | Nxn | | |
| NM_194053 | Rtn4 | NM_011975 | Rpl27a | | |
| NM_008153 | Cmklrl | NM_021423 | Shank3 | | |
| NM_178671 | UbxnlO | NM_134080 | Flnb | | |
| NM_029286 | Ccdc30 | NM_176933 | Dusp4 | | |
| NM_181315 | Car5b | NM_011777 | Zyx | | |
| NM_001081161 | Faml71al | NM_008439 | Khk | | |
| NM_153573 | Fkbpl4 | NM_178256 | Reps2 | | |
| NM_023557 | Slc44a4 | NM_019689 | Arid3b | | |

TABLE 3

GO (Biological Process) Enrichment for genes differentially regulated in SB/AA15. Genes up-regulated in SB are enriched for ectoderm related terms while genes up-regulated in AA15 are enriched for mesoderm and endoderm related terms. P-values were determined from background set of genes that showed expression in SB/AA15 samples

| Term | PValue | Bonferroni | Benjamini |
|---|---|---|---|
| Up-regulated in SB in comparison to AA15 | | | |
| Neuron differentiation | 1.79E−23 | 4.76E−20 | 4.76E−20 |
| Neuron development | 2.48E−17 | 6.59E−14 | 3.30E−14 |
| Neuron projection development | 5.72E−17 | 2.95E−13 | 9.81E−14 |
| Forebrain development | 4.04E−16 | 1.18E−12 | 2.95E−13 |
| Axonogenesis | 1.05E−13 | 2.79E−10 | 5.58E−11 |
| Cell projection organization | 4.54E−13 | 1.20E−09 | 2.01E−10 |
| Neuron projection morphogenesis | 1.53E−12 | 4.06E−09 | 5.80E−10 |
| Axon guidance | 1.71E−12 | 4.55E−09 | 5.68E−10 |
| Cell motion | 2.02E−12 | 5.35E−09 | 5.94E−10 |
| Cell projection morphogenesis | 2.36E−12 | 6.25E−09 | 6.25E−10 |
| Neuron migration | 4.17E−12 | 1.11E−08 | 1.01E−09 |
| Cell morphogenesis involved in neuron differentiation | 4.78E−12 | 1.27E−08 | 1.06E−09 |
| Cell morphogenesis involved in differentiation | 1.29E−11 | 3.42E−08 | 2.63E−09 |
| Cell part morphogenesis | 1.29E−11 | 3.42E−08 | 2.63E−09 |
| Sensory organ development | 6.41E−11 | 1.70E−07 | 1.21E−08 |
| Cell morphogenesis | 1.49E−10 | 3.96E−07 | 2.64E−08 |
| Embryonic morphogenesis | 5.74E−10 | 1.52E−06 | 9.52E−08 |
| Pattern specification process | 6.64E−10 | 1.76E−06 | 1.04E−07 |
| Cell migration | 2.70E−09 | 7.17E−06 | 3.98E−07 |
| Up-regulated in AA15 in comparison to SB | | | |
| Tissue morphogenesis | 5.66E−10 | 1.86E−06 | 1.86E−06 |
| Tube morphogenesis | 1.43E−08 | 4.68E−05 | 2.34E−05 |
| Tube development | 1.75E−08 | 5.74E−05 | 1.91E−05 |
| Regulation of cell proliferation | 4.47E−08 | 1.47E−04 | 3.67E−05 |
| Muscle organ development | 1.02E−07 | 3.34E−04 | 6.68E−05 |
| Epithelium development | 1.09E−07 | 3.59E−04 | 5.99E−05 |
| Morphogenesis of a branching structure | 7.34E−07 | 0.002407415 | 3.44E−04 |
| Embryonic development in birth or egg hatching | 7.95E−07 | 0.002606797 | 3.26E−04 |
| Gastrulation | 8.05E−07 | 0.002639606 | 2.94E−04 |
| Chordate embryonic development | 1.27E−06 | 0.004150463 | 4.16E−04 |
| Muscle tissue morphogenesis | 1.37E−06 | 0.004472863 | 4.07E−04 |
| Cardiac muscle tissue morphogenesis | 1.37E−06 | 0.004472863 | 4.07E−04 |
| Cardiac muscle tissue development | 1.64E−06 | 0.005377126 | 4.49E−04 |
| Blood vessel morphogenesis | 1.79E−06 | 0.005852621 | 4.51E−04 |
| Epithelial cell differentiation | 1.87E−06 | 0.006119825 | 4.38E−04 |
| Embryonic morphogenesis | 2.26E−06 | 0.007406449 | 4.95E−04 |
| Formation of primary germ layer | 2.54E−06 | 0.008290073 | 5.20E−04 |
| Endoderm development | 2.68E−06 | 0.008762516 | 5.18E−04 |
| Striated muscle tissue development | 3.44E−06 | 0.011238338 | 6.28E−04 |
| Heart morphogenesis | 3.63E−06 | 0.011851466 | 6.27E−04 |

TABLE 4

Kegg Pathways enriched in SB/AA15 samples. P-values were determined from background set of genes that showed expression in SB/AA15 samples

| Term | PValue | Fold Enrichment |
|---|---|---|
| Up-regulated in SB in comparison to AA15 | | |
| Axon guidance | 1.57E−08 | 3.709575553 |
| Pathways in cancer | 1.51E−05 | 2.141023185 |
| Focal adhesion | 1.18E−04 | 2.359918402 |
| Wnt signaling pathway | 3.19E−04 | 2.508799161 |
| Basal cell carcinoma | 5.50E−04 | 3.738110749 |
| Colorectal cancer | 5.60E−04 | 3.042648284 |
| Pancreatic cancer | 0.001349684 | 3.115092291 |
| Notch signaling pathway | 0.004505895 | 3.364299674 |
| TGF-beta signaling pathway | 0.006142763 | 2.578007413 |
| ErbB signaling pathway | 0.006142763 | 2.578007413 |
| Melanogenesis | 0.006550121 | 2.429771987 |
| Adherens junction | 0.006669882 | 2.705211726 |
| Chronic myeloid leukemia | 0.006669882 | 2.705211726 |
| Hedgehog signaling pathway | 0.007261218 | 3.115092291 |
| Non-small cell lung cancer | 0.007261218 | 3.115092291 |
| Biosynthesis of unsaturated fatty acids | 0.01278219 | 4.153456388 |
| Small cell lung cancer | 0.014350175 | 2.418777544 |
| Endometrial cancer | 0.019416505 | 2.875469807 |
| Prostate cancer | 0.02078187 | 2.284401013 |
| Regulation of actin cytoskeleton | 0.021865036 | 1.722631682 |
| Chondroitin sulfate biosynthesis | 0.027081384 | 4.247853124 |
| ABC transporters | 0.030854623 | 2.907419472 |
| Renal cell carcinoma | 0.03168407 | 2.403071196 |
| MAPK signaling pathway | 0.043071193 | 1.551668613 |
| VEGF signaling pathway | 0.048220294 | 2.213355049 |
| Up-regulated in AA15 in comparison to SB | | |
| Glioma | 0.001299387 | 2.746580963 |
| Pathways in cancer | 0.002808993 | 1.593770112 |
| Melanoma | 0.003446481 | 2.47579129 |
| Alanine, aspartate and glutamate metabolism | 0.007788248 | 3.348212983 |
| Arginine and proline metabolism | 0.007922603 | 2.605920482 |

TABLE 4-continued

Kegg Pathways enriched in SB/AA15 samples.
P-values were determined from background set of genes that
showed expression in SB/AA15 samples

| Term | PValue | Fold Enrichment |
|---|---|---|
| Cysteine and methionine metabolism | 0.01329234 | 3.043829985 |
| p53 signaling pathway | 0.019104884 | 2.183617163 |
| Amino sugar and nucleotide sugar metabolism | 0.020808361 | 2.56823155 |
| ABC transporters | 0.023613091 | 2.511159737 |
| Fatty acid metabolism | 0.023613091 | 2.511159737 |
| Non-small cell lung cancer | 0.024969204 | 2.325147905 |
| MAPK signaling pathway | 0.02912413 | 1.468791545 |
| Endocytosis | 0.029288254 | 1.553935481 |
| Nitrogen metabolism | 0.031517906 | 3.275425744 |
| Tight junction | 0.037866683 | 1.674106492 |
| Focal adhesion | 0.040549519 | 1.521914992 |
| Glycolysis/Gluconeogenesis | 0.040867493 | 2.031085082 |
| Bladder cancer | 0.045432262 | 2.391580702 |

TABLE 5

List of heptamer primers used for sequencing-library generation.
44 unique primers were split into three tubes with some primers
repeated to get coverage of ~80% mouse transcriptome

```
 1. cccagtg (SEQ ID NO:  8)     1. caaagcc (SEQ ID NO: 26)     1. cacacac (SEQ ID NO: 51)
 2. ccccaga (SEQ ID NO:  9)     2. caacccc (SEQ ID NO: 27)     2. cagcagc (SEQ ID NO: 52)
 3. ccccccaa (SEQ ID NO: 10)    3. cccagca (SEQ ID NO: 28)     3. ccaccag (SEQ ID NO: 53)
 4. ctcccca (SEQ ID NO: 11)     4. cccccaa (SEQ ID NO: 29)     4. cccagca (SEQ ID NO: 54)
 5. cttcacg (SEQ ID NO: 12)     5. ctcgtcc (SEQ ID NO: 30)     5. cccccaa (SEQ ID NO: 55)
 6. gcaacag (SEQ ID NO: 13)     6. cttcccc (SEQ ID NO: 31)     6. ccttccc (SEQ ID NO: 56)
 7. tgacagc (SEQ ID NO: 14)     7. gcctctc (SEQ ID NO: 32)     7. cttcccc (SEQ ID NO: 57)
 8. tggctct (SEQ ID NO: 15)     8. gcctctg (SEQ ID NO: 33)     8. gcaacag (SEQ ID NO: 58)
 9. tggcttc (SEQ ID NO: 16)     9. gcgaact (SEQ ID NO: 34)     9. gcctcag (SEQ ID NO: 59)
10. tccctcc (SEQ ID NO: 17)    10. tcagccc (SEQ ID NO: 35)    10. tccctcc (SEQ ID NO: 60)
11. ccttccc (SEQ ID NO: 18)    11. tctccga (SEQ ID NO: 36)    11. tgaccca (SEQ ID NO: 61)
12. cagaccc (SEQ ID NO: 19)    12. tgccatc (SEQ ID NO: 37)    12. tgagcct (SEQ ID NO: 62)
13. gcaaacc (SEQ ID NO: 20)    13. tgccttg (SEQ ID NO: 38)    13. cagcact (SEQ ID NO: 63)
14. ccaggac (SEQ ID NO: 21)    14. tgagcct (SEQ ID NO: 39)    14. gcgaact (SEQ ID NO: 64)
15. cacacac (SEQ ID NO: 22)    15. tcctcgt (SEQ ID NO: 40)    15. ctcccag (SEQ ID NO: 65)
16. tctccga (SEQ ID NO: 23)    16. tctgcct (SEQ ID NO: 41)    16. gccaaag (SEQ ID NO: 66)
17. cctccca (SEQ ID NO: 24)    17. ctgccct (SEQ ID NO: 42)    17. ccccaga (SEQ ID NO: 67)
18. tgaccca (SEQ ID NO: 25)    18. tgccact (SEQ ID NO: 43)    18. tcagcca (SEQ ID NO: 68)
                               19. cttcacg (SEQ ID NO: 44)    19. gaagcca (SEQ ID NO: 69)
                               20. gcaacag (SEQ ID NO: 45)    20. tgacagc (SEQ ID NO: 70)
                               21. cctctgc (SEQ ID NO: 46)
                               22. gcaaacc (SEQ ID NO: 47)
                               23. ccccaga (SEQ ID NO: 48)
                               24. ctcagca (SEQ ID NO: 49)
                               25. tgacagc (SEQ ID NO: 50)
```

TABLE 6

List of quantitative RT-PCR primers used in the study

| Gene | Forward Primer | SEQ ID NO: | Reverse Primer | SEQ ID NO: |
|---|---|---|---|---|
| Lefty 1 | CGCTGAATCTGGGCTGAGTCCC | 71 | GCCTAGGTTGGACATGTTTGCCCA | 134 |
| Lefty2 | TGCAAGTAGCCGACTTCGGAGC | 72 | CCTATTCCCAGGCCTCTGGCCA | 135 |
| Gsc | GGGGGTCGAGAAAGCAACGAGG | 73 | ACGAGGCTCACGCAGGCAGC | 136 |
| Flk-1 | AGAGGAAGTGTGCGACCCCAA | 74 | CACTGGCCGGCTCTTTCGCTT | 137 |
| Oct4 | TGAAGTGCCCGAAGCCCTCCCTA | 75 | GCCCTTCTGGCGCCGGTTACA | 138 |
| Mesp1 | TCTAGAAACCTGGACGCCGCC | 76 | TCCGTTGCATTGTCCCCTCCAC | 139 |
| T | CTCCGATGTATGAAGGGGCTGCT | 77 | GCTATGAGGAGGCTTTGGGCCG | 140 |
| Foxa2 | CCCCATGCCAGGCAGCTTGG | 78 | AAGTGTCTGCAGCCAGGGGC | 141 |
| Sox1 | TTCCCCAGGACTCCGAGGCG | 79 | GTTCAGTCTAAGAGGCCAGTCTGGT | 142 |
| Arx | AAGCATAGCCGCGCTGAGGC | 80 | TTCGGGGAACGCCCTAGGGG | 143 |
| Lnsm1 | TACAGCTCCCCGGGCCTGAC | 81 | ACTCTAGCAGGCCGGACGCA | 144 |
| Pax6 | ACCTCCTCATACTCGTG | 82 | ACTGATACCGTGCCTT | 145 |
| Dbx1 | GACGTGCAGCGGAAAGCCCT | 83 | CGCTAGACAGGAGCTCGCGC | 146 |
| Dmrt3 | AACCGGCCACCCCTGGAAGT | 84 | GTCGCCCCGCAACCTTTCA | 147 |
| Hes5 | TCCGACCCCGTGGGGTTGTT | 85 | TCTACGGGCTGGGGTGAGCC | 148 |
| Neurog2 | ACACGAGACTCGGGCGAGCT | 86 | CCGGAACCGAGCACGGTGTC | 149 |
| Lhx2 | TGGGCTCAGCCGGGGCTAAT | 87 | ACAGCTAAGCGCGGCGTTGT | 150 |
| Pax5 | ACACTGTGCCCAGCGTCAGC | 88 | GCACTGGGGACGTGATGCC | 151 |
| Lhx5 | GAGCTCAACGAAGCGGCCGT | 89 | CCGAGAAATTGCGCAGGCGC | 152 |
| Sox2 | GCACATGAAGGAGCACCCGGA | 90 | GGTTCACGCCCGCACCCAG | 153 |
| Asb5 | GGGACACGCCACTGCATGCT | 91 | GCCAAGTCGACAGGCCGCAA | 154 |
| Lmx1a | TGACGTCATGCCCGGGACCA | 92 | GCCCCCTACACCCGCCTCAT | 155 |
| Pax3 | CCCCCACCTATAGCACCGCAGG | 93 | ACATGCCTCCAGTTCCCCGTTCT | 156 |
| Hoxa5 | AGGGAACCGAGTACATGTCCCAGT | 94 | TGCAACTGGTAGTCCGGGCCA | 157 |
| Trim12 | TGCGCAGCCTCCAGACGATG | 95 | TCTGGAGCAGTGCAACGGCA | 158 |
| Afp | TTCCTCCCAGTGCGTGACGGA | 96 | TCCTCGGTGGCTTCCGGAACA | 159 |
| Dppa3 | CCGGCGCAGTCTACGGAACC | 97 | ACCGACAACAAAGTGCGGACCC | 160 |
| Fgf8 | GCGAAGCTCATTGTGGAGAC | 98 | CACGATCTCTGTGAATACGCA | 161 |
| Noda1 | ACCAACCATGCCTACATCCAGAG | 99 | CCCTGCCATTGTCCACATAAAGC | 162 |
| Epha1 | TACGCCTGCCCAGCCTGAGT | 100 | GGTGTCCAGCCCAGCCGAAC | 163 |
| Rab25 | TCAGCCAGGCCCGAGAGGTC | 101 | GATGGCACTGGTCCGGGTGC | 164 |
| Evx1 | GAGTGGCGTCACCAGCGGTACT | 102 | TCACCTTGTGATGCGAGCGC | 165 |
| Lrrc6 | GGGAAATCCTGCCTGCCGGTC | 103 | CTGTGATTCGGCCCATGGTGCTT | 166 |
| Pou6f1 | CGCCTTTCCTGCCTGGTGGG | 104 | GCTAGCAGTGGGCAGTGGCC | 167 |
| Pgr | CGCCATCTACCAGCCGCTCG | 105 | ACTGTGGGCTCTGGCTGGCT | 168 |
| Foxa3 | TTTGGGGGCTACGGGGCTGA | 106 | TGCAGCCCACGCCCATCATG | 169 |
| E112 | TGCAGGCCTCCTACCACCCC | 107 | TCCCCAGGCCTTCTGGAGTGC | 170 |

TABLE 6-continued

List of quantitative RT-PCR primers used in the study

| Gene | Forward Primer | SEQ ID NO: | Reverse Primer | SEQ ID NO: |
|---|---|---|---|---|
| Lbh | ACGTTGGGGCAAGAGCGTGG | 108 | GAGACGGGGAGGGGTGAC | 171 |
| Etv4 | GAAGGTGGCTGGCGAACGCT | 109 | GCGGGGCCAGTGAGTTCTGG | 172 |
| Klf9 | CCGCGTACTCGGCTGATGCC | 110 | CACACGTGGCGGTCGCAAGT | 173 |
| Wnt3a | ACCAAGACCTAACAAACCC | 111 | CATGGACATCACGGACC | 174 |
| Prdm1 | GCCGAGGTGCGCGTCAGTAC | 112 | GGGGCAGCCAAGGTCGTACC | 175 |
| Ankrd1 | ACGCAGACGGGAACGGAAGC | 113 | TGCGGCACTCCTGACGTTGC | 176 |
| Per2 | GGTGGCCTCTGCAAGCCAGG | 114 | CCTCCGTGCTCAGTGGCTGC | 177 |
| Hes1 | CCCTGCAAGTTGGGCAGCCA | 115 | CGAAGGCCCCGTTGGGGATG | 178 |
| Bnc1 | GCTGGAGCACCTGGGTGAGC | 116 | CCTCCACTGTGCACGCGTGT | 179 |
| Foxc2 | AGGGACTTTGCTTCTTTTTCCGGGC | 117 | CCCGCAGCGTCAGCGAGCTA | 180 |
| Prdm6 | CCGGCCTTTCAAGTGCGGCT | 118 | GGCATGCGCTGGTGTCGACT | 181 |
| Armc4 | GCATCCCCTTGCTGGCTCGG | 119 | GGCCATGGCACAGTGCTCCT | 182 |
| Cxcr4 | TACCCCGATAGCCTGT | 120 | GCACGATGCTCTCGAA | 183 |
| Tbx3 | CCAAGCGATCACGCAACGTGG | 121 | CTCTGACGATGTGGAACCGCGG | 184 |
| Arg1 | GCGAGACGTAGACCCTGGGG | 122 | GGTCGCCGGGGTGAATGCTG | 185 |
| Foxq1 | GGAGCCGCCGCAGGGTTATATTG | 123 | TGGCGCACCCGCTACTTTTGAG | 186 |
| Asb4 | TCACCTCCGTGCGTCCTGCT | 124 | TTCGGGCAAGAGTGGCAAGCC | 187 |
| Six2 | ACTCGTCGTCCAGTCCCGCTC | 125 | CAAGGTTGGCCGACATGGGGT | 188 |
| Lhx1 | ACTAGGGACCGAGGGACGCG | 126 | CAGTTTGGCGCGGATTGCCG | 189 |
| Sox 17 | GAGCCAAAGCGGAGTCTC | 127 | TGCCAAGGTCAACGCCTTC | 190 |
| Cer1 | AGAGGTTCTGGCATCGGTTCA | 128 | TCTCCCAGTGTACTTCGTGGC | 191 |
| Creb3l1 | ACAGGACGGACACCCTGGCA | 129 | GGTCAGCCCAGGGGAGCAGT | 192 |
| Bcl6 | AAGCACGGCGCCATCACCAA | 130 | TTTGGGGAGCTCCGGAGGCA | 193 |
| Hey1 | AATGGCCACGGGAACGCTGG | 131 | CACCACGGGAAGCACCGGTC | 194 |
| Basp1 | AGGGGGCGGGGAGAATCCAAA | 132 | GGAGCCTAGGGGACAGCGGTT | 195 |
| β-Actin | GCTGTATTCCCCTCCATCGTG | 133 | CACGGTTGGCCTTAGGGTTCAG | 196 |

REFERENCES

1. Adli M, Zhu J, Bernstein B E. 2010. Genome-wide chromatin maps derived from limited numbers of hematopoietic progenitors. *Nat Methods* 7(8): 615-618.
2. Armes N A, Smith J C. 1997. The ALK-2 and ALK-4 activin receptors transduce distinct mesoderm-inducing signals during early Xenopus development but do not co-operate to establish thresholds. *Development* 124(19): 3797-3804.
3. Armour C D, Castle J C, Chen R, Babak T, Loerch P, Jackson S, Shah J K, Dey J, Rohl C A, Johnson J M et al. 2009. Digital transcriptome profiling using selective hexamer priming for cDNA synthesis. *Nat Methods* 6(9): 647-649.
4. Asmann Y W, Klee E W, Thompson E A, Perez E A, Middha S, Oberg A L, Therneau T M, Smith D I, Poland G A, Wieben E D et al. 2009. 3' tag digital gene expression profiling of human brain and universal reference RNA using Illumina Genome Analyzer. *BMC Genomics* 10: 531.
5. Bloom J S, Khan Z, Kruglyak L, Singh M, Caudy A A. 2009. Measuring differential gene expression by short read sequencing: quantitative comparison to 2-channel gene expression microarrays. *BMC Genomics* 10: 221.
6. Chen B, Dodge M E, Tang W, Lu J, Ma Z, Fan C W, Wei S, Hao W, Kilgore J, Williams N S et al. 2009. Small molecule-mediated disruption of Wnt-dependent signaling in tissue regeneration and cancer. *Nat Chem Biol* 5(2): 100-107.
7. Dahle O, Kumar A, Kuehn M R. 2010. Nodal signaling recruits the histone demethylase Jmjd3 to counteract polycomb-mediated repression at target genes. *Sci Signal* 3(127): ra48.

8. Fang Z, Cui X. 2011. Design and validation issues in RNA-seq experiments. *Brief Bioinform* 12(3): 280-287.
9. Faust C, Schumacher A, Holdener B, Magnuson T. 1995. The eed mutation disrupts anterior mesoderm production in mice. *Development* 121(2): 273-285.
10. Gadue P, Huber T L, Paddison P J, Keller G M. 2006. Wnt and TGF-beta signaling are required for the induction of an in vitro model of primitive streak formation using embryonic stem cells. *Proc Natl Acad Sci USA* 103(45): 16806-16811.
11. Gurdon J B, Harger P, Mitchell A, Lemaire P. 1994. Activin signalling and response to a morphogen gradient. *Nature* 371(6497): 487-492.
12. Guzman-Ayala M, Lee K L, Mavrakis K J, Goggolidou P, Norris D P, Episkopou V. 2009. Graded Smad2/3 activation is converted directly into levels of target gene expression in embryonic stem cells. *PLoS One* 4(1): e4268.
13. Hansen K D, Brenner S E, Dudoit S. 2010. Biases in Illumina transcriptome sequencing caused by random hexamer priming. *Nucleic Acids Res* 38(12): e131.
14. Hoeijmakers W A, Bartfai R, Francoijs K J, Stunnenberg H G. 2011. Linear amplification for deep sequencing. *Nat Protoc* 6(7): 1026-1036.
15. Hoodless P A, Pye M, Chazaud C, Labbe E, Attisano L, Rossant J, Wrana J L. 2001. FoxH1 (Fast) functions to specify the anterior primitive streak in the mouse. *Genes Dev* 15(10): 1257-1271.
16. Inman G J, Nicolas F J, Callahan J F, Harling J D, Gaster L M, Reith A D, Laping N J, Hill C S. 2002. SB-431542 is a potent and specific inhibitor of transforming growth factor-beta superfamily type I activin receptor-like kinase (ALK) receptors ALK4, ALK5, and ALK7. *Mol Pharmacol* 62(1): 65-74.
17. Jones C M, Kuehn M R, Hogan B L, Smith J C, Wright C V. 1995. Nodal-related signals induce axial mesoderm and dorsalize mesoderm during gastrulation. *Development* 121(11): 3651-3662.
18. Katoh M. 2006. CER1 is a common target of WNT and NODAL signaling pathways in human embryonic stem cells. *Int J Mol Med* 17(5): 795-799.
19. Kattman S J, Witty A D, Gagliardi M, Dubois N C, Niapour M, Hotta A, Ellis J, Keller G. 2011. Stage-specific optimization of activin/nodal and BMP signaling promotes cardiac differentiation of mouse and human pluripotent stem cell lines. *Cell Stem Cell* 8(2): 228-240.
20. Kishigami S, Mishina Y. 2005. BMP signaling and early embryonic patterning. *Cytokine Growth Factor Rev* 16(3): 265-278.
21. Labaj P P, Leparc G G, Linggi B E, Markillie L M, Wiley H S, Kreil D P. 2011. Characterization and improvement of RNA-Seq precision in quantitative transcript expression profiling. *Bioinformatics* 27(13): i383-391.
22. Labbe E, Silvestri C, Hoodless P A, Wrana J L, Attisano L. 1998. Smad2 and Smad3 positively and negatively regulate TGF beta-dependent transcription through the forkhead DNA-binding protein FAST2. *Mol Cell* 2(1): 109-120.
23. Levin J Z, Berger M F, Adiconis X, Rogov P, Melnikov A, Fennell T, Nusbaum C, Garraway L A, Gnirke A. 2009. Targeted next-generation sequencing of a cancer transcriptome enhances detection of sequence variants and novel fusion transcripts. *Genome Biol* 10(10): R115.
24. Li H, Lovci M T, Kwon Y S, Rosenfeld M G, Fu X D, Yeo G W. 2008. Determination of tag density required for digital transcriptome analysis: application to an androgen-sensitive prostate cancer model. *Proc Natl Acad Sci USA* 105(51): 20179-20184.
25. Li J B, Levanon E Y, Yoon J K, Aach J, Xie B, Leproust E, Zhang K, Gao Y, Church G M. 2009. Genome-wide identification of human RNA editing sites by parallel DNA capturing and sequencing. *Science* 324(5931): 1210-1213.
26. Marguerat S, Bahler J. 2010. RNA-seq: from technology to biology. *Cell Mol Life Sci* 67(4): 569-579.
27. Marioni J C, Mason C E, Mane S M, Stephens M, Gilad Y. 2008. RNA-seq: an assessment of technical reproducibility and comparison with gene expression arrays. *Genome Res* 18(9): 1509-1517.
28. Markham N R, Zuker M. 2008. UNAFold: software for nucleic acid folding and hybridization. *Methods Mol Biol* 453: 3-31.
29. Metzker M L. 2010. Sequencing technologies—the next generation. *Nat Rev Genet* 11(1): 31-46.
30. Mortazavi A, Williams B A, McCue K, Schaeffer L, Wold B. 2008. Mapping and quantifying mammalian transcriptomes by RNA-Seq. *Nat Methods* 5(7): 621-628.
31. Norris D P, Brennan J, Bikoff E K, Robertson E J. 2002. The Foxh1-dependent autoregulatory enhancer controls the level of Nodal signals in the mouse embryo. *Development* 129(14): 3455-3468.
32. Nostro M C, Cheng X, Keller G M, Gadue P. 2008. Wnt, activin, and BMP signaling regulate distinct stages in the developmental pathway from embryonic stem cells to blood. *Cell Stem Cell* 2(1): 60-71.
33. Oshlack A, Wakefield M J. 2009. Transcript length bias in RNA-seq data confounds systems biology. *Biol Direct* 4: 14.
34. Ozsolak F, Milos P M. 2011. RNA sequencing: advances, challenges and opportunities. *Nat Rev Genet* 12(2): 87-98.
35. Pevny L H, Sockanathan S, Placzek M, Lovell-Badge R. 1998. A role for SOX1 in neural determination. *Development* 125(10): 1967-1978.
36. Rossant J, Tam P P. 2009. Blastocyst lineage formation, early embryonic asymmetries and axis patterning in the mouse. *Development* 136(5): 701-713.
37. Shiratori H, Sakuma R, Watanabe M, Hashiguchi H, Mochida K, Sakai Y, Nishino J, Saijoh Y, Whitman M, Hamada H. 2001. Two-step regulation of left-right asymmetric expression of Pitx2: initiation by nodal signaling and maintenance by Nkx2. *Mol Cell* 7(1): 137-149.
38. Sulzbacher S, Schroeder I S, Truong T T, Wobus A M. 2009. Activin A-induced differentiation of embryonic stem cells into endoderm and pancreatic progenitors—the influence of differentiation factors and culture conditions. *Stem Cell Rev* 5(2): 159-173.
39. Tam P P, Kanai-Azuma M, Kanai Y. 2003. Early endoderm development in vertebrates: lineage differentiation and morphogenetic function. *Curr Opin Genet Dev* 13(4): 393-400.
40. Tang F, Barbacioru C, Wang Y, Nordman E, Lee C, Xu N, Wang X, Bodeau J, Tuch B B, Siddiqui A et al. 2009. mRNA-Seq whole-transcriptome analysis of a single cell. *Nat Methods* 6(5): 377-382.
41. Vallier L, Mendjan S, Brown S, Chng Z, Teo A, Smithers L E, Trotter M W, Cho C H, Martinez A, Rugg-Gunn P et al. 2009a. Activin/Nodal signalling maintains pluripotency by controlling Nanog expression. *Development* 136(8): 1339-1349.
42. Vallier L, Touboul T, Chng Z, Brimpari M, Hannan N, Millan E, Smithers L E, Trotter M, Rugg-Gunn P, Weber A et al. 2009b. Early cell fate decisions of human embryonic stem cells and mouse epiblast stem cells are controlled by the same signalling pathways. *PLoS One* 4(6): e6082.
43. Wang Z, Gerstein M, Snyder M. 2009. RNA-Seq: a revolutionary tool for transcriptomics. *Nat Rev Genet* 10(1): 57-63.
44. Willems E, Leyns L. 2008. Patterning of mouse embryonic stem cell-derived pan-mesoderm by Activin A/Nodal and Bmp4 signaling requires Fibroblast Growth Factor activity. *Differentiation* 76(7): 745-759.
45. Yamamoto M, Meno C, Sakai Y, Shiratori H, Mochida K, Ikawa Y, Saijoh Y, Hamada H. 2001. The transcription factor FoxH1 (FAST) mediates Nodal signaling during anterior-posterior patterning and node formation in the mouse. *Genes Dev* 15(10): 1242-1256.
46. Zajac P, Oberg C, Ahmadian A. 2009. Analysis of short tandem repeats by parallel DNA threading. *PLoS One* 4(11): e7823.
47. Zhang K, Li J B, Gao Y, Egli D, Xie B, Deng J, Li Z, Lee J H, Aach J, Leproust E M et al. 2009. Digital RNA allelotyping reveals tissue-specific and allele-specific gene expression in human. *Nat Methods* 6(8): 613-618.
48. Zhang Y, Handley D, Kaplan T, Yu H, Bais A S, Richards T, Pandit K V, Zeng Q, Benos P V, Friedman N et al. 2011. High throughput determination of TGFbeta1/SMAD3 targets in A549 lung epithelial cells. *PLoS One* 6(5): e20319.
49. Chen B, Dodge M E, Tang W, Lu J, Ma Z, Fan C W, Wei S, Hao W, Kilgore J, Williams N S et al. 2009. Small molecule-mediated disruption of Wnt-dependent signaling in tissue regeneration and cancer. *Nat Chem Biol* 5(2): 100-107.
50. Gadue P, Huber T L, Paddison P J, Keller G M. 2006. Wnt and TGF-beta signaling are required for the induction of an in vitro model of primitive streak formation using embryonic stem cells. *Proc Natl Acad Sci USA* 103(45): 16806-16811.
51. Langmead B. 2010. Aligning short sequencing reads with Bowtie. *Curr Protoc Bioinformatics* Chapter 11: Unit 11 17.
52. Willems E, Leyns L. 2008. Patterning of mouse embryonic stem cell-derived pan-mesoderm by Activin A/Nodal and Bmp4 signaling requires Fibroblast Growth Factor activity. *Differentiation* 76(7): 745-759.
53. Zhao G, Guan Y. 2010. Polymerization behavior of Klenow fragment and Taq DNA polymerase in short primer extension reactions. *Acta Biochim Biophys Sin (Shanghai)* 42(10): 722-728.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a WAN, and the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described herein, and other implementations, enhancements and variations can be made based on what is described and illustrated in this application and attached Appendix.

What is claimed is:

1. A method of amplifying and sequencing low abundance transcripts, comprising:
   (a) determining a list of potential primer binding sites in a mammalian transcriptome that have an open configuration and are positioned adjacent to a unique region in the mammalian transcriptome;
   (b) determining at least one set of gene pool specific heptamer primers based on the list of potential primer binding sites using an iterative randomized algorithm, wherein each of the gene pool specific heptamer primers complementary binds to at least one of the potential primer binding sites and is capable of generating an amplicon which has:
      (i) a length between 50 and 300 bp;
      (ii) a GC content not exceeding 58%;
      (iii) at least one primer-binding site having a $\Delta G \geq -2$ Kcal/mol;
      (iv) forward and reverse primer-binding sites in an open configuration; and
      (v) at least one uniquely mappable 32 mer end;
   (c) amplifying at least a portion of the mammalian transcriptome using the at least one set of gene pool specific heptamer primers to form amplicons;
   (d) ligating adapter oligos to the amplicons to form adapted amplicons;
   (e) amplifying the adapted amplicons; and
   (f) subjecting the amplified, adapted amplicons to synthesis-based sequencing.

2. The method of claim 1, wherein said iterative randomized algorithm comprises iteratively scoring and ranking a plurality of primer sets.

3. The method of claim 1, wherein each of the gene pool specific heptamer primers complementary binds directly upstream of at least one unique region in the mammalian transcriptome.

4. The method of claim 1, wherein the at least one set of gene pool specific heptamer primers comprises the following 44 heptamer primers:
   1) caaagcc; 2) caacccc; 3) cacacac; 4) cagaccc; 5) cagcact; 6) cagcagc; 7) ccaccag; 8) ccaggac; 9) cccagca; 10) cccagtg; 11) ccccaga; 12) ccccaa; 13) cctccca; 14) cctctgc; 15) ccttccc; 16) ctcagca; 17) ctcccag; 18) ctcccca; 19) ctcgtcc; 20) ctgccct; 21) cttcacg; 22) cttcccc; 23) gaagcca; 24) gcaaacc; 25) gcaacag; 26) gccaaag; 27) gcctcag; 28) gcctctc; 29) gcctctg; 30) gcgaact; 31) tcagcca; 32) tcagccc; 33) tccctcc; 34) tcctcgt; 35) tctccga; 36) tctgcct; 37) tgacagc; 38) tgaccca; 39) tgagcct; 40) tgccact; 41) tgccatc; 42) tgccttg; 43) tggctct; and 44) tggcttc.

5. The method of claim 1, wherein the step of amplifying at least a portion of the mammalian transcriptome is optimized for heptamer hybridization and to reduce mis-priming and primer dimerization.

6. The method of claim 1, wherein the mammalian transcriptome is 10-50 picograms of nucleic acid.

7. The method of claim 1, wherein the synthesis-based sequencing is quantitative and competent to measure differential gene expression for low abundant transcripts.

8. The method of claim 1, wherein the step of amplifying at least a portion of the mammalian transcriptome comprises:
   extending heptamer primers with a mesophilic polymerase; and
   amplifying the extend heptamer primers with a thermophilic polymerase.

9. The method of claim 8, wherein the mesophilic polymerase is Klenow polymerase and the thermophilic polymerase is Taq polymerase.

* * * * *